United States Patent

Lorenz et al.

Patent Number: 5,925,597
Date of Patent: Jul. 20, 1999

[54] PHENYLSULFONYLUREAS, PROCESSES FOR THEIR PREPARATION, AND THEIR USE AS HERBICIDES AND PLANT GROWTH REGULATORS

[75] Inventors: Klaus Lorenz, Weiterstadt; Lothar Willms, Hofheim; Klaus Bauer, Hanau; Hermann Bieringer, Eppstein, all of Germany

[73] Assignee: Hoechst Schering AgrEvo GmbH, Berlin, Germany

[21] Appl. No.: 08/829,250

[22] Filed: Mar. 31, 1997

Related U.S. Application Data

[62] Division of application No. 08/322,610, Oct. 13, 1994, Pat. No. 5,648,315.

Foreign Application Priority Data

Oct. 15, 1993 [DE] Germany .................. 43 35 297

[51] Int. Cl.⁶ .................. C07D 251/42; A01N 43/66
[52] U.S. Cl. .................. 504/212; 504/213; 544/211; 544/212; 544/206; 544/207; 544/208; 544/209; 544/216; 544/217; 544/218; 544/219; 544/113
[58] Field of Search .................. 504/212, 213; 544/211, 212, 206, 209, 218

[56] References Cited

U.S. PATENT DOCUMENTS 4,786,314 11/1988 Artz .................. 544/206
4,927,453 5/1990 Gee .................. 544/321

*Primary Examiner*—John M. Ford
*Attorney, Agent, or Firm*—Frommer Lawrence & Haug LLP

[57] ABSTRACT

Compounds of the formula (I) and their salts as defined in claim 1,

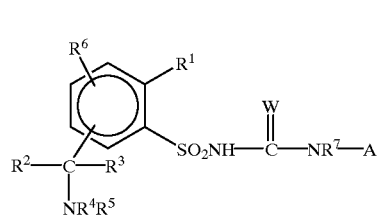

in which $R^1$ is CO—Q—$R^8$, where $R^8$=H or R
$R^2$ and $R^3$ are H or ($C_1$–$C_4$)alkyl,
$R^4$ is H, R, RO, OH, RCO, $RSO_2$, $PhSO_2$
$R^5$ is $RSO_2$, $PhSO_2$, PhCO, $RNHSO_2$, $R_2NSO_2$, RCO, CHO, $COCOR^1$, CW—T—$R^9$, CW—$NR^{10}R^{11}$, CW—$N(R^{12})_2$ or
$R^4$ and $R^5$ together are the chain $(CH_2)_mB$ or —$B^1$—$(CH_2)_{m1}B$— where B=$SO_2$, CO; m=3, 4; $m^1$=2, 3;
T and W=O, S; Q=O, S, $NR^{13}$ where $R^{13}$=H, R;
$R^6$=H, R, RO, RCO, ROCO, Hal, $NO_2$, CN;
$R^7$=H, $CH_3$; $R^9$=R; $R^{10}$, $R^{11}$=H, R; $N(R^{12})_2$=heterocycle
A=pyrimidinyl and triazinyl radical or an analog thereof, where R=(substituted) aliphatic hydrocarbon radical, are suitable as selective herbicides. They are prepared by analogous processes via sulfonamides, some of which are new, of the formula (II).

9 Claims, No Drawings

PHENYLSULFONYLUREAS, PROCESSES FOR THEIR PREPARATION, AND THEIR USE AS HERBICIDES AND PLANT GROWTH REGULATORS

This application is a division of application Ser. No. 08/322,610, filed Oct. 13, 1994, now U.S. Pat. No. 5,648,315.

It is known that some phenylsulfonylureas possess herbicidal and plant growth-regulating properties; cf. U.S. Pat. No. 4,786,314, U.S. Pat. No. 4,927,453 and WO 89/10921. However in some cases these phenylsulfonylureas have disadvantages in use, for example a high persistence or inadequate selectivity in important crops.

Phenylsulfonylureas having specific radicals on the phenyl ring have now been found which can be employed advantageously as herbicides and plant growth regulators.

The present invention relates to compounds of the formula (I) or their salts,

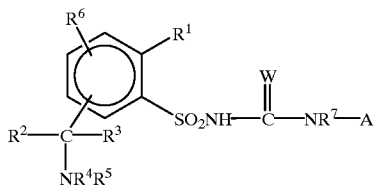

(I)

in which $R^1$ is CO—Q—$R^8$, $R^2$ and $R^3$ independently of one another are H or ($C_1$–$C_4$) alkyl, $R_4$ is H, ($C_1$–$C_8$)alkyl which is unsubstituted or is substituted by one or more radicals from the group consisting of halogen, ($C_1$–$C_4$)alkoxy, ($C_1$–$C_4$)alkylthio, ($C_1$–$C_4$)alkylsulfinyl, ($C_1$–$C_4$)alkylsulfonyl, [($C_1$–$C_4$) alkoxy]carbonyl and CN, or is ($C_3$–$C_6$)alkenyl which is unsubstituted or is substituted by one or more halogen atoms, or is ($C_3$–$C_6$)alkynyl which is unsubstituted or is substituted by one or more halogen atoms, or is hydroxyl, ($C_1$–$C_4$)alkoxy, [($C_1$–$C_4$)alkyl]carbonyl or ($C_1$–$C_4$)alkylsulfonyl, each of the three latter radicals being unsubstituted or substituted in the alkyl moiety by one or more halogen atoms or by ($C_1$–$C_4$)alkoxy or ($C_1$–$C_4$)alkylthio, or is phenylsulfonyl in which the phenyl radical is unsubstituted or substituted, preferably by one or more radicals from the group consisting of halogen, CN, $NO_2$, ($C_1$–$C_4$)alkyl, ($C_1$–$C_4$)haloalkyl and ($C_1$–$C_4$)alkoxy, and $R^5$ is ($C_1$–$C_4$)alkylsulfonyl or ($C_3$–$C_6$)alkenylsulfonyl, each of the two latter radicals being unsubstituted or substituted by one or more halogen atoms or by ($C_1$–$C_4$)alkoxy or ($C_1$–$C_4$)alkylthio, or is phenylsulfonyl or phenylcarbonyl, the phenyl radical in each of the two latter radicals being unsubstituted or substituted, preferably by one or more radicals from the group consisting of halogen, CN, $NO_2$, ($C_1$–$C_4$)alkyl, ($C_1$–$C_4$)haloalkyl and ($C_1$–$C_4$)alkoxy, or is mono- or di-[($C_1$–$C_4$)alkyl]aminosulfonyl or [($C_1$–$C_6$)alkyl]carbonyl, each of the three latter radicals being unsubstituted or substituted by one or more radicals from the group consisting of halogen, ($C_1$–$C_4$)alkoxy, ($C_1$–$C_4$) alkylthio, ($C_1$–$C_4$)alkylsulfinyl, ($C_1$–$C_4$)alkylsulfonyl, [($C_1$–$C_4$)alkyl]carbonyl, [($C_1$–$C_4$)alkoxy]carbonyl and CN, or is formyl, a group of the formula —CO—CO—R' in which R'=H, OH, ($C_1$–$C_4$)alkoxy or ($C_1$–$C_4$)alkyl, or is [($C_3$–$C_6$)cycloalkyl]carbonyl, [($C_2$–$C_6$)alkenyl] carbonyl or [($C_2$–$C_6$)alkynyl]carbonyl, each of the three latter radicals being unsubstituted or substituted by one or more halogen atoms, or is a group of the formula

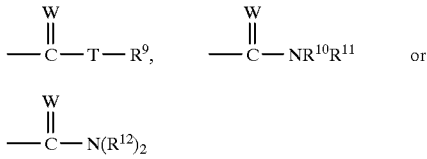

or $R^4$ and $R^5$ together are a chain of the formula (—$CH_2$)$_m$ B— or —$B_1$—($CH_2$)$_{m1}$—B—, the chain being unsubstituted or substituted by one or more, preferably up to four, ($C_1$–$C_3$)alkyl radicals and m being 3 or 4 or $m^1$ being 2 or 3, and W is an oxygen or sulfur atom (i.e. O or S), B and $B^1$ independently of one another are $SO_2$ or CO, Q is O, S or —$NR^{13}$—, T is O or S, $R^6$ is H, ($C_1$–$C_4$)alkyl, ($C_1$–$C_4$)alkoxy, [($C_1$–$C_4$)alkyl] carbonyl or [($C_1$–$C_4$)alkoxy]carbonyl, each of the 4 latter radicals being unsubstituted or substituted in the alkyl moiety by one or more halogen atoms, or is halogen, $NO_2$ or CN, $R^7$ is H or $CH_3$, $R^8$ is H, ($C_1$–$C_4$)alkyl, ($C_3$–$C_4$)alkenyl or ($C_3$–$C_4$)alkynyl, each of the three latter radicals being unsubstituted or substituted by one or more radicals from the group consisting of halogen, ($C_1$–$C_4$)alkoxy, ($C_1$–$C_4$) alkylthio, [($C_1$–$C_4$)alkyl]carbonyl and [($C_1$–$C_4$)alkoxy] carbonyl, $R^9$ is ($C_1$–$C_4$)alkyl, ($C_3$–$C_4$)alkenyl or ($C_3$–$C_4$)alkynyl, each of the three latter radicals being unsubstituted or substituted by one or more radicals from the group consisting of halogen, ($C_1$–$C_4$)alkoxy, ($C_1$–$C_4$) alkylthio, [($C_1$–$C_4$)alkyl]carbonyl and [($C_1$–$C_4$)alkoxy] carbonyl, $R^{10}$ and $R^{11}$ independently of one another are H, ($C_1$–$C_4$) alkyl, ($C_3$–$C_4$)alkenyl or ($C_3$–$C_4$)alkynyl, each of the three latter radicals being unsubstituted or substituted by one or more radicals from the group consisting of halogen, ($C_1$–$C_4$)alkoxy, ($C_1$–$C_4$)alkylthio, [($C_1$–$C_4$) alkyl]carbonyl and [($C_1$–$C_4$)alkoxy]carbonyl, the radicals $R^{12}$ together with the nitrogen atom are a heterocyclic ring having 5 or 6 ring members, which may contain further heteroatoms from the group consisting of N, O and S in the possible oxidation states and is unsubstituted or is substituted by ($C_1$–$C_4$)alkyl or the oxo group, or is benzo-fused, $R^{13}$ is H, ($C_1$–$C_4$)alkyl, ($C_3$–$C_4$)alkenyl or ($C_3$–$C_4$) alkynyl, each of the three latter radicals being unsubstituted or substituted by one or more radicals from the group consisting of halogen, ($C_1$–$C_4$)alkoxy and ($C_1$–$C_4$)alkylthio, A is a radical of the formula

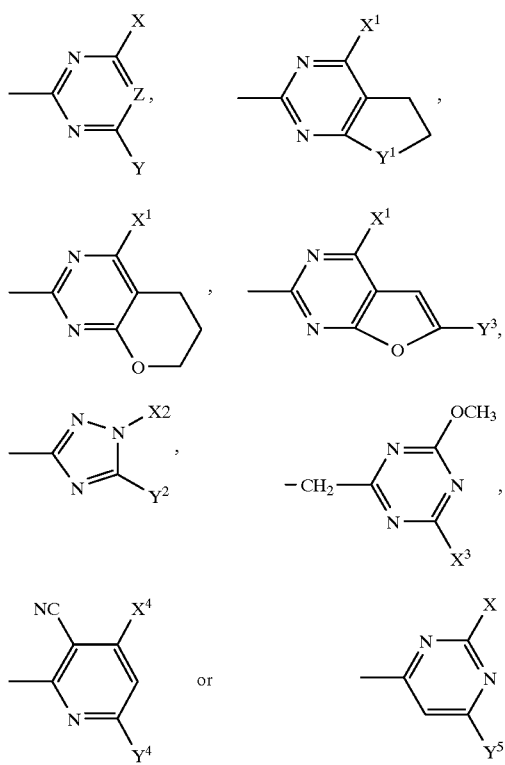

one of the radicals X and Y is hydrogen, halogen, $(C_1–C_3)$ alkyl or $(C_1–C_3)$alkoxy, the two latter radicals being unsubstituted or being mono- or polysubstituted by halogen or monosubstituted by $(C_1–C_3)$alkoxy, and the other of the radicals X and Y is hydrogen, $(C_1–C_3)$ alkyl, $(C_1–C_3)$alkoxy or $(C_1–C_3)$alkylthio, the three latter alkyl-containing radicals being unsubstituted or mono- or polysubstituted by halogen or mono- or disubstituted by $(C_1–C_3)$alkoxy or $(C_1–C_3)$alkylthio, or is a radical of the formula $NR^{14}R^{15}$, $(C_3–C_6)$cycloalkyl, $(C_2–C_4)$alkenyl, $(C_2–C_4)$alkynyl, $(C_3–C_4)$alkenyloxy or $(C_3–C_4)$alkynyloxy, Z is CH or N, $R^{14}$ and $R^{15}$ independently of one another are H, $(C_1–C_3)$ alkyl or $(C_3–C_4)$alkenyl, $X^1$ is $CH_3$, $OCH_3$, $OC_2H_5$ or $OCHF_2$, $Y^1$ is —O— or —$CH_2$—, $X^2$ is $CH_3$, $C_2H_5$ or $CH_2CF_3$, $Y^2$ is $OCH_3$, $OC_2H_5$, $SCH_3$, $SCH_2CH_3$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl, and $Y^5$ is $CH_3$, $C_2H_5$, $OCH_3$ or Cl.

In the formula (I) and below, alkyl, alkoxy, haloalkyl, alkylamino and alkylthio radicals as well as the corresponding unsaturated and/or substituted radicals in the carbon framework may in each case be straight-chain or branched. Alkyl radicals, alone or in composite definitions such as alkoxy, haloalkyl etc., are methyl, ethyl, n- or i-propyl, n-, i-, t- or 2-butyl; alkenyl and 2alkynyl radicals have the definition of the possible unsaturated radicals corresponding to the alkyl radicals, such as 2-propenyl, 2- or 3-butenyl, 2-propynyl, or 2- or 3-butynyl. Halogen is fluorine, chlorine, bromine or iodine; haloalkyl is alkyl which is substituted by one or more atoms from the group consisting of halogen; examples of haloalkyl are $CF_3$, $CHF_2$ and $CH_2CF_3$. Substituted phenyl is advantageously phenyl which is substituted by one or more, preferably 1, 2 or 3, radicals from the group consisting of halogen, such as F, Cl, Br and I, preferably F, Cl and Br, and also alkyl, haloalkyl, alkoxy, haloalkoxy, hydroxyl, amino, nitro, cyano, alkoxycarbonyl, alkylcarbonyl, formyl, carbamoyl, mono- and dialkylaminocarbonyl, mono- and dialkylamino, alkylsulfinyl and alkylsulfonyl, and, for radicals containing carbon atoms, those having from 1 to 4 carbon atoms, especially 1 or 2, are preferred. In this context preference is generally given to substituents from the group consisting of halogen, for example fluorine and chlorine, $C_1–C_4$-alkyl, preferably methyl or ethyl, $C_1–C_4$-haloalkyl, preferably trifluoromethyl, $C_1–C_4$-alkoxy, preferably methoxy or ethoxy, $C_1–C_4$-haloalkoxy, nitro and cyano.

A 5- or 6-membered heterocyclic radical which may if desired be benzo-fused and which contains a nitrogen atom (e.g. in the case of $N(R^{12})_2$) may be a saturated, unsaturated or heteroaromatic radical, for example a radical which is attached via the nitrogen atom and is selected from the group consisting of pyrrolidinyl, piperidyl, pyrazolyl, morpholinyl, indolyl, quinolyl, pyrimidinyl, triazolyl, oxazolyl, pyridyl, pyridazinyl, pyrazinyl, thiazolyl, pyrrolyl, imidazolyl and benzoxazolyl.

The invention also relates to all the stereoisomers encompassed by formula (I), and to mixtures thereof. Such compounds of the formula (I) contain one or more asymmetric carbon atoms or double bonds which are not indicated specifically in the formula (I). Formula (I) encompasses all of the possible stereoisomers defined by their specific spatial orientation such as enantiomers, diastereomers, Z and E isomers, all of which can be prepared by conventional methods from mixtures of the stereoisomers or else by stereoselective reactions in combination with the use of stereochemically pure starting materials.

The compounds of the formula (I) may form salts in which the hydrogen of the —$SO_2$—NH-group is replaced by a cation which is suitable for agriculture. Examples of these salts are metal salts, in particular alkali metal salts or alkaline earth metal salts, especially sodium and potassium salts, or alternatively ammonium salts or salts with organic amines.

Of particular interest are compounds of the formula (I) according to the invention or their salts in which $R^4$ is H, $(C_1–C_4)$alkyl, which is unsubstituted or is substituted by one or more radicals from the group consisting of halogen, $(C_1–C_4)$alkoxy, $(C_1–C_4)$alkylthio, $(C_1–C_4)$alkylsulfonyl, [$(C_1–C_4)$alkoxy]carbonyl and CN, or is $(C_3–C_4)$alkenyl, $(C_3–C_4)$alkynyl, hydroxyl, $(C_1–C_4)$alkoxy, [$(C_1–C_4)$alkyl]carbonyl or $(C_1–C_4)$ alkylsulfonyl, each of the five latter radicals being unsubstituted or substituted in the alkyl moiety by one or more halogen atoms, or is phenylsulfonyl in which the phenyl radical is unsubstituted or is substituted by one or more radicals from the group consisting of halogen, $(C_1–C_4)$alkyl and $(C_1–C_4)$alkoxy, and $R^5$ is $(C_1–C_4)$alkylsulfonyl, $(C_1–C_4)$haloalkylsulfonyl, phenylsulfonyl or phenylcarbonyl, the phenyl radical in the two latter radicals being unsubstituted or substituted by one or more radicals from the group consisting of halogen, $(C_1–C_4)$alkyl and $(C_1–C_4)$alkoxy, or is mono- or di- [$(C_1–C_4)$alkyl]aminosulfonyl, [$(C_1–C_6)$alkyl] carbonyl which is unsubstituted or is substituted by one or more halogen atoms or by $(C_1–C_4)$alkoxy and $(C_1–C_4)$alkylthio, or is formyl, OHC—CO—, 2-oxo-$(C_3–C_5)$alkanoyl, $[(C_1–C_4)$alkoxy]oxalyl, $[(C_3–C_6)$cycloalkyl]carbonyl, $[(C_2–C_4)$alkenyl]carbonyl or $[(C_1–C_4)$alkynyl]carbonyl or is a group of the formula

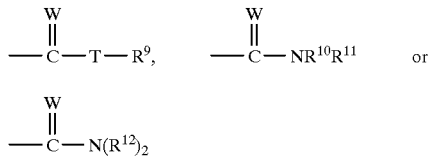

W is O or S, $R^6$ is H, $(C_1–C_4)$alkyl, $(C_1–C_4)$haloalkyl, $(C_1–C_4)$alkoxy, $(C_1–C_4)$haloalkoxy or halogen, $R^8$ is at each occurrence $(C_1–C_4)$alkyl which is unsubstituted or is substituted by one or more halogen atoms, or is $(C_3–C_4)$alkenyl or $(C_3–C_4)$alkynyl, $R^9$ is H, $(C_1–C_4)$alkyl which is unsubstituted or is substituted by one or more halogen atoms or by $(C_1–C_4)$alkoxy, $(C_1–C_4)$alkylthio, $[(C_1–C_4)$alkoxy]carbonyl and $[(C_1–C_4)$alkyl]carbonyl, $R^{10}$ and $R^{11}$ independently of one another are H, $(C_1–C_4)$alkyl which is unsubstituted or is substituted by one or more halogen atoms, or are $(C_3–C_4)$alkenyl or $(C_3–C_4)$alkynyl, at least one of the radicals $R^{10}$ and $R^{11}$ being different from hydrogen, the radicals $R^{12}$ together with the nitrogen atom are a heterocyclic ring having 5 or 6 ring members, which may contain a further heteroatom from the group consisting of N, O and S in the various oxidation states and is unsubstituted or is substituted by $(C_1–C_4)$alkyl or by the oxo group, and $R^{13}$ is at each occurrence H, $(C_1–C_4)$alkyl which is unsubstituted or is substituted by one or more halogen atoms, or is $(C_3–C_4)$alkenyl or $(C_3–C_4)$alkynyl.

Preferred compounds of the formula (I) or their salts are those in which W is an oxygen atom and A is a radical of the formula

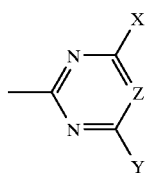

in which X, Y and Z are defined as described above.

Particularly preferred compounds of the formula (I) or their salts are those in which $R^4$ is H, $(C_1–C_4)$alkyl, hydroxyl or $(C_1–C_4)$alkoxy, $R^5$ is $(C_1–C_4)$alkylsulfonyl, CHO, $[(C_1–C_4)$alkyl]carbonyl which is unsubstituted or is substituted by one or more halogen atoms, or is $[(C_1–C_4)$alkoxy]oxalyl, $[(C_1–C_6)$cycloalkyl]carbonyl or a group of the formula

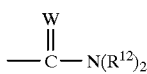

in which

W, T and $R^9$ to $R^{12}$ are as defined above for formula (I), $R^6$ is H, $(C_1–C_3)$alkyl, $(C_1–C_3)$alkoxy or halogen, A is a radical of the formula

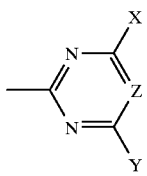

Z is CH or N, preferably CH, and one of the radicals X and Y is halogen, $(C_1–C_2)$alkyl, $(C_1–C_2)$alkoxy, $OCF_2H$, $CF_3$ or $OCH_2CF_3$ and the other of the radicals X and Y is $(C_1–C_2)$alkyl, $(C_1–C_2)$alkoxy or $(C_1–C_2)$haloalkoxy.

For reasons of increased ease of preparation or of better biological action, compounds of the formula (II) according to the invention or their salts in which the group —$CR^2R^3$—$NR^4R^5$ is in the ortho or para position to the group $R^1$ or is in the ortho position to the sulfo group are of particular interest; the preferred position of the group —$CR^2R^3$—$NR^4R^5$ is para to the group $R^1$.

The present invention also relates to processes for the preparation of the compounds of the formula (I) or their salts, which comprise a) reacting a compound of the formula (II)

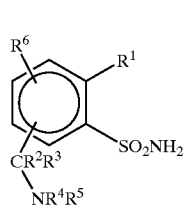

(II)

with a heterocyclic carbamate of the formula (III)

R*—O—CO—NR$^7$—A (III)

in which R* is unsubstituted or substituted phenyl or $(C_1–C_4)$alkyl, or b) reacting a phenyl sulfonylcarbamate of the formula (IV)

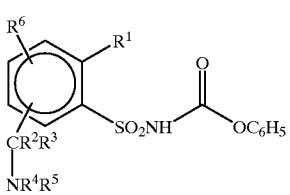

(IV)

with an amino heterocycle of the formula (V)

H—NR$^7$—A (V)

or c) reacting a sulfonyl isocyanate of the formula (VI)

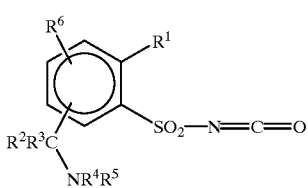

(VI)

with an amino heterocycle of the formula H—NR⁷—A (V), or d) in a one-pot reaction, first reacting an amino heterocycle of the formula H—NR⁷—A (V) with phosgene in the presence of a base and reacting the intermediate formed with a phenyl sulfonamide of the formula (II), or e) reacting a sulfonyl chloride of the formula (VII)

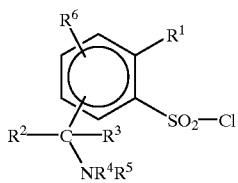

(VII)

with a cyanate M—OCN in which M=NH$_4$, Na or K, and with an amino heterocycle of the formula H—NR⁷—A (V) in the presence of a base, or f) reacting a sulfonamide of the abovementioned formula (II) with a (thio)isocyanate of the formula (V')

$$W=C=N-A \qquad (V')$$

in the presence of a base,
the radicals and groups R$^1$ to R$^7$, A and W in the formulae (II)–(VII) and (V') being as defined for formula (I) and, in variant a)–e), compounds of the formula (I) where W=O being obtained initially.

The reaction of the compounds of the formulae (II) and (III) is preferably carried out base-catalyzed in an inert organic solvent, for example dichloromethane, acetonitrile, dioxane or THF, at temperatures of between 0° C. and the boiling point of the solvent. Examples of the base used are organic amine bases, such as 1,8-diazabicyclo[5.4.0]undec-7-ene (DBU), especially when R*=(substituted) phenyl (cf. EP-A-44 807), or trimethylaluminum or triethylaluminum, the latter especially when R*=alkyl (cf. EP-A-166 516).

The sulfonamides (II) are new compounds. They and their preparation are also subjects of this invention.

Taking as example the compound (II) where R²=R³=H and Q=O, possibilities for preparation are illustrated in more detail below, and with slight modifications can also be employed for compounds where R² and R³ are other than hydrogen and/or Q is other than O.

Starting from substituted or unsubstituted methylaniline-sulfonic acids (VIII) (see German Imperial Patent 48 583, p. 242), which may be initially converted by diazotization and Sandmeyer reaction with KCN/CuCN into the nitriles (IX), the sulfonamide (X) is obtained as intermediate product after hydrolysis of the nitrile, esterification of the carboxyl group and conversion of the sulfo group into the tert-butyl-protected sulfonamide group by analogy with methods known from the literature (see Scheme 1).

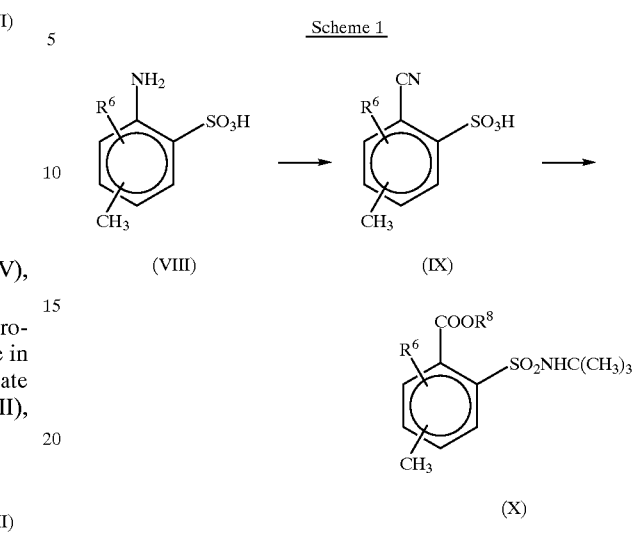

Furthermore, sulfonamides (X) are obtained starting from substituted or unsubstituted methylnitrobenzoic acids (XI) via esterification, reduction of the nitro group, diazotization and coupling with SO$_2$/CuCl (see H. Meerwein et al., Chem. Ber. 90, 841–1178 (1957)) and aminolysis with tert.-butylamine (see Scheme 2).

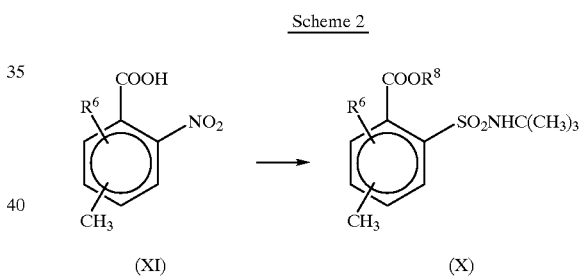

Likewise, sulfonamides (X) can be prepared starting from substituted or unsubstituted methylnitroanilines (XII). Diazotization and coupling with KCN/CuCN give the corresponding nitriles, which can be converted by hydrolysis of the cyano group and esterification into nitrobenzoic esters (XIII).

The nitro group can then as described for Scheme 2 be converted into the tert.-butylaminosulfonyl group (see Scheme 3).

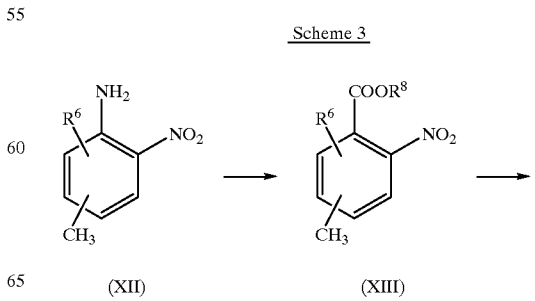

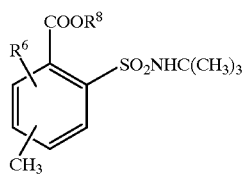

(X)

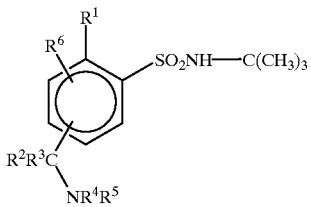

(XV)

For the preparation of the sulfonamides (II) compounds of the formula (X) are reacted by side-chain halogenation to give (XIV), then by substitution of the halogen atom in (XIV) for amines or azide, with subsequent reduction to give benzylamines (XV') and further functionalization of the amino group, and elimination of the tert.-butyl protecting group by analogy with a known procedure (for example with $CF_3COOH$) to give the sulfonamides (II') (see Scheme 4).

Scheme 4

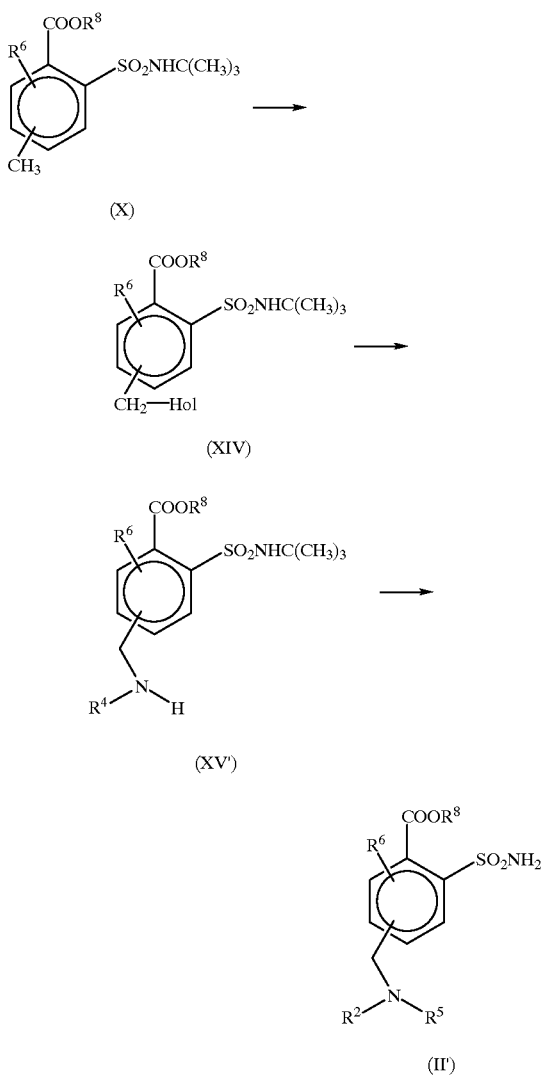

The procedure can also be used analogously to prepare other compounds of the formula (II), employing in the final step the compound of the formula (XV).

The carbamates of the formula (III) can be prepared by methods which are described in South African Patent Applications 82/5671 and 82/5045 or EP-A-70 804 (U.S. Pat. No. 4,480,101) or RD 275 056.

The reaction of the compounds (IV) with the amino heterocycles (V) is preferably carried out in inert aprotic solvents such as dioxane, acetonitrile or tetrahydrofuran at temperatures of between 0° C. and the boiling temperature of the solvent. The required starting materials (V) are known from the literature or can be prepared by processes known from the literature. The phenylsulfonyl carbamates of the formula (IV) are obtained by analogy with U.S. Pat. No. 4,684,393 or U.S. Pat. No. 4,743,290.

The phenylsulfonyl isocyanates of the formula (VI) can be prepared by analogy with U.S. Pat. No. 4,481,029 and can be reacted with amino heterocycles (V).

The phosgenation of compounds of the formula (V) in accordance with variant d) can preferably be carried out in the presence of bases such as sterically hindered organic amine bases, for example triethylamine. The subsequent reaction with compounds of the formula (II) in accordance with variant d) can be carried out by analogy with known methods (cf. EP-A-232 067).

The sulfochlorides (VII) can be obtained from corresponding sulfonic acids by, for example, standard methods such as the reaction of the potassium salt with phosphorus oxychloride or thionyl chloride in inert solvents such as acetonitrile and/or sulfolane or in bulk by heating at reflux (cf. Houben-Weyl-Klamann, "Methoden der organischen Chemie", [Methods of Organic Chemistry], 4th edition, vol. E XI/2, pp. 1067–1073, Thieme Verlag, Stuttgart, 1985).

The corresponding sulfonic acids are obtainable from appropriate nitro compounds by analogy with the reaction of compounds (XI).

Alternatively, in individual cases sulfochlorides (VII) can be prepared by sulfonation (+chlorination) or sulfochlorination of appropriate substituted benzoic esters; sulfochlorination by analogy with Houben-Weyl-Klamann, "Methoden der organischen Chemie" [Methods of Organic Chemistry], 4th edition, vol. E XI/2, pp. 1067ff., Thieme Verlag Stuttgart, 1985; Houben-Weyl-Müller, "Methoden der organischen ChemieII" [Methods of Organic Chemistry], 4th edition, vol. IX, pp. 563ff., Thieme Verlag Stuttgart, 1955; sulfonation by analogy with Houben-Weyl-Klamann, "Methoden der organischen Chemie" [Methods of Organic Chemistry], 4th edition, vol. E XI/2, pp. 1055ff., Thieme Verlag Stuttgart, 1985; Houben-Weyl-Müller, "Methoden der organischen Chemie" [Methods of Organic Chemistry], 4th edition, vol. IX, pp. 435ff., Thieme Verlag Stuttgart, 1955.

The (thio)isocyanates of the formula (V') are obtainable by methods known from the literature (EP-A-232 067, EP-A-166 516). The reaction of the (thio)isocyanates (V') with compounds (II) is carried out at from −10° C. to 100° C., preferably from 20 to 100° C., in an inert aprotic solvent such as acetone or acetonitrile in the presence of a suitable base, for example $N(C_2H_5)_3$ or $K_2CO_3$.

The salts of the compounds of the formula (I) are preferably prepared in inert polar solvents such as water, methanol or acetone at temperatures of 0–100° C. Examples of bases which are suitable for the preparation of the salts according to the invention are alkali metal carbonates such as potassium carbonate, alkali metal hydroxides and alkali earth metal hydroxides, for example NaOH or KOH, or ammonia or ethanolamine.

The inert solvents referred to in the abovementioned process variants are in each case solvents which are inert under the respective reaction conditions, but which are not necessarily inert under any reaction conditions.

The compounds of the formula (I) according to the invention have an excellent herbicidal activity against a broad range of economically important monocotyledon and dicotyledon harmful plants. The active substances also act efficiently on perennial weeds which produce shoots from rhizomes, root stocks or other perennial organs and which are difficult to control. In this context, it does not matter whether the substances are applied before sowing, pre-emergence or post-emergence.

Specifically, examples may be mentioned of some representatives of the monocotyledon and dicotyledon weed flora which can be controlled by the compounds according to the invention, without the mention intending restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention likewise effect outstanding control of weeds which occur under the specific conditions of rice-growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops and, eventually, after three to four weeks have elapsed, they die completely.

If the active substances are applied post-emergence on the green parts of the plants, growth likewise stops drastically a very short time after the treatment and the weed plants remain at the growth stage of the point in time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling unwanted plant growth in agricultural crop plants.

In addition, the substances according to the invention exhibit outstanding growth-regulatory properties in crop plants. They intervene to regulate the plant metabolism and can therefore be employed so as to have a specific influence on substances contained in plants, and for facilitating harvesting, for example by initiating desiccation and growth compression. Furthermore, they are also suitable for the general control and inhibition of unwanted vegetative growth, without killing off the plants in the process. Inhibition of vegetative growth plays an important role in many monocotyledon and dicotyledon crops, since it can reduce or completely prevent lodging.

The compounds according to the invention can be used in the form of wettable powders, emulsifiable concentrates, sprayable solutions, dusting agents or granules in the conventional formulations. The invention therefore also relates to herbicidal and plant growth-regulating compositions comprising compounds of the formula (I).

The compounds of the formula (I) can be formulated in a variety of ways, as predetermined by the biological and/or chemicophysical parameters. The following possibilities are therefore suitable for formulation: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water base, oil-miscible solutions, capsule suspensions (CS), dusting agents (DP), seed-dressing agents, granules for scattering and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example in: Winnacker-Küichler, "Chemische Technologie" [Chemical Technology], Volume 7, C. Hauser Verlag Munich, 4th Ed., 1986; Wade van Valkenburg, "Pesticide Formulations", Marcel Dekker N.Y., 1973; K. Martens, "Spray Drying" Handbook, 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl achenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Combinations with other pesticidally active substances, such as insecticides, acaricides, herbicides, fungicides, and with safeners, fertilizers and/or growth regulators may also be prepared on the basis of these formulations, for example in the form of a ready-to-use formulation or as a tank mix.

Wettable powders are preparations which are uniformly dispersible in water and which, besides the active substance, also contain surfactants of ionic and/or nonionic type (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium ligninsulfonate, sodium 2,2'-dinaphthylmethane-6,6'- disulfonate, sodium dibutylnaphthalenesulfonate, or alternatively sodium oleoylmethyltaurinate, in addition to a diluent or inert substance. The wettable powders are prepared by finely grinding the herbicidal active substances, for example, in conventional apparatus such as hammer mills, blower mills and air-jet mills, and mixing them simultaneously or subsequently with the formulation auxiliaries.

Emulsifiable concentrates are prepared by dissolving the active substance in an organic solvent, for example butanol, cyclohexanone, dimethylformamide, xylene and also higher-boiling aromatic compounds or hydrocarbons or mixtures of the organic solvents, with the addition of one or more surfactants of ionic and/or nonionic type (emulsifiers). Examples of emulsifiers which can be used are: calcium salts of an alkylarylsulfonic acid such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan esters, such as sorbitan fatty acid esters or polyoxyethylene sorbitan esters, such as polyoxyethylene sorbitan fatty esters.

Dusting agents are obtained by grinding the active substance with finely divided solid substances, for example talc or natural clays, such as kaolin, bentonite, pyrophyllite or diatomaceous earth.

Suspension concentrates may be based on water or oil. They can be prepared by, for example, wet grinding using conventional bead mills with the possible addition of surfactants as already mentioned, for example, above for the other types of formulation.

Emulsions, for example oil-in-water emulsions (EW), can be prepared, for example, by means of stirrers, colloid mills and/or static mixers, using aqueous organic solvents and, if desired, surfactants, for example as already listed above for the other types of formulation.

Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

Water-dispersible granules are generally prepared by conventional methods such as spray-drying, fluidized-bed granulation, plate granulation, mixing using high-speed mixers and extrusion without solid inert material. For the preparation of plate, fluidized-bed, extrusion and spray granules, see for example processes in "Spray-Drying Handbook" 3rd edition, 1979, G. Goodwin Ltd., London; J. E. Browning, "Agglomeration", Chemical and Engineering 1967, pages 147 ff; "Perry's Chemical Engineer's Handbook", 5th edition, McGraw-Hill, New York 1973, pp. 8–57.

For further details on the formulation of crop protection compositions see, for example, G. C. Klingman, "Weed Control as a Science", John Wiley and Sons Inc., New York, 1961, pp. 81–96 and J. D. Freyer, S. A. Evans, "Weed Control Handbook", 5th edition, Blackwell Scientific Publications, Oxford, 1968, pp. 101–103.

The agrochemical formulations generally contain from 0.1 to 99% by weight and in particular from 0.1 to 95% by weight of active substance of the formula (I). The concentration of active substance in wettable powders is, for example, about 10 to 90% by weight; the remainder to 100% by weight is composed of conventional formulation components. In the case of emulsifiable concentrates, the concentration of active substance can be about 1 to 90, preferably 5 to 80% by weight. Formulations in the form of dusts contain 1 to 30, usually preferably 5 to 20% by weight of active substance, sprayable solutions about 0.05 to 80, preferably 2 to 50% by weight. In the case of water-dispersible granules, the active substance content depends partly on whether the active compound is liquid or solid and on which granulation auxiliaries, fillers etc. are used. In the case of the water-dispersible granules, the content of active substance is, for example, between 1 and 95% by weight and preferably between 10 and 80% by weight.

In addition, the active substance formulations mentioned contain, if appropriate, the adhesives, wetting agents, dispersants, emulsifiers, penetrants, preservatives, frost protectors and solvents, fillers, carriers and colorants, antifoams, evaporation inhibitors and agents influencing the pH and the visocity which are conventional in each case.

Combination partners which can be employed for the active substances according to the invention in mixed formulations or as a tank mix are, for example, known active substances as described in, for example, Weed Research 26, 441–445 (1986), or "The Pesticide Manual", 9th edition, The British Crop Protection Council, 1990/91, Bracknell, England, and the literature quoted therein. Examples of herbicides known from the literature which can be combined with the compounds of the formula (I) are the following active substances (note: the compounds are either given by their common name in accordance with the International Organization for Standardization (ISO) or by the chemical name, together if appropriate with a common code number): acetochlor; acifluorfen; aclonifen; AKH 7088, i.e. [[[1-[5-[2-chloro-4-(trifluoromethyl)phenoxyl-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate;, chlomethoxyfen; chloramben; chlorazifop-butyl, chlormesulon (ICI-A0051); chlorbromuron; chlorbufam; chlorfenac; chlorflurecolmethyl; chloridazon; chlorimuron ethyl; chlornitrofen; chlorotoluron; chloroxuron; chlorpropham; chlorsulfuron; chlorthaldimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamide (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide;

endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (e.g. ethyl ester, HN-252); etobenzanid (HW 52); fenoprop; fenoxan, fenoxaprop and fenoxaprop-P and esters thereof, e.g. fenoxaprop-P-ethyl and fenoxaprop-ethyl; fenoxydim; fenuron; flamprop-methyl; flazasulfuron; fluazifop and fluazifop-P and esters thereof, e.g. fluazifop-butyl and fluazifop-P-butyl; fluchloralin; flumetsulam; flumeturon; flumiclorac and its esters (e.g. pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosaten; halosulfuron and its esters (e.g. methyl esters, NC-319); haloxyfop and its esters; haloxyfop-P (=R-haloxyfop) and its esters; hexazinone, imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron; methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamin; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (e.g. propargyl ester); quinclorac; quinmerac; quinofop and its ester derivatives, quizalofop and quizalofop-P and their ester derivatives, e.g. quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)-phenyl]-4,5,6,7-tetrahydro-2H-indazole; secbumeton; sethoxydim; siduron; simazine; simetryn; SN 106279, i.e. 2-[[7-[2-chloro-4-(trifluoro-methyl)-phenoxy]-2-naphthalenyl]-oxy]-propanoic acid and its methyl ester; sulfentrazon (FMC-97385, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)-sulfonyl]-1H-1, 2,4-triazol-1-carboxamide; thenylchlor (NSK-850); thiazafluron; thizopyr (Mon-13200); thidiazimin (SN-124085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)-phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, present in commercially available form, are diluted, if appropriate, in a customary manner, for example using water in the case of wettable powders, emulsifiable concentrates, dispersions and water-dispersible granules. Preparations in the form of dusts or granules for soil application and scattering, and also sprayable solutions, are usually not further diluted with other inert substances before use.

The application rate required for the compounds of the formula I varies with the external conditions, such as, inter alia, temperature, humidity, and the nature of the herbicide used. It can vary within wide limits, for example between 0.001 and 10.0 kg/ha or more of active substance; preferably, however, it is between 0.005 and 5 kg/ha.

A. CHEMICAL EXAMPLES

Abbreviations: The percentages and proportions relate to weight unless specified more closely.

i.v.=under reduced pressure h=hour(s)

Example A1

N-tert-Butyl-5-bromomethyl-2-methoxycarbonylbenzenesulfonamide

A solution of 54.8 g (192 mmol) of N-tert-butyl-2-methoxycarbonyl-5-methylbenzenesulfonamide in 420 ml of tetrachloromethane is heated at reflux for 6–8 h under a nitrogen protective-gas atmosphere, following addition of 36 g (202 mmol) of N-bromosuccinimide and 0.5 g of azobisisobutyronitrile (AIBN) with simultaneous irradiation with a daylight lamp. The solution is then filtered and then washed in succession with sodium disulphide solution, sodium hydrogen carbonate solution and water, dried over $Na_2SO_4$ and evaporated to dryness i.v. Crystallization of the residue from diisopropyl ether/ethyl acetate yields 41.9 g (57%) of N-tert-butyl-5-bromomethyl-2-methoxycarbonylbenzenesulfonamide of mp. 88–90 °C.

Example A2

N-tert-Butyl-5-azidomethyl-2-methoxycarbonylbenzenesulfonamide

A solution of 25.5 g (70 mmol) of N-tert-butyl-5-bromomethyl-2-methoxycarbonylbenzenesulfonamide and 5.9 g (90 mmol) of sodium azide in 240 ml of ethanol is heated at reflux for 6 h. The solution is then evaporated to dryness and the residue is extracted with water/ethyl acetate. Digestion of the crude product with diisopropyl ether gives 16.6 g (72.5%) of N-tert-butyl-5-azidomethyl-2-methoxycarbonylbenzenesulfonamide of mp. 63–65° C.

Example A3

N-tert-Butyl-5-aminomethyl-2-methoxycarbonylbenzenesulfonamide 16.3 g (50 mmol) of N-tert-butyl-5-azidomethyl-2-methoxycarbonylbenzenesulfonamide are dissolved in 300 ml of methanol and hydrogenated over Pd/C (5%). The mixture is filtered and evaporated to dryness. The crude product obtained is purified by elution through a silica gel column using ethyl acetate/methanol 4:1. 11.2 g (74%) of N-tert-butyl-5-aminomethyl-2-methoxycarbonylbenzenesulfonamide are obtained as a viscous oil.

¹H NMR (100 MHz, CDCl₃):

δ=1.25 (s, 9H, C(CH₃)₃),
1.80 (bs, 2H, NH₂),
3.95 (s, 3H, OCH₃),
4.00 (s, 2H, Ar—CH₂),
6.20 (bs, 1H, SO₂NH),
7.58 (dd, 1H, Ar—H),
7.80 (d, 1H, Ar—H),
8.10 (dd, 1H, Ar—H).

Example A4
N-tert-Butyl-5-acetamidomethyl-2-methoxycarbonylbenzenesulfonamide 0.63 g (8 mmol) of acetyl chloride dissolved in 10 ml of dichloromethane is added dropwise to a solution, cooled to 0° C., of 2.01 g (6.7 mmol) of N-tert-butyl-5-aminomethyl-2-methoxycarbonylbenzenesulfonamide and 0.93 ml (6.7 mmol) of triethylamine in 30 ml of dichloromethane, and the mixture is then stirred at room temperature for 2 h. The reaction solution is washed with water, dried and evaporated to dryness i.v. 2.1 g (91%) of N-tert-butyl-5-acetamidomethyl-2-methoxycarbonylbenzenesulfonamide are obtained as a viscous oil.

¹H NMR (100 MHz, CDCl₃):

δ=1.25 (s, 9H, C(CH₃)₃),
2.05 (s, 3H, COCH₃),
3.95 (s, 3H, OCH₃),
4.50 (s, 2H, Ar—CH₂),
6.15 (s, 1H, SO₂NH),
6.38 (bt, 1H, NH),
7.47 (dd, 1H, Ar—H),
7.75 (d, 1H, Ar—H),
7.95 (dd, 1H, Ar—H).

Example A5
5-Acetamidomethyl-2-methoxycarbonylbenzenesulfonamide

A solution of 2.09 g (6.1 mmol) of N-tert-butyl-5-acetamidomethyl-2-methoxycarbonylbenzenesulfonamide in 25 ml of trifluoroacetic acid is stirred at room temperature for 14 h and then evaporated to dryness. Crystallization of the residue from ethyl acetate yields 1.33 g (76%) of 5-acetamidomethyl-2-methoxycarbonylbenzenesulfonamide of mp. 173–175° C.

Example A6
N-[4,6-Dimethoxypyrimidin-2-yl)aminocarbonyl]-5-acetamidomethyl-2-methoxycarbonylbenzenesulfonamide 0.69 g (4.54 mmol) of 1,8-diazabicyclo[5.4.0]undec-7-ene (DBU) is added at 0° C. to a suspension of 1.3 g (4.54 mmol) of 5-acetamidomethyl-2-methoxycarbonylbenzenesulfonamide and 1.25 g (4.54 mmol) of N-4,6-dimethoxypyrimidin-2-yl)phenylcarbamate in 20 ml of acetonitrile. After 2 h at room temperature, the mixture is diluted with water and diethyl ether, acidified to pH 1–2 with hydrochloric acid, and the resulting precipitate is filtered off and dried. 1.32 g (62%) of N-[(4,6-dimethoxypyrimidin-2-yl)aminocarbonyl]-5-acetamidomethyl-2-methoxycarbonylbenzenesulfonamide of mp. 149–150° C. are obtained.

The compounds of the formula (I) listed in the following tables 1–4 (W=O, A=pyrimidinyl or triazinyl) are obtained in analogy to Examples A1 to A6. In the tables:

Mp.=melting point in °C.
CN=compound number=example number
Me=methyl=CH₃
Et=ethyl
Bu=n- Bu=n-butyl=n-C₄H₉
Ph=phenyl

TABLE 1

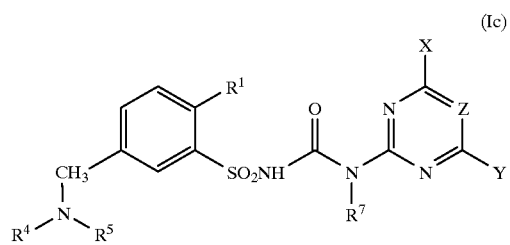

(Ic)

| CN | R¹ | R⁴ | R⁵ | R⁷ | X | Y | Z | Mp. ° C. |
|---|---|---|---|---|---|---|---|---|
| 1 | CO₂CH₃ | H | CHO | H | OCH₃ | OCH₃ | CH | 124–125 |
| 2 | " | " | " | H | OCH₃ | CH₃ | CH | |
| 3 | " | " | " | H | CH₃ | CH₃ | CH | |
| 4 | " | " | " | H | CH₃ | OC₂H₅ | CH | |
| 5 | " | " | " | H | OCH₃ | OCH₃ | N | |
| 6 | " | " | " | H | OCH₃ | CH₃ | N | |
| 7 | " | " | " | H | OCH₃ | Cl | CH | |
| 8 | " | " | " | H | OCF₂H | CH₃ | CH | |
| 9 | " | " | " | H | OCF₂H | OCF₂H | CH | |
| 10 | " | " | " | H | OCH₃ | Br | CH | |
| 11 | " | " | " | H | OCH₃ | OC₂H₅ | CH | |
| 12 | " | " | " | H | OCH₃ | SCH₃ | CH | |
| 13 | " | " | " | H | OCH₃ | OC₂H₅ | N | |
| 14 | " | " | " | H | OCH₃ | OC₃H₇ | CH | |
| 15 | " | " | " | H | CH₃ | Cl | CH | |
| 16 | " | " | " | H | Cl | OC₂H₅ | CH | |
| 17 | " | " | " | H | OC₂H₅ | OC₂H₅ | CH | |
| 18 | " | " | " | H | C₂H₅ | OCH₃ | CH | |

TABLE 1-continued (Ic)

| CN | R¹ | R⁴ | R⁵ | R⁷ | X | Y | Z | Mp. ° C. |
|----|----|----|----|----|---|---|---|----------|
| 19 | " | " | " | H | $CF_3$ | $OCH_3$ | CH | |
| 20 | " | " | " | H | $OCH_2CF_3$ | $CH_3$ | CH | |
| 21 | " | " | " | H | $OCH_2CF_3$ | $OCH_3$ | CH | |
| 22 | " | " | " | H | $OCH_2CF_3$ | $OCH_2CF_3$ | CH | |
| 23 | " | " | " | H | $OCH_2CF_3$ | $OCH_3$ | N | |
| 24 | " | " | " | H | $OCH_3$ | $CH(OCH_3)_2$ | CH | |
| 25 | " | " | " | $CH_3$ | $OCH_3$ | $OCH_3$ | CH | |
| 26 | " | " | " | $CH_3$ | $OCH_3$ | $CH_3$ | N | |
| 27 | " | H | $COCH_3$ | H | $OCH_3$ | $OCH_3$ | CH | 149–150 |
| 28 | " | " | " | H | $OCH_3$ | $CH_3$ | CH | |
| 29 | " | " | " | H | $CH_3$ | $CH_3$ | CH | |
| 30 | " | " | " | H | $CH_3$ | $OC_2H_5$ | CH | |
| 31 | " | " | " | H | $OCH_3$ | $OCH_3$ | N | |
| 32 | " | " | " | H | $OCH_3$ | $CH_3$ | N | |
| 33 | " | " | " | H | $OCH_3$ | Cl | CH | |
| 34 | " | " | " | H | $OCF_2H$ | $CH_3$ | CH | |
| 35 | " | " | " | H | $OCF_2H$ | $OCF_2H$ | CH | |
| 36 | " | " | " | H | $OCH_3$ | Br | CH | |
| 37 | " | " | " | H | $OCH_3$ | $OC_2H_5$ | CH | |
| 38 | " | " | " | H | $OCH_3$ | $SCH_3$ | CH | |
| 39 | " | " | " | H | $OCH_3$ | $OC_2H_5$ | N | |
| 40 | " | " | " | H | $OCH_3$ | $OC_3H_7$ | CH | |
| 41 | " | " | " | H | $CH_3$ | Cl | CH | |
| 42 | " | " | " | H | Cl | $OC_2H_5$ | CH | |
| 43 | " | " | " | H | $OC_2H_5$ | $OC_2H_5$ | CH | |
| 44 | " | " | " | H | $C_2H_5$ | $OCH_3$ | CH | |
| 45 | " | " | " | H | $CF_3$ | $OCH_3$ | CH | |
| 46 | " | " | " | H | $OCH_2CF_3$ | $CH_3$ | CH | |
| 47 | " | " | " | H | $OCH_2CF_3$ | $OCH_3$ | CH | |
| 48 | " | " | " | H | $OCH_2CF_3$ | $OCH_2CF_3$ | CH | |
| 49 | " | " | " | H | $OCH_2CF_3$ | $OCH_3$ | N | |
| 50 | " | " | " | H | $OCH_3$ | $CH(OCH_3)_2$ | CH | |
| 51 | " | " | " | $CH_3$ | $OCH_3$ | $OCH_3$ | CH | |
| 52 | " | " | " | $CH_3$ | $OCH_3$ | $CH_3$ | N | |
| 53 | " | $CH_3$ | CHO | H | $OCH_3$ | $OCH_3$ | CH | 171–175 |
| 54 | " | " | " | H | $OCH_3$ | $CH_3$ | CH | 135–140 |
| 55 | " | " | " | H | $CH_3$ | $CH_3$ | CH | 123–126 |
| 56 | " | " | " | H | $CH_3$ | $OC_2H_5$ | CH | |
| 57 | " | " | " | H | $OCH_3$ | $OCH_3$ | N | |
| 58 | " | " | " | H | $OCH_3$ | $CH_3$ | N | 105 |
| 59 | " | " | " | H | $OCH_3$ | Cl | CH | 125–130 |
| 60 | " | " | " | H | $OCF_2H$ | $CH_3$ | CH | |
| 61 | " | " | " | H | $OCF_2H$ | $OCF_2H$ | CH | |
| 62 | " | " | " | H | $OCH_3$ | Br | CH | |
| 63 | " | " | " | H | $OCH_3$ | $OC_2H_5$ | CH | |
| 64 | " | " | " | H | $OCH_3$ | $SCH_3$ | CH | |
| 65 | " | " | " | H | $OCH_3$ | $OC_2H_5$ | N | |
| 66 | " | " | " | H | $OCH_3$ | $OC_3H_7$ | CH | |
| 67 | " | " | " | H | $CH_3$ | Cl | CH | |
| 68 | " | " | " | H | Cl | $OC_2H_5$ | CH | |
| 69 | " | " | " | H | $OC_2H_5$ | $OC_2H_5$ | CH | |
| 70 | " | " | " | H | $C_2H_5$ | $OCH_3$ | CH | |
| 71 | " | " | " | H | $CF_3$ | $OCH_3$ | CH | |
| 72 | " | " | " | H | $OCH_2CF_3$ | $CH_3$ | CH | |
| 73 | " | " | " | H | $OCH_2CF_3$ | $OCH_3$ | CH | |
| 74 | " | " | " | H | $OCH_2CF_3$ | $OCH_2CF_3$ | CH | |
| 75 | " | " | " | H | $OCH_2CF_3$ | $OCH_3$ | N | |
| 76 | " | " | " | H | $OCH_3$ | $CH(OCH_3)_2$ | CH | |
| 77 | " | " | " | H | $OCH_3$ | $OCH_3$ | CH | |
| 78 | " | " | " | $CH_3$ | $OCH_3$ | $CH_3$ | N | |
| 79 | " | $CH_3$ | $COCH_3$ | H | $OCH_3$ | $OCH_3$ | CH | 146–149 |
| 80 | " | " | " | H | $OCH_3$ | $CH_3$ | CH | |
| 81 | " | " | " | H | $CH_3$ | $CH_3$ | CH | |
| 82 | " | " | " | H | $CH_3$ | $OC_2H_5$ | CH | |

TABLE 1-continued

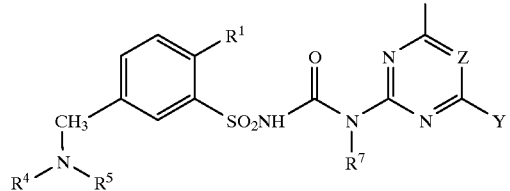

(Ic)

| CN | R¹ | R⁴ | R⁵ | R⁷ | X | Y | Z | Mp. ° C. |
|---|---|---|---|---|---|---|---|---|
| 83 | " | " | " | H | $OCH_3$ | $OCH_3$ | N | |
| 84 | " | " | " | H | $OCH_3$ | $CH_3$ | N | |
| 85 | " | " | " | H | $OCH_3$ | Cl | CH | |
| 86 | " | " | " | H | $OCF_2H$ | $CH_3$ | CH | |
| 87 | " | " | " | H | $OCF_2H$ | $OCF_2H$ | CH | |
| 88 | " | " | " | H | $OCH_3$ | Br | CH | |
| 89 | " | " | " | H | $OCH_3$ | $OC_2H_5$ | CH | |
| 90 | " | " | " | H | $OCH_3$ | $SCH_3$ | CH | |
| 91 | " | " | " | H | $OCH_3$ | $OC_2H_5$ | N | |
| 92 | " | " | " | H | $OCH_3$ | $OC_3H_7$ | CH | |
| 93 | " | " | " | H | $CH_3$ | Cl | CH | |
| 94 | " | " | " | H | Cl | $OC_2H_5$ | CH | |
| 95 | " | " | " | H | $OC_2H_5$ | $OC_2H_5$ | CH | |
| 96 | " | " | " | H | $C_2H_5$ | $OCH_3$ | CH | |
| 97 | " | " | " | H | $CF_3$ | $OCH_3$ | CH | |
| 98 | " | " | " | H | $OCH_2CF_3$ | $CH_3$ | CH | |
| 99 | " | " | " | H | $OCH_2CF_3$ | $OCH_3$ | CH | |
| 100 | " | " | " | H | $OCH_2CF_3$ | $OCH_2CF_3$ | CH | |
| 101 | " | " | " | H | $OCH_2CF_3$ | $OCH_3$ | N | |
| 102 | " | " | " | H | $OCH_3$ | $CH(OCH_3)_2$ | CH | |
| 103 | " | " | " | $CH_3$ | $OCH_3$ | $OCH_3$ | CH | |
| 104 | " | " | " | $CH_3$ | $OCH_3$ | $CH_3$ | N | |
| 105 | " | H | $SO_2CH_3$ | H | $OCH_3$ | $OCH_3$ | CH | 192–194 |
| 106 | " | " | " | H | $OCH_3$ | $CH_3$ | CH | |
| 107 | " | " | " | H | $CH_3$ | $CH_3$ | CH | |
| 108 | " | " | " | H | $OCH_3$ | $OCH_3$ | N | |
| 109 | " | " | " | H | $OCH_3$ | $CH_3$ | N | |
| 110 | " | " | " | H | $OC_2H_5$ | $NHCH_3$ | N | |
| 111 | " | " | " | $CH_3$ | $OCH_3$ | $OCH_3$ | CH | |
| 112 | " | " | " | $CH_3$ | $OCH_3$ | $CH_3$ | N | |
| 113 | " | $CH_3$ | $SO_2CH_3$ | H | $OCH_3$ | $OCH_3$ | CH | 107–109 |
| 114 | " | " | " | H | $OCH_3$ | $CH_3$ | CH | |
| 115 | " | " | " | H | $CH_3$ | $CH_3$ | CH | |
| 116 | " | " | " | H | $OCH_3$ | $OCH_3$ | N | |
| 117 | " | " | " | H | $OCH_3$ | $CH_3$ | N | |
| 118 | " | " | " | H | $OC_2H_5$ | $NHCH_3$ | N | |
| 119 | " | " | " | $CH_3$ | $OCH_3$ | $OCH_3$ | CH | |
| 120 | " | " | " | $CH_3$ | $OCH_3$ | $CH_3$ | N | |
| 121 | " | OH | CHO | H | $OCH_3$ | $OCH_3$ | CH | |
| 122 | " | " | " | H | $OCH_3$ | $CH_3$ | CH | |
| 123 | " | " | " | H | $CH_3$ | $CH_3$ | CH | |
| 124 | " | " | " | H | $OCH_3$ | $OCH_3$ | N | |
| 125 | " | " | " | H | $OCH_3$ | $CH_3$ | N | |
| 126 | " | " | " | H | $OC_2H_5$ | $NHCH_3$ | N | |
| 127 | " | " | " | $CH_3$ | $OCH_3$ | $OCH_3$ | CH | |
| 128 | " | " | " | $CH_3$ | $OCH_3$ | $CH_3$ | N | |
| 129 | " | $OCH_3$ | CHO | H | $OCH_3$ | $OCH_3$ | CH | 142–145 |
| 130 | " | " | " | H | $OCH_3$ | $CH_3$ | CH | |
| 131 | " | " | " | H | $CH_3$ | $CH_3$ | CH | |
| 132 | " | " | " | H | $OCH_3$ | $OCH_3$ | N | |
| 133 | " | " | " | H | $OCH_3$ | $CH_3$ | N | |
| 134 | " | " | " | H | $OC_2H_5$ | $NHCH_3$ | N | |
| 135 | " | " | " | $CH_3$ | $OCH_3$ | $OCH_3$ | CH | |
| 136 | " | " | " | $CH_3$ | $OCH_3$ | $CH_3$ | N | |
| 137 | " | OH | $COCH_3$ | H | $OCH_3$ | $OCH_3$ | CH | |
| 138 | " | " | " | H | $OCH_3$ | $CH_3$ | CH | |
| 139 | " | " | " | H | $CH_3$ | $CH_3$ | CH | |
| 140 | " | " | " | H | $OCH_3$ | $OCH_3$ | N | |
| 141 | " | " | " | H | $OCH_3$ | $CH_3$ | N | |
| 142 | " | " | " | H | $OC_2H_5$ | $NHCH_3$ | N | |
| 143 | " | " | " | $CH_3$ | $OCH_3$ | $OCH_3$ | CH | |
| 144 | " | " | " | $CH_3$ | $OCH_3$ | $CH_3$ | N | |
| 145 | " | $OCH_3$ | $COCH_3$ | H | $OCH_3$ | $OCH_3$ | CH | 195–196 |
| 146 | " | " | " | H | $OCH_3$ | $CH_3$ | CH | |

TABLE 1-continued (Ic)

| CN | R¹ | R⁴ | R⁵ | R⁷ | X | Y | Z | Mp. ° C. |
|---|---|---|---|---|---|---|---|---|
| 147 | " | " | " | H | CH₃ | CH₃ | CH | |
| 148 | " | " | " | H | OCH₃ | OCH₃ | N | |
| 149 | " | " | " | H | OCH₃ | CH₃ | N | |
| 150 | " | " | " | H | OC₂H₅ | NHCH₃ | N | |
| 151 | " | " | " | CH₃ | OCH₃ | OCH₃ | CH | |
| 152 | " | " | " | CH₃ | OCH₃ | CH₃ | N | |
| 153 | " | H | COC₂H₅ | H | OCH₃ | OCH₃ | CH | 105–152 |
| 154 | " | " | " | H | OCH₃ | CH₃ | CH | |
| 155 | " | " | " | H | OCH₃ | OCH₃ | N | |
| 156 | " | " | " | H | OCH₃ | CH₃ | N | |
| 157 | " | CH₃ | " | H | OCH₃ | OCH₃ | CH | |
| 158 | " | " | " | H | OCH₃ | CH₃ | CH | |
| 159 | " | " | " | H | OCH₃ | OCH₃ | N | |
| 160 | " | " | " | H | OCH₃ | CH₃ | N | |
| 161 | " | H | COCH₂OCH₃ | H | OCH₃ | OCH₃ | CH | |
| 162 | " | " | " | H | OCH₃ | CH₃ | CH | |
| 163 | " | " | " | H | OCH₃ | OCH₃ | N | |
| 164 | " | " | " | H | OCH₃ | CH₃ | N | |
| 165 | " | CH₃ | " | H | OCH₃ | OCH₃ | CH | |
| 166 | " | " | " | H | OCH₃ | CH₃ | CH | |
| 167 | " | " | " | H | OCH₃ | OCH₃ | N | |
| 168 | " | " | " | H | OCH₃ | CH₃ | N | |
| 169 | " | H | COCO₂C₂H₅ | H | OCH₃ | OCH₃ | CH | |
| 170 | " | " | " | H | OCH₃ | CH₃ | CH | |
| 171 | " | " | " | H | OCH₃ | OCH₃ | N | |
| 172 | " | " | " | H | OCH₃ | CH₃ | N | |
| 173 | " | CH₃ | " | H | OCH₃ | OCH₃ | CH | |
| 174 | " | " | " | H | OCH₃ | CH₃ | CH | |
| 175 | " | " | " | H | OCH₃ | OCH₃ | N | |
| 176 | " | " | " | H | OCH₃ | CH₃ | N | |
| 177 | " | H | COCF₃ | H | OCH₃ | OCH₃ | CH | 158 |
| 178 | " | " | " | H | OCH₃ | CH₃ | CH | |
| 179 | " | " | " | H | OCH₃ | OCH₃ | N | |
| 180 | " | " | " | H | OCH₃ | CH₃ | N | |
| 181 | " | CH₃ | " | H | OCH₃ | OCH₃ | CH | 144–147 |
| 182 | " | " | " | H | OCH₃ | CH₃ | CH | |
| 183 | " | " | " | H | OCH₃ | OCH₃ | N | |
| 184 | " | " | " | H | OCH₃ | CH₃ | N | |
| 185 | " | H | COOCH₃ | H | OCH₃ | OCH₃ | CH | 160–161 |
| 186 | " | " | " | H | OCH₃ | CH₃ | CH | |
| 187 | " | " | " | H | OCH₃ | OCH₃ | N | |
| 188 | " | " | " | H | OCH₃ | CH₃ | N | |
| 189 | " | CH₃ | " | H | OCH₃ | OCH₃ | CH | 157–159 |
| 190 | " | " | " | H | OCH₃ | CH₃ | CH | |
| 191 | " | " | " | H | OCH₃ | OCH₃ | N | |
| 192 | " | " | " | H | OCH₃ | CH₃ | N | |
| 193 | " | H | CONHC₂H₅ | H | OCH₃ | OCH₃ | CH | |
| 194 | " | " | " | H | OCH₃ | CH₃ | CH | |
| 195 | " | " | " | H | OCH₃ | OCH₃ | N | |
| 196 | " | " | " | H | OCH₃ | CH₃ | N | |
| 197 | " | CH₃ | " | H | OCH₃ | OCH₃ | CH | |
| 198 | " | " | " | H | OCH₃ | CH₃ | CH | |
| 199 | " | " | " | H | OCH₃ | OCH₃ | N | |
| 200 | " | " | " | H | OCH₃ | CH₃ | N | |
| 201 | " | H | CSNHC₂H₅ | H | OCH₃ | OCH₃ | CH | |
| 202 | " | " | " | H | OCH₃ | CH₃ | CH | |
| 203 | " | " | " | H | OCH₃ | OCH₃ | N | |
| 204 | " | " | " | H | OCH₃ | CH₃ | N | |
| 205 | " | CH₃ | " | H | OCH₃ | OCH₃ | CH | |
| 206 | " | " | " | H | OCH₃ | CH₃ | CH | |
| 207 | " | " | " | H | OCH₃ | OCH₃ | N | |
| 208 | " | " | " | H | OCH₃ | CH₃ | N | |
| 209 | " | H | SO₂NHCH₃ | H | OCH₃ | OCH₃ | CH | |
| 210 | " | " | " | H | OCH₃ | CH₃ | CH | |

TABLE 1-continued

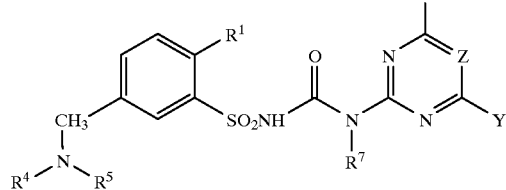

(Ic)

| CN | R¹ | R⁴ | R⁵ | R⁷ | X | Y | Z | Mp. ° C. |
|---|---|---|---|---|---|---|---|---|
| 211 | " | " | " | H | OCH₃ | OCH₃ | N | |
| 212 | " | " | " | H | OCH₃ | CH₃ | N | |
| 213 | " | CH₃ | " | H | OCH₃ | OCH₃ | CH | 171–173 |
| 214 | " | " | " | H | OCH₃ | CH₃ | CH | |
| 215 | " | " | " | H | OCH₃ | OCH₃ | N | |
| 216 | " | " | " | H | OCH₃ | CH₃ | N | |
| 217 | " | H | SO₂N(CH₃)₂ | H | OCH₃ | OCH₃ | CH | 162 |
| 218 | " | " | " | H | OCH₃ | CH₃ | CH | |
| 219 | " | " | " | H | OCH₃ | OCH₃ | N | |
| 220 | " | " | " | H | OCH₃ | CH₃ | N | |
| 221 | " | CH₃ | " | H | OCH₃ | OCH₃ | CH | 127–129 |
| 222 | " | " | " | H | OCH₃ | CH₃ | CH | |
| 223 | " | " | " | H | OCH₃ | OCH₃ | N | |
| 224 | " | " | " | H | OCH₃ | CH₃ | N | |
| 225 | " | —CH₂CH₂CH₂CO— | | H | OCH₃ | OCH₃ | CH | |
| 226 | " | " | | H | OCH₃ | CH₃ | CH | |
| 227 | " | " | | H | OCH₃ | OCH₃ | N | |
| 228 | " | " | | H | OCH₃ | CH₃ | N | |
| 229 | " | —CH₂CH₂CH₂SO₂— | | H | OCH₃ | OCH₃ | CH | |
| 230 | " | " | | H | OCH₃ | CH₃ | CH | |
| 231 | " | " | | H | OCH₃ | OCH₃ | N | |
| 232 | " | " | | H | OCH₃ | CH₃ | N | |
| 233 | " | —CH₂CH₂CH₂CH₂CO— | | H | OCH₃ | OCH₃ | CH | |
| 234 | " | " | | H | OCH₃ | CH₃ | CH | |
| 235 | " | " | | H | OCH₃ | OCH₃ | N | |
| 236 | " | " | | H | OCH₃ | CH₃ | N | |
| 237 | " | —CH₂CH₂CH₂CH₂SO₂— | | H | OCH₃ | OCH₃ | CH | |
| 238 | " | " | | H | OCH₃ | CH₃ | CH | |
| 239 | " | " | | H | OCH₃ | OCH₃ | N | |
| 240 | " | " | | H | OCH₃ | CH₃ | N | |
| 241 | " | —CH₂CH₂OCH₂CH₂— | | H | OCH₃ | OCH₃ | CH | |
| 242 | " | " | | H | OCH₃ | CH₃ | CH | |
| 243 | " | " | | H | OCH₃ | OCH₃ | N | |
| 244 | " | " | | H | OCH₃ | CH₃ | N | |
| 245 | " | H | COC₃H₇ | H | OCH₃ | OCH₃ | CH | |
| 246 | " | " | " | H | OCH₃ | CH₃ | CH | |
| 247 | " | " | " | H | OCH₃ | OCH₃ | N | |
| 248 | " | " | " | H | OCH₃ | CH₃ | N | |
| 249 | " | CH₃ | " | H | OCH₃ | OCH₃ | CH | |
| 250 | " | " | " | H | OCH₃ | CH₃ | CH | |
| 251 | " | " | " | H | OCH₃ | OCH₃ | N | |
| 252 | " | " | " | H | OCH₃ | CH₃ | N | |
| 253 | " | H | COCH₂Cl | H | OCH₃ | OCH₃ | CH | 144–145 |
| 254 | " | " | " | H | OCH₃ | CH₃ | CH | |
| 255 | " | " | " | H | OCH₃ | OCH₃ | N | |
| 256 | " | " | " | H | OCH₃ | CH₃ | N | |
| 257 | " | CH₃ | " | H | OCH₃ | OCH₃ | CH | 138–140 |
| 258 | " | " | " | H | OCH₃ | CH₃ | CH | |
| 259 | " | " | " | H | OCH₃ | OCH₃ | N | |
| 260 | " | " | " | H | OCH₃ | CH₃ | N | |
| 261 | " | H | COCHCl₂ | H | OCH₃ | OCH₃ | CH | |
| 262 | " | " | " | H | OCH₃ | CH₃ | CH | |
| 263 | " | " | " | H | OCH₃ | OCH₃ | N | |
| 264 | " | " | " | H | OCH₃ | CH₃ | N | |
| 265 | " | CH₃ | " | H | OCH₃ | OCH₃ | CH | |
| 266 | " | " | " | H | OCH₃ | CH₃ | CH | |
| 267 | " | " | " | H | OCH₃ | OCH₃ | N | |
| 268 | " | " | " | H | OCH₃ | CH₃ | N | |
| 269 | " | H | COCCl₃ | H | OCH₃ | OCH₃ | CH | |
| 270 | " | " | " | H | OCH₃ | CH₃ | CH | |
| 271 | " | " | " | H | OCH₃ | OCH₃ | N | |
| 272 | " | " | " | H | OCH₃ | CH₃ | N | |
| 273 | " | CH₃ | " | H | OCH₃ | OCH₃ | CH | |
| 274 | " | " | " | H | OCH₃ | CH₃ | CH | |

TABLE 1-continued (Ic)

| CN | R¹ | R⁴ | R⁵ | R⁷ | X | Y | Z | Mp. °C. |
|---|---|---|---|---|---|---|---|---|
| 275 | " | " | " | H | OCH₃ | OCH₃ | N | |
| 276 | " | " | " | H | OCH₃ | CH₃ | N | |
| 277 | " | H | COCH=CH₂ | H | OCH₃ | OCH₃ | CH | |
| 278 | " | " | " | H | OCH₃ | CH₃ | CH | |
| 279 | " | " | " | H | OCH₃ | OCH₃ | N | |
| 280 | " | " | " | H | OCH₃ | CH₃ | N | |
| 281 | " | CH₃ | " | H | OCH₃ | OCH₃ | CH | |
| 282 | " | " | " | H | OCH₃ | CH₃ | CH | |
| 283 | " | " | " | H | OCH₃ | OCH₃ | N | |
| 284 | " | " | " | H | OCH₃ | CH₃ | N | |
| 285 | " | H | COC≡CH | H | OCH₃ | OCH₃ | CH | |
| 286 | " | " | " | H | OCH₃ | CH₃ | CH | |
| 287 | " | " | " | H | OCH₃ | OCH₃ | N | |
| 288 | " | " | " | H | OCH₃ | CH₃ | N | |
| 289 | " | CH₃ | " | H | OCH₃ | OCH₃ | CH | |
| 290 | " | " | " | H | OCH₃ | CH₃ | CH | |
| 291 | " | " | " | H | OCH₃ | OCH₃ | N | |
| 292 | " | " | " | H | OCH₃ | CH₃ | N | |
| 293 | " | H | COC₆H₅ | H | OCH₃ | OCH₃ | CH | |
| 294 | " | " | " | H | OCH₃ | CH₃ | CH | |
| 295 | " | " | " | H | OCH₃ | OCH₃ | N | |
| 296 | " | " | " | H | OCH₃ | CH₃ | N | |
| 297 | " | CH₃ | " | H | OCH₃ | OCH₃ | CH | |
| 298 | " | " | " | H | OCH₃ | CH₃ | CH | |
| 299 | " | " | " | H | OCH₃ | OCH₃ | N | |
| 300 | " | " | " | H | OCH₃ | CH₃ | N | |
| 301 | " | SO₂C₆H₅ | SO₂C₆H₅ | H | OCH₃ | OCH₃ | CH | |
| 302 | " | " | " | H | OCH₃ | CH₃ | CH | |
| 303 | " | " | " | H | OCH₃ | OCH₃ | N | |
| 304 | " | " | " | H | OCH₃ | CH₃ | N | |
| 305 | " | SO₂CH₃ | SO₂CH₃ | H | OCH₃ | OCH₃ | CH | |
| 306 | " | " | " | H | OCH₃ | CH₃ | CH | |
| 307 | " | " | " | H | OCH₃ | OCH₃ | N | |
| 308 | " | " | " | H | OCH₃ | CH₃ | N | |
| 309 | " | H | COCH₂Br | H | OCH₃ | OCH₃ | CH | |
| 310 | " | " | " | H | OCH₃ | CH₃ | N | |
| 311 | " | CH₃ | " | H | OCH₃ | OCH₃ | CH | |
| 312 | " | " | " | H | OCH₃ | CH₃ | N | |
| 313 | " | H | COCH₂F | H | OCH₃ | OCH₃ | CH | |
| 314 | " | " | " | H | OCH₃ | CH₃ | N | |
| 315 | " | CH₃ | " | H | OCH₃ | OCH₃ | CH | |
| 316 | " | " | " | H | OCH₃ | CH₃ | N | |
| 317 | " | H | COCH₂C≡CH | H | OCH₃ | OCH₃ | CH | |
| 318 | " | " | " | H | OCH₃ | CH₃ | N | |
| 319 | " | CH₃ | " | H | OCH₃ | OCH₃ | CH | |
| 320 | " | " | " | H | OCH₃ | CH₃ | N | |
| 321 | " | H | COCO₂CH₃ | H | OCH₃ | OCH₃ | CH | |
| 322 | " | " | " | H | OCH₃ | CH₃ | N | |
| 323 | " | CH₃ | " | H | OCH₃ | OCH₃ | CH | |
| 324 | " | " | " | H | OCH₃ | CH₃ | N | |
| 325 | " | H | CO₂C₂H₅ | H | OCH₃ | OCH₃ | CH | |
| 326 | " | " | " | H | OCH₃ | CH₃ | N | |
| 327 | " | CH₃ | " | H | OCH₃ | OCH₃ | CH | |
| 328 | " | " | " | H | OCH₃ | CH₃ | N | |
| 329 | " | H | COSCH₃— | H | OCH₃ | OCH₃ | CH | |
| 330 | " | " | " | H | OCH₃ | CH₃ | N | |
| 331 | " | CH₃ | " | H | OCH₃ | OCH₃ | CH | |
| 332 | " | " | " | H | OCH₃ | CH₃ | N | |
| 333 | " | H | CSOCH₃ | H | OCH₃ | OCH₃ | CH | |
| 334 | " | " | " | H | OCH₃ | CH₃ | N | |
| 335 | " | CH₃ | " | H | OCH₃ | OCH₃ | CH | |
| 336 | " | " | " | H | OCH₃ | CH₃ | N | |
| 337 | " | H | CSSCH₃ | H | OCH₃ | OCH₃ | CH | |
| 338 | " | " | " | H | OCH₃ | CH₃ | N | |

TABLE 1-continued (Ic)

Structure: Benzene ring with R¹ (ortho to SO₂NH), CH₃ group at 5-position bearing NR⁴R⁵, SO₂NH-CO-N(R⁷)-triazine with X, Y, Z substituents.

| CN | R¹ | R⁴ | R⁵ | R⁷ | X | Y | Z | Mp. ° C. |
|---|---|---|---|---|---|---|---|---|
| 339 | " | CH₃ | " | H | OCH₃ | OCH₃ | CH | |
| 340 | " | " | " | H | OCH₃ | CH₃ | N | |
| 341 | " | H | COCH(CH₃)₂ | H | OCH₃ | OCH₃ | CH | |
| 342 | " | " | " | H | OCH₃ | CH₃ | N | |
| 343 | " | CH₃ | " | H | OCH₃ | OCH₃ | CH | |
| 344 | " | " | " | H | OCH₃ | CH₃ | N | |
| 345 | " | H | COC(CH₃)₃ | H | OCH₃ | OCH₃ | CH | |
| 346 | " | " | " | H | OCH₃ | CH₃ | N | |
| 347 | " | CH₃ | " | H | OCH₃ | OCH₃ | CH | |
| 348 | " | " | " | H | OCH₃ | CH₃ | N | |
| 349 | " | H | CO-Cyclopropyl | H | OCH₃ | OCH₃ | CH | |
| 350 | " | " | " | H | OCH₃ | CH₃ | N | |
| 351 | " | CH₃ | " | H | OCH₃ | OCH₃ | CH | |
| 352 | " | " | " | H | OCH₃ | CH₃ | N | |
| 353 | " | H | CO-Cyclobutyl | H | OCH₃ | OCH₃ | CH | |
| 354 | " | " | " | H | OCH₃ | CH₃ | N | |
| 355 | " | CH₃ | " | H | OCH₃ | OCH₃ | CH | |
| 356 | " | " | " | H | OCH₃ | CH₃ | N | |
| 357 | " | H | CO-Cyclopentyl | H | OCH₃ | OCH₃ | CH | |
| 358 | " | " | " | H | OCH₃ | CH₃ | N | |
| 359 | " | CH₃ | " | H | OCH₃ | OCH₃ | CH | |
| 360 | " | " | " | H | OCH₃ | CH₃ | N | |
| 361 | " | H | CO-Cyclohexyl | H | OCH₃ | OCH₃ | CH | |
| 362 | " | " | " | H | OCH₃ | CH₃ | N | |
| 363 | " | CH₃ | " | H | OCH₃ | OCH₃ | CH | |
| 364 | " | " | " | H | OCH₃ | CH₃ | N | |
| 365 | " | H | CONHCH₂CH₂Cl | H | OCH₃ | OCH₃ | CH | |
| 366 | " | " | " | H | OCH₃ | CH₃ | N | |
| 367 | " | CH₃ | " | H | OCH₃ | OCH₃ | CH | |
| 368 | " | " | " | H | OCH₃ | CH₃ | N | |
| 369 | " | H | CSNHCH₂CH₂Cl | H | OCH₃ | OCH₃ | CH | |
| 370 | " | " | " | H | OCH₃ | CH₃ | N | |
| 371 | " | CH₃ | " | H | OCH₃ | OCH₃ | CH | |
| 372 | " | " | " | H | OCH₃ | CH₃ | N | |
| 373 | " | H | CONH-n-C₄H₉ | H | OCH₃ | OCH₃ | CH | |
| 374 | " | " | " | H | OCH₃ | CH₃ | N | |
| 375 | " | CH₃ | " | H | OCH₃ | OCH₃ | CH | |
| 376 | " | " | " | H | OCH₃ | CH₃ | N | |
| 377 | " | H | CSNHCH₃ | H | OCH₃ | OCH₃ | CH | |
| 378 | " | " | " | H | OCH₃ | CH₃ | N | |
| 379 | " | CH₃ | " | H | OCH₃ | OCH₃ | CH | |
| 380 | " | " | " | H | OCH₃ | CH₃ | N | |
| 381 | " | H | CSNHCH₂CH=CH₂ | H | OCH₃ | OCH₃ | CH | |
| 382 | " | " | " | H | OCH₃ | CH₃ | N | |
| 383 | " | CH₃ | " | H | OCH₃ | OCH₃ | CH | |
| 384 | " | " | " | H | OCH₃ | CH₃ | N | |
| 385 | " | CH₃ | CSNHCH₂COCH₃ | H | OCH₃ | OCH₃ | CH | |
| 386 | " | " | " | H | OCH₃ | CH₃ | N | |
| 387 | " | CH₃ | CSNHCH₂COC₂H₅ | H | OCH₃ | OCH₃ | CH | |
| 388 | " | " | " | H | OCH₃ | CH₃ | N | |
| 389 | " | CH₃ | CONHCH₂COCH₃ | H | OCH₃ | OCH₃ | CH | |
| 390 | " | " | " | H | OCH₃ | CH₃ | N | |
| 391 | " | CH₃ | CONHCH₂COC₂H₅ | H | OCH₃ | OCH₃ | CH | |
| 392 | " | " | " | H | OCH₃ | CH₃ | N | |
| 393 | " | | —CONHCH₂CO— | H | OCH₃ | OCH₃ | CH | |
| 394 | " | | " | H | OCH₃ | CH₃ | N | |
| 395 | " | H | SO₂CH₂F | H | OCH₃ | OCH₃ | CH | |
| 396 | " | " | " | H | OCH₃ | CH₃ | N | |
| 397 | " | CH₃ | " | H | OCH₃ | OCH₃ | CH | |
| 398 | " | " | " | H | OCH₃ | CH₃ | N | |
| 399 | " | H | SO₂CF₃ | H | OCH₃ | OCH₃ | CH | |
| 400 | " | " | " | H | OCH₃ | CH₃ | N | |
| 401 | " | CH₃ | " | H | OCH₃ | OCH₃ | CH | |
| 402 | " | " | " | H | OCH₃ | CH₃ | N | |

TABLE 1-continued

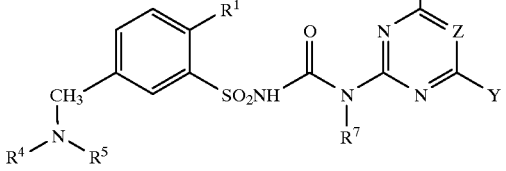

(Ic)

| CN | R¹ | R⁴ | R⁵ | R⁷ | X | Y | Z | Mp. ° C. |
|---|---|---|---|---|---|---|---|---|
| 403 | " | H | SO₂C₂H₅ | H | OCH₃ | OCH₃ | CH | |
| 404 | " | " | " | H | OCH₃ | CH₃ | N | |
| 405 | " | CH₃ | " | H | OCH₃ | OCH₃ | CH | |
| 406 | " | " | " | H | OCH₃ | CH₃ | N | |
| 407 | " | H | SO₂-n-C₃H₇ | H | OCH₃ | OCH₃ | CH | |
| 408 | " | " | " | H | OCH₃ | CH₃ | N | |
| 409 | " | CH₃ | " | H | OCH₃ | OCH₃ | CH | |
| 410 | " | " | " | H | OCH₃ | CH₃ | N | |
| 411 | " | OH | COC₂H₅ | H | OCH₃ | OCH₃ | CH | |
| 412 | " | " | " | H | OCH₃ | CH₃ | N | |
| 413 | " | OCH₃ | " | H | OCH₃ | OCH₃ | CH | |
| 414 | " | " | " | H | OCH₃ | CH₃ | N | |
| 415 | " | OH | COCH₂Cl | H | OCH₃ | OCH₃ | CH | |
| 416 | " | " | " | H | OCH₃ | CH₃ | N | |
| 417 | " | OCH₃ | " | H | OCH₃ | OCH₃ | CH | |
| 418 | " | " | " | H | OCH₃ | CH₃ | N | |
| 419 | " | OH | COCF₃ | H | OCH₃ | OCH₃ | CH | |
| 420 | " | " | " | H | OCH₃ | CH₃ | N | |
| 421 | " | OCH₃ | " | H | OCH₃ | OCH₃ | CH | 159–161 |
| 422 | " | " | " | H | OCH₃ | CH₃ | N | |
| 423 | " | OH | COCH₂OCH₃ | H | OCH₃ | OCH₃ | CH | |
| 424 | " | " | " | H | OCH₃ | CH₃ | N | |
| 425 | " | OCH₃ | " | H | OCH₃ | OCH₃ | CH | 130–131 |
| 426 | " | " | " | H | OCH₃ | CH₃ | N | |
| 427 | " | OH | COCO₂C₂H₅ | H | OCH₃ | OCH₃ | CH | |
| 428 | " | " | " | H | OCH₃ | CH₃ | N | |
| 429 | " | OCH₃ | " | H | OCH₃ | OCH₃ | CH | 158–159 |
| 430 | " | " | " | H | OCH₃ | CH₃ | N | |
| 431 | " | OH | COOCH₃ | H | OCH₃ | OCH₃ | CH | |
| 432 | " | " | " | H | OCH₃ | CH₃ | N | |
| 433 | " | OCH₃ | " | H | OCH₃ | OCH₃ | CH | 137–138 |
| 434 | " | " | " | H | OCH₃ | CH₃ | N | |
| 435 | " | OH | Cyclopropyl | H | OCH₃ | OCH₃ | CH | |
| 436 | " | " | " | H | OCH₃ | CH₃ | N | |
| 437 | " | OCH₃ | " | H | OCH₃ | OCH₃ | CH | 118–120 |
| 438 | " | " | " | H | OCH₃ | CH₃ | N | |
| 439 | " | OH | COC₆H₅ | H | OCH₃ | OCH₃ | CH | |
| 440 | " | " | " | H | OCH₃ | CH₃ | N | |
| 441 | " | OCH₃ | " | H | OCH₃ | OCH₃ | CH | |
| 442 | " | " | " | H | OCH₃ | CH₃ | N | |
| 443 | " | OH | COCH(CH₃)₂ | H | OCH₃ | OCH₃ | CH | |
| 444 | " | " | " | H | OCH₃ | CH₃ | N | |
| 445 | " | OCH₃ | " | H | OCH₃ | OCH₃ | CH | 126–128 |
| 446 | " | " | " | H | OCH₃ | CH₃ | N | |
| 447 | " | OH | COCH=CH₂ | H | OCH₃ | OCH₃ | CH | |
| 448 | " | " | " | H | OCH₃ | CH₃ | N | |
| 449 | " | OCH₃ | " | H | OCH₃ | OCH₃ | CH | |
| 450 | " | " | " | H | OCH₃ | CH₃ | N | |
| 451 | " | OH | COC≡CH | H | OCH₃ | OCH₃ | CH | |
| 452 | " | " | " | H | OCH₃ | CH₃ | N | |
| 453 | " | OCH₃ | " | H | OCH₃ | OCH₃ | CH | |
| 454 | " | " | " | H | OCH₃ | CH₃ | N | |
| 455 | " | OH | SO₂CH₃ | H | OCH₃ | OCH₃ | CH | |
| 456 | " | " | " | H | OCH₃ | CH₃ | N | |
| 457 | " | OCH₃ | " | H | OCH₃ | OCH₃ | CH | 146–148 |
| 458 | " | " | " | H | OCH₃ | CH₃ | N | |
| 459 | " | OH | SO₂NHCH₃ | H | OCH₃ | OCH₃ | CH | |
| 460 | " | " | " | H | OCH₃ | CH₃ | N | |
| 461 | " | OCH₃ | " | H | OCH₃ | OCH₃ | CH | 179–180 |
| 462 | " | " | " | H | OCH₃ | CH₃ | N | |
| 463 | " | OH | SO₂N(CH₃)₂ | H | OCH₃ | OCH₃ | CH | |
| 464 | " | " | " | H | OCH₃ | CH₃ | N | |
| 465 | " | OCH₃ | " | H | OCH₃ | OCH₃ | CH | 179–180 |
| 466 | " | " | " | H | OCH₃ | CH₃ | N | |

TABLE 1-continued (Ic)

| CN | R¹ | R⁴ | R⁵ | R⁷ | X | Y | Z | Mp. ° C. |
|---|---|---|---|---|---|---|---|---|
| 467 | " | C₂H₅ | CHO | H | OCH₃ | OCH₃ | CH | 168–170 |
| 468 | " | " | " | H | OCH₃ | CH₃ | N | |
| 469 | " | " | COCH₃ | H | OCH₃ | OCH₃ | CH | |
| 470 | " | " | " | H | OCH₃ | CH₃ | N | |
| 471 | " | " | Cyclopropyl | H | OCH₃ | OCH₃ | CH | |
| 472 | " | " | " | H | OCH₃ | CH₃ | N | |
| 473 | " | " | COCH₂Cl | H | OCH₃ | OCH₃ | CH | |
| 474 | " | " | " | H | OCH₃ | CH₃ | N | |
| 475 | " | " | COCF₃ | H | OCH₃ | OCH₃ | CH | |
| 476 | " | " | " | H | OCH₃ | CH₃ | N | |
| 477 | " | " | COOCH₃ | H | OCH₃ | OCH₃ | CH | |
| 478 | " | " | " | H | OCH₃ | CH₃ | N | |
| 479 | " | " | COC₆H₅ | H | OCH₃ | OCH₃ | CH | |
| 480 | " | " | " | H | OCH₃ | CH₃ | N | |
| 481 | " | " | CONHC₂H₅ | H | OCH₃ | OCH₃ | CH | |
| 482 | " | " | " | H | OCH₃ | CH₃ | N | |
| 483 | " | " | CSNHC₂H₅ | H | OCH₃ | OCH₃ | CH | |
| 484 | " | " | " | H | OCH₃ | CH₃ | N | |
| 485 | " | " | SO₂CH₃ | H | OCH₃ | OCH₃ | CH | 154–155 |
| 486 | " | " | " | H | OCH₃ | CH₃ | N | |
| 487 | " | " | SO₂NHCH₃ | H | OCH₃ | OCH₃ | CH | 150–152 |
| 488 | " | " | " | H | OCH₃ | CH₃ | N | |
| 489 | " | " | SO₂N(CH₃)₂ | H | OCH₃ | OCH₃ | CH | |
| 490 | " | " | " | H | OCH₃ | CH₃ | N | |
| 491 | " | " | SO₂C₆H₅ | H | OCH₃ | OCH₃ | CH | |
| 492 | " | " | " | H | OCH₃ | CH₃ | N | |
| 493 | CO₂C₂H₅ | H | CHO | H | OCH₃ | OCH₃ | CH | |
| 494 | " | " | " | H | OCH₃ | CH₃ | N | |
| 495 | " | " | COCH₃ | H | OCH₃ | OCH₃ | CH | |
| 496 | " | " | " | H | OCH₃ | CH₃ | N | |
| 497 | " | " | SO₂CH₃ | H | OCH₃ | OCH₃ | CH | |
| 498 | " | " | " | H | OCH₃ | CH₃ | N | |
| 499 | " | CH₃ | CHO | H | OCH₃ | OCH₃ | CH | |
| 500 | " | " | " | H | OCH₃ | CH₃ | N | |
| 501 | " | " | COCH₃ | H | OCH₃ | OCH₃ | CH | |
| 502 | " | " | " | H | OCH₃ | CH₃ | N | |
| 503 | " | " | SO₂CH₃ | H | OCH₃ | OCH₃ | CH | |
| 504 | " | " | " | H | OCH₃ | CH₃ | N | |
| 505 | " | C₂H₅ | CHO | H | OCH₃ | OCH₃ | CH | |
| 506 | " | " | " | H | OCH₃ | CH₃ | N | |
| 507 | " | " | COCH₃ | H | OCH₃ | OCH₃ | CH | |
| 508 | " | " | " | H | OCH₃ | CH₃ | N | |
| 509 | " | " | SO₂CH₃ | H | OCH₃ | OCH₃ | CH | |
| 510 | " | " | " | H | OCH₃ | CH₃ | N | |
| 511 | " | OH | CHO | H | OCH₃ | OCH₃ | CH | |
| 512 | " | " | " | H | OCH₃ | CH₃ | N | |
| 513 | " | " | COCH₃ | H | OCH₃ | OCH₃ | CH | |
| 514 | " | " | " | H | OCH₃ | CH₃ | N | |
| 515 | " | " | SO₂CH₃ | H | OCH₃ | OCH₃ | CH | |
| 516 | " | " | " | H | OCH₃ | CH₃ | N | |
| 517 | " | OCH₃ | CHO | H | OCH₃ | OCH₃ | CH | |
| 518 | " | " | " | H | OCH₃ | CH₃ | N | |
| 519 | " | " | COCH₃ | H | OCH₃ | OCH₃ | CH | |
| 520 | " | " | " | H | OCH₃ | CH₃ | N | |
| 521 | CO₂-n-Bu | H | CHO | H | OCH₃ | OCH₃ | CH | |
| 522 | CON(CH₃)₂ | CH₃ | CHO | H | OCH₃ | CH₃ | N | |
| 523 | CONHCH₃ | H | CHO | H | OCH₃ | OCH₃ | CH | |
| 524 | COSCH₃ | CH₃ | COCH₃ | H | OCH₃ | CH₃ | N | |
| 525 | CO₂CH₃ | n-Bu | CHO | H | OCH₃ | OCH₃ | CH | |
| 526 | " | " | " | H | OCH₃ | CH₃ | N | |
| 527 | " | H | " | H | OCH₂CF₃ | N(CH₃)₂ | N | |
| 528 | " | CH₃ | " | H | " | " | N | |
| 529 | " | H | COCH₃ | H | " | " | " | |
| 530 | " | CH₃ | " | H | " | " | " | |

TABLE 1-continued (Ic)

Structure: benzene ring with R¹ (ortho to SO₂NH), CH(CH₃)-N(R⁴)(R⁵) substituent, connected via SO₂NH-CO-N(R⁷)- to a triazine bearing X, Y, Z.

| CN | R¹ | R⁴ | R⁵ | R⁷ | X | Y | Z | Mp. ° C. |
|---|---|---|---|---|---|---|---|---|
| 531 | " | " | SO₂CH₃ | H | OCH₃ | OCH₃ | CH | |
| 532 | " | " | " | H | OCH₃ | CH₃ | N | |
| 533 | CO₂CH₃ | \multicolumn{2}{CH₃-C(CH₃)=CH-CH=C(CH₃)-CH₃ group (across R⁴/R⁵)} | H | OCH₃ | OCH₃ | CH | |
| 534 | " | \multicolumn{2}{CH₃-C(CH₃)=CH-CH=C(CH₃)-CH₃ group} | H | OCH₃ | CH₃ | N | |
| 535 | CO₂CH₃ | CH₃ | CHO | H | OCH₃ | OCH₃ | CH | Na-Salt: 236–238 |
| 536 | CO₂CH₃ | H | SO₂CH₃ | H | OCH₃ | OCH₃ | CH | Na-Salt: 170–173 |
| 537 | CO₂CH₃ | CH₃ | SO₂CH₃ | H | OCH₃ | OCH₃ | CH | Na-Salt: 191 |
| 538 | CO₂CH₃ | OCH₃ | CHO | H | OCH₃ | OCH₃ | CH | Na-Salt: 215–216 |
| 539 | CO₂CH₃ | OCH₃ | COCH₃ | H | OCH₃ | OCH₃ | CH | Na-Salt: 224–225 |
| 540 | CO₂CH₃ | H | COOCH₃ | H | OCH₃ | OCH₃ | CH | Na-Salt: 203–205 |
| 541 | CO₂CH₃ | CH₃ | SO₂N(CH₃)₂ | H | OCH₃ | OCH₃ | CH | Na-Salt: 122 |
| 542 | CO₂CH₃ | CH₃ | CONHEt | H | OCH₃ | OCH₃ | CH | Na-Salt: 190–192 |
| 543 | CO₂CH₃ | CH₃ | CONHEt | H | OCH₃ | OCH₃ | CH | 150–152 |
| 544 | CO₂CH₃ | CH₃ | CONHEt | H | OCH₃ | CH₃ | N | |
| 545 | CO₂CH₃ | H | CONHEt | H | OCH₃ | OCH₃ | CH | |
| 546 | CO₂CH₃ | H | CONHEt | H | OCH₃ | CH₃ | N | |
| 547 | CO₂CH₃ | —CO—CH₂CH₂—CO— | | H | OCH₃ | OCH₃ | CH | 220–221 |
| 548 | CO₂CH₃ | —CO—CH₂CH₂—CO— | | H | OCH₃ | OCH₃ | N | |
| 549 | CO₂CH₃ | —CO—CH₂CH₂—CO— | | H | OCH₃ | CH₃ | CH | |
| 550 | CO₂CH₃ | —CO—CH₂CH₂—CO— | | H | OCH₃ | CH₃ | N | |
| 551 | CO₂CH₃ | —CO—CH₂CH₂—CO— | | H | OCH₃ | OCH₃ | CH | Na-Salt: 210–212 |
| 552 | CO₂CH₃ | OCH₃ | COCF₃ | H | OCH₃ | OCH₃ | CH | Na-Salt: 228–229 |
| 553 | CO₂CH₃ | OCH₃ | COOCH₃ | H | OCH₃ | OCH₃ | CH | Na-Salt: 184–185 |
| 554 | CO₂CH₃ | OCH₃ | Cyclopropyl | H | OCH₃ | OCH₃ | CH | Na-Salt: 216 |
| 555 | CO₂CH₃ | OCH₃ | SO₂CH₃ | H | OCH₃ | OCH₃ | CH | Na-Salt: 183–185 |
| 556 | CO₂CH₃ | C₂H₅ | CHO | H | OCH₃ | OCH₃ | CH | Na-Salt: 237–239 |
| 557 | CO₂CH₃ | C₂H₅ | Cyclopropyl | H | OCH₃ | OCH₃ | CH | Na-Salt: 178–180 |
| 558 | CO₂CH₃ | C₂H₅ | COCCl₃ | H | OCH₃ | OCH₃ | CH | 109–111 |
| 559 | CO₂CH₃ | C₂H₅ | COCCl₃ | H | OCH₃ | OCH₃ | CH | Na-Salt: 174–176 |
| 560 | CO₂CH₃ | C₂H₅ | COCCl₃ | H | OCH₃ | CH₃ | N | |
| 561 | CO₂CH₃ | C₂H₅ | COCOOCH₃ | H | OCH₃ | CH₃ | N | |
| 562 | CO₂CH₃ | C₂H₅ | COCOOCH₃ | H | OCH₃ | OCH₃ | CH | 138–140 |
| 563 | CO₂CH₃ | C₂H₅ | COCH₂OCH₃ | H | OCH₃ | OCH₃ | CH | 121–123 |

TABLE 1-continued (Ic) Structure: benzene ring with R¹ and CH₂-NR⁴R⁵ substituents, connected via SO₂NH-C(O)-N(R⁷)- to a triazine with X, Y, Z substituents.

| CN | R¹ | R⁴ | R⁵ | R⁷ | X | Y | Z | Mp. °C. |
|---|---|---|---|---|---|---|---|---|
| 564 | CO₂CH₃ | C₂H₅ | COCH₂OCH₃ | H | OCH₃ | CH₃ | N | |
| 565 | CO₂CH₃ | C₂H₅ | SO₂CH₃ | H | OCH₃ | OCH₃ | CH | 154–155 |
| 566 | CO₂CH₃ | C₂H₅ | SO₂CH₃ | H | OCH₃ | OCH₃ | CH | Na-Salt: 161 |
| 567 | CO₂CH₃ | C₂H₅ | SO₂NHCH₃ | H | OCH₃ | OCH₃ | CH | 150–152 |
| 568 | CO₂CH₃ | C₂H₅ | SO₂NHCH₃ | H | OCH₃ | OCH₃ | CH | Na-Salt: 165–168 |
| 569 | CO₂CH₃ | OC₂H₅ | SO₂CH₃ | H | OCH₃ | OCH₃ | CH | 163–164 |
| 570 | CO₂CH₃ | OC₂H₅ | SO₂CH₃ | H | OCH₃ | OCH₃ | CH | Na-Salt: 166–168 |
| 571 | CO₂CH₃ | OC₂H₅ | CHO | H | OCH₃ | OCH₃ | CH | 165–166 |
| 572 | CO₂CH₃ | OC₂H₅ | CHO | H | OCH₃ | OCH₃ | CH | Na-Salt: 207–208 |
| 573 | CO₂CH₃ | OCH₃ | CONHPh | H | OCH₃ | OCH₃ | CH | 178–179 |
| 574 | CO₂CH₃ | OCH₃ | CONHEt | H | OCH₃ | OCH₃ | CH | 155–157 |
| 575 | CO₂CH₃ | OCH₃ | COCCl₃ | H | OCH₃ | OCH₃ | CH | 165–168 |
| 576 | CO₂CH₃ | OCH₃ | COCCl₃ | H | OCH₃ | OCH₃ | CH | Na-Salt: 100 |
| 577 | CO₂CH₃ | OCH₃ | COCHCl₂ | H | OCH₃ | OCH₃ | CH | 145–150 |
| 578 | CO₂CH₃ | OCH₃ | COCHCl₂ | H | OCH₃ | OCH₃ | CH | Na-Salt: 235 |

TABLE 2

(1b) Structure: benzene ring with R¹ and CH₂-NR⁴R⁵ substituents, connected via SO₂NH-C(O)-N(R⁷)- to a triazine with X, Y, Z substituents.

| CN | R¹ | R⁴ | R⁵ | R⁷ | X | Y | Z | Mp. °C. |
|---|---|---|---|---|---|---|---|---|
| 1 | CO₂CH₃ | H | CHO | H | OCH₃ | OCH₃ | CH | 142–144 |
| 2 | " | " | " | H | OCH₃ | CH₃ | CH | |
| 3 | " | " | " | H | CH₃ | CH₃ | CH | |
| 4 | " | " | " | H | CH₃ | OC₂H₅ | CH | |
| 5 | " | " | " | H | OCH₃ | OCH₃ | N | |
| 6 | " | " | " | H | OCH₃ | CH₃ | N | |
| 7 | " | " | " | H | OCH₃ | Cl | CH | |
| 8 | " | " | " | H | OCF₂H | CH₃ | CH | |
| 9 | " | " | " | H | OCF₂H | OCF₂H | CH | |
| 10 | " | " | " | H | OCH₃ | Br | CH | |
| 11 | " | " | " | H | OCH₃ | OC₂H₅ | CH | |
| 12 | " | " | " | H | OCH₃ | SCH₃ | CH | |
| 13 | " | " | " | H | OCH₃ | OC₂H₅ | N | |
| 14 | " | " | " | H | OCH₃ | OC₃H₇ | CH | |
| 15 | " | " | " | H | CH₃ | Cl | CH | |
| 16 | " | " | " | H | Cl | OC₂H₅ | CH | |
| 17 | " | " | " | H | OC₂H₆ | OC₂H₅ | CH | |
| 18 | " | " | " | H | C₂H₅ | OCH₃ | CH | |
| 19 | " | " | " | H | CF₃ | OCH₃ | CH | |
| 20 | " | " | " | H | OCH₂CF₃ | CH₃ | CH | |
| 21 | " | " | " | H | OCH₂CF₃ | OCH₃ | CH | |
| 22 | " | " | " | H | OCH₂CF₃ | OCH₂CF₃ | CH | |
| 23 | " | " | " | H | OCH₂CF₃ | OCH₃ | N | |
| 24 | " | " | " | H | OCH₃ | CH(OCH₃)₂ | CH | |

TABLE 2-continued (1b)

| CN | R¹ | R⁴ | R⁵ | R⁷ | X | Y | Z | Mp. °C. |
|---|---|---|---|---|---|---|---|---|
| 25 | " | " | " | CH₃ | OCH₃ | OCH₃ | CH | |
| 26 | " | " | " | CH₃ | OCH₃ | CH₃ | N | |
| 27 | " | H | COCH₃ | H | OCH₃ | OCH₃ | CH | 167–169 |
| 28 | " | " | " | H | OCH₃ | CH₃ | CH | |
| 29 | " | " | " | H | CH₃ | CH₃ | CH | |
| 30 | " | " | " | H | CH₃ | OC₂H₅ | CH | |
| 31 | " | " | " | H | OCH₃ | OCH₃ | N | |
| 32 | " | " | " | H | OCH₃ | CH₃ | N | |
| 33 | " | " | " | H | OCH₃ | Cl | CH | |
| 34 | " | " | " | H | OCF₂H | CH₃ | CH | |
| 35 | " | " | " | H | OCF₂H | OCF₂H | CH | |
| 36 | " | " | " | H | OCH₃ | Br | CH | |
| 37 | " | " | " | H | OCH₃ | OC₂H₅ | CH | |
| 38 | " | " | " | H | OCH₃ | SCH₃ | CH | |
| 39 | " | " | " | H | OCH₃ | OC₂H₅ | N | |
| 40 | " | " | " | H | OCH₃ | OC₃H₇ | CH | |
| 41 | " | " | " | H | CH₃ | Cl | CH | |
| 42 | " | " | " | H | Cl | OC₂H₅ | CH | |
| 43 | " | " | " | H | OC₂H₅ | OC₂H₅ | CH | |
| 44 | " | " | " | H | C₂H₅ | OCH₃ | CH | |
| 45 | " | " | " | H | CF₃ | OCH₃ | CH | |
| 46 | " | " | " | H | OCH₂CF₃ | CH₃ | CH | |
| 47 | " | " | " | H | OCH₂CF₃ | OCH₃ | CH | |
| 48 | " | " | " | H | OCH₂CF₃ | OCH₂CF₃ | CH | |
| 49 | " | " | " | H | OCH₂CF₃ | OCH₃ | N | |
| 50 | " | " | " | H | OCH₃ | CH(OCH₃)₂ | CH | |
| 51 | " | " | " | CH₃ | OCH₃ | OCH₃ | CH | |
| 52 | " | " | " | CH₃ | OCH₃ | CH₃ | N | |
| 53 | " | CH₃ | CHO | H | OCH₃ | OCH₃ | CH | 160–162 |
| 54 | " | " | " | H | OCH₃ | CH₃ | CH | |
| 55 | " | " | " | H | CH₃ | CH₃ | CH | |
| 56 | " | " | " | H | CH₃ | OC₂H₅ | CH | |
| 57 | " | " | " | H | OCH₃ | OCH₃ | N | |
| 58 | " | " | " | H | OCH₃ | CH₃ | N | |
| 59 | " | " | " | H | OCH₃ | Cl | CH | |
| 60 | " | " | " | H | OCF₂H | CH₃ | CH | |
| 61 | " | " | " | H | OCF₂H | OCF₂H | CH | |
| 62 | " | " | " | H | OCH₃ | Br | CH | |
| 63 | " | " | " | H | OCH₃ | OC₂H₅ | CH | |
| 64 | " | " | " | H | OCH₃ | SCH₃ | CH | |
| 65 | " | " | " | H | OCH₃ | OC₂H₅ | N | |
| 66 | " | " | " | H | OCH₃ | OC₃H₇ | CH | |
| 67 | " | " | " | H | CH₃ | Cl | CH | |
| 68 | " | " | " | H | Cl | OC₂H₅ | CH | |
| 69 | " | " | " | H | OC₂H₅ | OC₂H₅ | CH | |
| 70 | " | " | " | H | C₂H₅ | OCH₃ | CH | |
| 71 | " | " | " | H | CF₃ | OCH₃ | CH | |
| 72 | " | " | " | H | OCH₂CF₃ | CH₃ | CH | |
| 73 | " | " | " | H | OCH₂CF₃ | OCH₃ | CH | |
| 74 | " | " | " | H | OCH₂CF₃ | OCH₃ | CH | |
| 75 | " | " | " | H | OCH₂CF₃ | OCH₃ | N | |
| 76 | " | " | " | H | OCH₃ | CH(OCH₃)₂ | CH | |
| 77 | " | " | " | H | OCH₃ | OCH₃ | CH | |
| 78 | " | " | " | CH₃ | OCH₃ | CH₃ | N | |
| 79 | " | CH₃ | COCH₃ | H | OCH₃ | OCH₃ | CH | 166–168 |
| 80 | " | " | " | H | OCH₃ | CH₃ | CH | |
| 81 | " | " | " | H | CH₃ | CH₃ | CH | |
| 82 | " | " | " | H | CH₃ | OC₂H₅ | CH | |
| 83 | " | " | " | H | OCH₃ | OCH₃ | N | |
| 84 | " | " | " | H | OCH₃ | CH₃ | N | |
| 85 | " | " | " | H | OCH₃ | Cl | CH | |
| 86 | " | " | " | H | OCF₂H | CH₃ | CH | |
| 87 | " | " | " | H | OCF₂H | OCF₂H | CH | |
| 88 | " | " | " | H | OCH₃ | Br | CH | |
| 89 | " | " | " | H | OCH₃ | OC₂H₅ | CH | |

TABLE 2-continued (1b)

| CN | R¹ | R⁴ | R⁵ | R⁷ | X | Y | Z | Mp. °C. |
|---|---|---|---|---|---|---|---|---|
| 90 | " | " | " | H | OCH₃ | SCH₃ | CH | |
| 91 | " | " | " | H | OCH₃ | OC₂H₅ | N | |
| 92 | " | " | " | H | OCH₃ | OC₃H₇ | CH | |
| 93 | " | " | " | H | CH₃ | Cl | CH | |
| 94 | " | " | " | H | Cl | OC₂H₅ | CH | |
| 95 | " | " | " | H | OC₂H₅ | OC₂H₅ | CH | |
| 96 | " | " | " | H | C₂H₅ | OCH₃ | CH | |
| 97 | " | " | " | H | CF₃ | OCH₃ | CH | |
| 98 | " | " | " | H | OCH₂CF₃ | CH₃ | CH | |
| 99 | " | " | " | H | OCH₂CF₃ | OCH₃ | CH | |
| 100 | " | " | " | H | OCH₂CF₃ | OCH₂CF₃ | CH | |
| 101 | " | " | " | H | OCH₂CF₃ | OCH₃ | N | |
| 102 | " | " | " | H | OCH₃ | CH(OCH₃)₂ | CH | |
| 103 | " | " | " | CH₃ | OCH₃ | OCH₃ | CH | |
| 104 | " | " | " | CH₃ | OCH₃ | CH₃ | N | |
| 105 | " | H | SO₂CH₃ | H | OCH₃ | OCH₃ | CH | |
| 106 | " | " | " | H | OCH₃ | CH₃ | CH | |
| 107 | " | " | " | H | CH₃ | CH₃ | CH | |
| 108 | " | " | " | H | OCH₃ | OCH₃ | N | |
| 109 | " | " | " | H | OCH₃ | CH₃ | N | |
| 110 | " | " | " | H | OC₂H₅ | NHCH₃ | N | |
| 111 | " | " | " | CH₃ | OCH₃ | OCH₃ | CH | |
| 112 | " | " | " | CH₃ | OCH₃ | CH₃ | N | |
| 113 | " | CH₃ | SO₂CH₃ | H | OCH₃ | OCH₃ | CH | |
| 114 | " | " | " | H | OCH₃ | CH₃ | CH | |
| 115 | " | " | " | H | CH₃ | CH₃ | CH | |
| 116 | " | " | " | H | OCH₃ | OCH₃ | N | |
| 117 | " | " | " | H | OCH₃ | CH₃ | N | |
| 118 | " | " | " | H | OC₂H₅ | NHCH₃ | N | |
| 119 | " | " | " | CH₃ | OCH₃ | OCH₃ | CH | |
| 120 | " | " | " | CH₃ | OCH₃ | CH₃ | N | |
| 121 | " | OH | CHO | H | OCH₃ | OCH₃ | CH | |
| 122 | " | " | " | H | OCH₃ | CH₃ | CH | |
| 123 | " | " | " | H | CH₃ | CH₃ | CH | |
| 124 | " | " | " | H | OCH₃ | OCH₃ | N | |
| 125 | " | " | " | H | OCH₃ | CH₃ | N | |
| 126 | " | " | " | H | OC₂H₅ | NHCH₃ | N | |
| 127 | " | " | " | CH₃ | OCH₃ | OCH₃ | CH | |
| 128 | " | " | " | CH₃ | OCH₃ | CH₃ | N | |
| 129 | " | OCH₃ | CHO | H | OCH₃ | OCH₃ | CH | |
| 130 | " | " | " | H | OCH₃ | CH₃ | CH | |
| 131 | " | " | " | H | CH₃ | CH₃ | CH | |
| 132 | " | " | " | H | OCH₃ | OCH₃ | N | |
| 133 | " | " | " | H | OCH₃ | CH₃ | N | |
| 134 | " | " | " | H | OC₂H₅ | NHCH₃ | N | |
| 135 | " | " | " | CH₃ | OCH₃ | OCH₃ | CH | |
| 136 | " | " | " | CH₃ | OCH₃ | CH₃ | N | |
| 137 | " | OH | COCH₃ | H | OCH₃ | OCH₃ | CH | |
| 138 | " | " | " | H | OCH₃ | CH₃ | CH | |
| 139 | " | " | " | H | CH₃ | CH₃ | CH | |
| 140 | " | " | " | H | OCH₃ | OCH₃ | N | |
| 141 | " | " | " | H | OCH₃ | CH₃ | N | |
| 142 | " | " | " | H | OC₂H₅ | NHCH₃ | N | |
| 143 | " | " | " | CH₃ | OCH₃ | OCH₃ | CH | |
| 144 | " | " | " | CH₃ | OCH₃ | CH₃ | N | |
| 145 | " | OCH₃ | COCH₃ | H | OCH₃ | OCH₃ | CH | |
| 146 | " | " | " | H | OCH₃ | CH₃ | CH | |
| 147 | " | " | " | H | CH₃ | CH₃ | CH | |
| 148 | " | " | " | H | OCH₃ | OCH₃ | N | |
| 149 | " | " | " | H | OCH₃ | CH₃ | N | |
| 150 | " | " | " | H | OC₂H₅ | NHCH₃ | N | |
| 151 | " | " | " | CH₃ | OCH₃ | OCH₃ | CH | |
| 152 | " | " | " | CH₃ | OCH₃ | CH₃ | N | |
| 153 | " | H | COC₂H₅ | H | OCH₃ | OCH₃ | CH | 196 |
| 154 | " | " | " | H | OCH₃ | CH₃ | CH | |

TABLE 2-continued (1b)

| CN | R¹ | R⁴ | R⁵ | R⁷ | X | Y | Z | Mp. °C. |
|---|---|---|---|---|---|---|---|---|
| 155 | " | " | " | H | OCH₃ | OCH₃ | N | |
| 156 | " | " | " | H | OCH₃ | CH₃ | N | |
| 157 | " | CH₃ | " | H | OCH₃ | OCH₃ | CH | |
| 158 | " | " | " | H | OCH₃ | CH₃ | CH | |
| 159 | " | " | " | H | OCH₃ | OCH₃ | N | |
| 160 | " | " | " | H | OCH₃ | CH₃ | N | |
| 161 | " | H | COCH₂OCH₃ | H | OCH₃ | OCH₃ | CH | 192–195 |
| 162 | " | " | " | H | OCH₃ | CH₃ | CH | |
| 163 | " | " | " | H | OCH₃ | OCH₃ | N | |
| 164 | " | " | " | H | OCH₃ | CH₃ | N | |
| 165 | " | CH₃ | " | H | OCH₃ | OCH₃ | CH | |
| 166 | " | " | " | H | OCH₃ | CH₃ | CH | |
| 167 | " | " | " | H | OCH₃ | OCH₃ | N | |
| 168 | " | " | " | H | OCH₃ | CH₃ | N | |
| 169 | " | H | COCO₂C₂H₅ | H | OCH₃ | OCH₃ | CH | 183–185 |
| 170 | " | " | " | H | OCH₃ | CH₃ | CH | |
| 171 | " | " | " | H | OCH₃ | OCH₃ | N | |
| 172 | " | " | " | H | OCH₃ | CH₃ | N | |
| 173 | " | CH₃ | " | H | OCH₃ | OCH₃ | CH | |
| 174 | " | " | " | H | OCH₃ | CH₃ | CH | |
| 175 | " | " | " | H | OCH₃ | OCH₃ | N | |
| 176 | " | " | " | H | OCH₃ | CH₃ | N | |
| 177 | " | H | COCF₃ | H | OCH₃ | OCH₃ | CH | 180–182 |
| 178 | " | " | " | H | OCH₃ | CH₃ | CH | |
| 179 | " | " | " | H | OCH₃ | OCH₃ | N | |
| 180 | " | " | " | H | OCH₃ | CH₃ | N | |
| 181 | " | CH₃ | " | H | OCH₃ | OCH₃ | CH | 144–147 |
| 182 | " | " | " | H | OCH₃ | CH₃ | CH | |
| 183 | " | " | " | H | OCH₃ | OCH₃ | N | |
| 184 | " | " | " | H | OCH₃ | CH₃ | N | |
| 185 | " | H | COOCH₃ | H | OCH₃ | OCH₃ | CH | 178–180 |
| 186 | " | " | " | H | OCH₃ | CH₃ | CH | |
| 187 | " | " | " | H | OCH₃ | OCH₃ | N | |
| 188 | " | " | " | H | OCH₃ | CH₃ | N | |
| 189 | " | CH₃ | " | H | OCH₃ | OCH₃ | CH | |
| 190 | " | " | " | H | OCH₃ | CH₃ | CH | |
| 191 | " | " | " | H | OCH₃ | OCH₃ | N | |
| 192 | " | " | " | H | OCH₃ | CH₃ | N | |
| 193 | " | H | CONHC₂H₅ | H | OCH₃ | OCH₃ | CH | |
| 194 | " | " | " | H | OCH₃ | CH₃ | CH | |
| 195 | " | " | " | H | OCH₃ | OCH₃ | N | |
| 196 | " | " | " | H | OCH₃ | CH₃ | N | |
| 197 | " | CH₃ | " | H | OCH₃ | OCH₃ | CH | |
| 198 | " | " | " | H | OCH₃ | CH₃ | CH | |
| 199 | " | " | " | H | OCH₃ | OCH₃ | N | |
| 200 | " | " | " | H | OCH₃ | CH₃ | N | |
| 201 | " | H | CSNHC₂H₅ | H | OCH₃ | OCH₃ | CH | |
| 202 | " | " | " | H | OCH₃ | CH₃ | CH | |
| 203 | " | " | " | H | OCH₃ | OCH₃ | N | |
| 204 | " | " | " | H | OCH₃ | CH₃ | N | |
| 205 | " | CH₃ | " | H | OCH₃ | OCH₃ | CH | |
| 206 | " | " | " | H | OCH₃ | CH₃ | CH | |
| 207 | " | " | " | H | OCH₃ | OCH₃ | N | |
| 208 | " | " | " | H | OCH₃ | CH₃ | N | |
| 209 | " | H | SO₂NHCH₃ | H | OCH₃ | OCH₃ | CH | |
| 210 | " | " | " | H | OCH₃ | CH₃ | CH | |
| 211 | " | " | " | H | OCH₃ | OCH₃ | N | |
| 212 | " | " | " | H | OCH₃ | CH₃ | N | |
| 213 | " | CH₃ | " | H | OCH₃ | OCH₃ | CH | |
| 214 | " | " | " | H | OCH₃ | CH₃ | CH | |
| 215 | " | " | " | H | OCH₃ | OCH₃ | N | |
| 216 | " | " | " | H | OCH₃ | CH₃ | N | |
| 217 | " | H | SO₂N(CH₃)₂ | H | OCH₃ | OCH₃ | CH | |
| 218 | " | " | " | H | OCH₃ | CH₃ | CH | |
| 219 | " | " | " | H | OCH₃ | OCH₃ | N | |

TABLE 2-continued (1b)

| CN | R¹ | R⁴ | R⁵ | R⁷ | X | Y | Z | Mp. °C. |
|---|---|---|---|---|---|---|---|---|
| 220 | " | " | " | H | OCH₃ | CH₃ | N | |
| 221 | " | CH₃ | " | H | OCH₃ | OCH₃ | CH | |
| 222 | " | " | " | H | OCH₃ | CH₃ | CH | |
| 223 | " | " | " | H | OCH₃ | OCH₃ | N | |
| 224 | " | " | " | H | OCH₃ | CH₃ | N | |
| 225 | " | —CH₂CH₂CH₂CO— | | H | OCH₃ | OCH₃ | CH | |
| 226 | " | " | | H | OCH₃ | CH₃ | CH | |
| 227 | " | " | | H | OCH₃ | OCH₃ | N | |
| 228 | " | " | | H | OCH₃ | CH₃ | N | |
| 229 | " | —CH₂CH₂CH₂SO₂— | | H | OCH₃ | OCH₃ | CH | |
| 230 | " | " | | H | OCH₃ | CH₃ | CH | |
| 231 | " | " | | H | OCH₃ | OCH₃ | N | |
| 232 | " | " | | H | OCH₃ | CH₃ | N | |
| 233 | " | —CH₂CH₂CH₂CH₂CO— | | H | OCH₃ | OCH₃ | CH | |
| 234 | " | " | | H | OCH₃ | CH₃ | CH | |
| 235 | " | " | | H | OCH₃ | OCH₃ | N | |
| 236 | " | " | | H | OCH₃ | CH₃ | N | |
| 237 | " | —CH₂CH₂CH₂CH₂SO₂— | | H | OCH₃ | OCH₃ | CH | |
| 238 | " | " | | H | OCH₃ | CH₃ | CH | |
| 239 | " | " | | H | OCH₃ | OCH₃ | N | |
| 240 | " | " | | H | OCH₃ | CH₃ | N | |
| 241 | " | —CH₂CH₂OCH₂CH₂— | | H | OCH₃ | OCH₃ | CH | |
| 242 | " | " | | H | OCH₃ | CH₃ | CH | |
| 243 | " | " | | H | OCH₃ | OCH₃ | N | |
| 244 | " | " | | H | OCH₃ | CH₃ | N | |
| 245 | " | H | COC₃H₇ | H | OCH₃ | OCH₃ | CH | |
| 246 | " | " | " | H | OCH₃ | CH₃ | CH | |
| 247 | " | " | " | H | OCH₃ | OCH₃ | N | |
| 248 | " | " | " | H | OCH₃ | CH₃ | N | |
| 249 | " | CH₃ | " | H | OCH₃ | OCH₃ | CH | |
| 250 | " | " | " | H | OCH₃ | CH₃ | CH | |
| 251 | " | " | " | H | OCH₃ | OCH₃ | N | |
| 252 | " | " | " | H | OCH₃ | CH₃ | N | |
| 253 | " | H | COCH₂Cl | H | OCH₃ | OCH₃ | CH | 170–172 |
| 254 | " | " | " | H | OCH₃ | CH₃ | CH | |
| 255 | " | " | " | H | OCH₃ | OCH₃ | N | |
| 256 | " | " | " | H | OCH₃ | CH₃ | N | |
| 257 | " | CH₃ | " | H | OCH₃ | OCH₃ | CH | |
| 258 | " | " | " | H | OCH₃ | CH₃ | CH | |
| 259 | " | " | " | H | OCH₃ | OCH₃ | N | |
| 260 | " | " | " | H | OCH₃ | CH₃ | N | |
| 261 | " | H | COCHCl₂ | H | OCH₃ | OCH₃ | CH | 158–160 |
| 262 | " | " | " | H | OCH₃ | CH₃ | CH | |
| 263 | " | " | " | H | OCH₃ | OCH₃ | N | |
| 264 | " | " | " | H | OCH₃ | CH₃ | N | |
| 265 | " | CH₃ | " | H | OCH₃ | OCH₃ | CH | |
| 266 | " | " | " | H | OCH₃ | CH₃ | CH | |
| 267 | " | " | " | H | OCH₃ | OCH₃ | N | |
| 268 | " | " | " | H | OCH₃ | CH₃ | N | |
| 269 | " | H | COCCl₃ | H | OCH₃ | OCH₃ | CH | 194–196 |
| 270 | " | " | " | H | OCH₃ | CH₃ | CH | |
| 271 | " | " | " | H | OCH₃ | OCH₃ | N | |
| 272 | " | " | " | H | OCH₃ | CH₃ | N | |
| 273 | " | CH₃ | " | H | OCH₃ | OCH₃ | CH | |
| 274 | " | " | " | H | OCH₃ | CH₃ | CH | |
| 275 | " | " | " | H | OCH₃ | OCH₃ | N | |
| 276 | " | " | " | H | OCH₃ | CH₃ | N | |
| 277 | " | H | COCH=CH₂ | H | OCH₃ | OCH₃ | CH | |
| 278 | " | " | " | H | OCH₃ | CH₃ | CH | |
| 279 | " | " | " | H | OCH₃ | OCH₃ | N | |
| 280 | " | " | " | H | OCH₃ | CH₃ | N | |
| 281 | " | CH₃ | " | H | OCH₃ | OCH₃ | CH | |
| 282 | " | " | " | H | OCH₃ | CH₃ | CH | |
| 283 | " | " | " | H | OCH₃ | OCH₃ | N | |
| 284 | " | " | " | H | OCH₃ | CH₃ | N | |

TABLE 2-continued (1b)

| CN | R¹ | R⁴ | R⁵ | R⁷ | X | Y | Z | Mp. °C. |
|---|---|---|---|---|---|---|---|---|
| 285 | " | H | COC≡CH | H | OCH₃ | OCH₃ | CH | |
| 286 | " | " | " | H | OCH₃ | CH₃ | CH | |
| 287 | " | " | " | H | OCH₃ | OCH₃ | N | |
| 288 | " | " | " | H | OCH₃ | CH₃ | N | |
| 289 | " | CH₃ | " | H | OCH₃ | OCH₃ | CH | |
| 290 | " | " | " | H | OCH₃ | CH₃ | CH | |
| 291 | " | " | " | H | OCH₃ | OCH₃ | N | |
| 292 | " | " | " | H | OCH₃ | CH₃ | N | |
| 293 | " | H | COC₆H₅ | H | OCH₃ | OCH₃ | CH | |
| 294 | " | " | " | H | OCH₃ | CH₃ | CH | |
| 295 | " | " | " | H | OCH₃ | OCH₃ | N | |
| 296 | " | " | " | H | OCH₃ | CH₃ | N | |
| 297 | " | CH₃ | " | H | OCH₃ | OCH₃ | CH | |
| 298 | " | " | " | H | OCH₃ | CH₃ | CH | |
| 299 | " | " | " | H | OCH₃ | OCH₃ | N | |
| 300 | " | " | " | H | OCH₃ | CH₃ | N | |
| 301 | " | SO₂C₆H₅ | SO₂C₆H₅ | H | OCH₃ | OCH₃ | CH | |
| 302 | " | " | " | H | OCH₃ | CH₃ | CH | |
| 303 | " | " | " | H | OCH₃ | OCH₃ | N | |
| 304 | " | " | " | H | OCH₃ | CH₃ | N | |
| 305 | " | SO₂CH₃ | SO₂CH₃ | H | OCH₃ | OCH₃ | CH | |
| 306 | " | " | " | H | OCH₃ | CH₃ | CH | |
| 307 | " | " | " | H | OCH₃ | OCH₃ | N | |
| 308 | " | " | " | H | OCH₃ | CH₃ | N | |
| 309 | " | H | COCH₂Br | H | OCH₃ | OCH₃ | CH | |
| 310 | " | " | " | H | OCH₃ | CH₃ | N | |
| 311 | " | CH₃ | " | H | OCH₃ | OCH₃ | CH | |
| 312 | " | " | " | H | OCH₃ | CH₃ | N | |
| 313 | " | H | COCH₂F | H | OCH₃ | OCH₃ | CH | |
| 314 | " | " | " | H | OCH₃ | CH₃ | N | |
| 315 | " | CH₃ | " | H | OCH₃ | OCH₃ | CH | |
| 316 | " | " | " | H | OCH₃ | CH₃ | N | |
| 317 | " | H | COCH₂C≡CH | H | OCH₃ | OCH₃ | CH | |
| 318 | " | " | " | H | OCH₃ | CH₃ | N | |
| 319 | " | CH₃ | " | H | OCH₃ | OCH₃ | CH | |
| 320 | " | " | " | H | OCH₃ | CH₃ | N | |
| 321 | " | H | COCO₂CH₃ | H | OCH₃ | OCH₃ | CH | |
| 322 | " | " | " | H | OCH₃ | CH₃ | N | |
| 323 | " | CH₃ | " | H | OCH₃ | OCH₃ | CH | |
| 324 | " | " | " | H | OCH₃ | CH₃ | N | |
| 325 | " | H | CO₂C₂H₅ | H | OCH₃ | OCH₃ | CH | |
| 326 | " | " | " | H | OCH₃ | CH₃ | N | |
| 327 | " | CH₃ | " | H | OCH₃ | OCH₃ | CH | |
| 328 | " | " | " | H | OCH₃ | CH₃ | N | |
| 329 | " | H | COSCH₃— | H | OCH₃ | OCH₃ | CH | |
| 330 | " | " | " | H | OCH₃ | CH₃ | N | |
| 331 | " | CH₃ | " | H | OCH₃ | OCH₃ | CH | |
| 332 | " | " | " | H | OCH₃ | CH₃ | N | |
| 333 | " | H | CSOCH₃ | H | OCH₃ | OCH₃ | CH | |
| 334 | " | " | " | H | OCH₃ | CH₃ | N | |
| 335 | " | CH₃ | " | H | OCH₃ | OCH₃ | CH | |
| 336 | " | " | " | H | OCH₃ | CH₃ | N | |
| 337 | " | H | CSSCH₃ | H | OCH₃ | OCH₃ | CH | |
| 338 | " | " | " | H | OCH₃ | CH₃ | N | |
| 339 | " | CH₃ | " | H | OCH₃ | OCH₃ | CH | |
| 340 | " | " | " | H | OCH₃ | CH₃ | N | |
| 341 | " | H | COCH(CH₃)₂ | H | OCH₃ | OCH₃ | CH | 195–196 |
| 342 | " | " | " | H | OCH₃ | CH₃ | N | |
| 343 | " | CH₃ | " | H | OCH₃ | OCH₃ | CH | |
| 344 | " | " | " | H | OCH₃ | CH₃ | N | |
| 345 | " | H | COC(CH₃)₃ | H | OCH₃ | OCH₃ | CH | |
| 346 | " | " | " | H | OCH₃ | CH₃ | N | |
| 347 | " | CH₃ | " | H | OCH₃ | OCH₃ | CH | |
| 348 | " | " | " | H | OCH₃ | CH₃ | N | |
| 349 | " | H | CO-Cyclopropyl | H | OCH₃ | OCH₃ | CH | 202–203 |

TABLE 2-continued (1b)

| CN | R¹ | R⁴ | R⁵ | R⁷ | X | Y | Z | Mp. ° C. |
|---|---|---|---|---|---|---|---|---|
| 350 | " | " | " | H | OCH₃ | CH₃ | N | |
| 351 | " | CH₃ | " | H | OCH₃ | OCH₃ | CH | |
| 352 | " | " | " | H | OCH₃ | CH₃ | N | |
| 353 | " | H | CO-Cyclobutyl | H | OCH₃ | OCH₃ | CH | |
| 354 | " | " | " | H | OCH₃ | CH₃ | N | |
| 355 | " | CH₃ | " | H | OCH₃ | OCH₃ | CH | |
| 356 | " | " | " | H | OCH₃ | CH₃ | N | |
| 357 | " | H | CO-Cyclopentyl | H | OCH₃ | OCH₃ | CH | |
| 358 | " | " | " | H | OCH₃ | CH₃ | N | |
| 359 | " | CH₃ | " | H | OCH₃ | OCH₃ | CH | |
| 360 | " | " | " | H | OCH₃ | CH₃ | N | |
| 361 | " | H | CO-Cyclohexyl | H | OCH₃ | OCH₃ | CH | |
| 362 | " | " | " | H | OCH₃ | CH₃ | N | |
| 363 | " | CH₃ | " | H | OCH₃ | OCH₃ | CH | |
| 364 | " | " | " | H | OCH₃ | CH₃ | N | |
| 365 | " | H | CONHCH₂CH₂Cl | H | OCH₃ | OCH₃ | CH | 178–182 |
| 366 | " | " | " | H | OCH₃ | CH₃ | N | |
| 367 | " | CH₃ | " | H | OCH₃ | OCH₃ | CH | |
| 368 | " | " | " | H | OCH₃ | CH₃ | N | |
| 369 | " | H | CSNHCH₂CH₂Cl | H | OCH₃ | OCH₃ | CH | |
| 370 | " | " | " | H | OCH₃ | CH₃ | N | |
| 371 | " | CH₃ | " | H | OCH₃ | OCH₃ | CH | |
| 372 | " | " | " | H | OCH₃ | CH₃ | N | |
| 373 | " | H | CONH-n-C₄H₉ | H | OCH₃ | OCH₃ | CH | 183–184 |
| 374 | " | " | " | H | OCH₃ | CH₃ | N | |
| 375 | " | CH₃ | " | H | OCH₃ | OCH₃ | CH | |
| 376 | " | " | " | H | OCH₃ | CH₃ | N | |
| 377 | " | H | CSNHCH₃ | H | OCH₃ | OCH₃ | CH | |
| 378 | " | " | " | H | OCH₃ | CH₃ | N | |
| 379 | " | CH₃ | " | H | OCH₃ | OCH₃ | CH | |
| 380 | " | " | " | H | OCH₃ | CH₃ | N | |
| 381 | " | H | CSNHCH₂CH=CH₂ | H | OCH₃ | OCH₃ | CH | |
| 382 | " | " | " | H | OCH₃ | CH₃ | N | |
| 383 | " | CH₃ | " | H | OCH₃ | OCH₃ | CH | |
| 384 | " | " | " | H | OCH₃ | CH₃ | N | |
| 385 | " | CH₃ | CSNHCH₂COCH₃ | H | OCH₃ | OCH₃ | CH | |
| 386 | " | " | " | H | OCH₃ | CH₃ | N | |
| 387 | " | CH₃ | CSNHCH₂COC₂H₅ | H | OCH₃ | OCH₃ | CH | |
| 388 | " | " | " | H | OCH₃ | CH₃ | N | |
| 389 | " | CH₃ | CONHCH₂COCH₃ | H | OCH₃ | OCH₃ | CH | |
| 390 | " | " | " | H | OCH₃ | CH₃ | N | |
| 391 | " | CH₃ | CONHCH₂COC₂H₅ | H | OCH₃ | OCH₃ | CH | |
| 392 | " | " | " | H | OCH₃ | CH₃ | N | |
| 393 | " | | —CONHCH₂CO— | H | OCH₃ | OCH₃ | CH | |
| 394 | " | | " | H | OCH₃ | CH₃ | N | |
| 395 | " | H | SO₂CH₂F | H | OCH₃ | OCH₃ | CH | |
| 396 | " | " | " | H | OCH₃ | CH₃ | N | |
| 397 | " | CH₃ | " | H | OCH₃ | OCH₃ | CH | |
| 398 | " | " | " | H | OCH₃ | CH₃ | N | |
| 399 | " | H | SO₂CF₃ | H | OCH₃ | OCH₃ | CH | |
| 400 | " | " | " | H | OCH₃ | CH₃ | N | |
| 401 | " | CH₃ | " | H | OCH₃ | OCH₃ | CH | |
| 402 | " | " | " | H | OCH₃ | CH₃ | N | |
| 403 | " | H | SO₂C₂H₅ | H | OCH₃ | OCH₃ | CH | |
| 404 | " | " | " | H | OCH₃ | CH₃ | N | |
| 405 | " | CH₃ | " | H | OCH₃ | OCH₃ | CH | |
| 406 | " | " | " | H | OCH₃ | CH₃ | N | |
| 407 | " | H | SO₂-n-C₃H₇ | H | OCH₃ | OCH₃ | CH | |
| 408 | " | " | " | H | OCH₃ | CH₃ | N | |
| 409 | " | CH₃ | " | H | OCH₃ | OCH₃ | CH | |
| 410 | " | " | " | H | OCH₃ | CH₃ | N | |
| 411 | " | OH | COC₂H₅ | H | OCH₃ | OCH₃ | CH | |
| 412 | " | " | " | H | OCH₃ | CH₃ | N | |
| 413 | " | OCH₃ | " | H | OCH₃ | OCH₃ | CH | |
| 414 | " | " | " | H | OCH₃ | CH₃ | N | |

TABLE 2-continued (1b)

Structure: R⁴R⁵N-CH₂-[benzene with R¹]-SO₂NH-C(O)-N(R⁷)-[triazine with X, Y, Z]

| CN | R¹ | R⁴ | R⁵ | R⁷ | X | Y | Z | Mp. °C. |
|---|---|---|---|---|---|---|---|---|
| 415 | " | OH | COCH₂Cl | H | OCH₃ | OCH₃ | CH | |
| 416 | " | " | " | H | OCH₃ | CH₃ | N | |
| 417 | " | OCH₃ | " | H | OCH₃ | OCH₃ | CH | |
| 418 | " | " | " | H | OCH₃ | CH₃ | N | |
| 419 | " | OH | COCF₃ | H | OCH₃ | OCH₃ | CH | |
| 420 | " | " | " | H | OCH₃ | CH₃ | N | |
| 421 | " | OCH₃ | " | H | OCH₃ | OCH₃ | CH | |
| 422 | " | " | " | H | OCH₃ | CH₃ | N | |
| 423 | " | OH | COCH₂OCH₃ | H | OCH₃ | OCH₃ | CH | |
| 424 | " | " | " | H | OCH₃ | CH₃ | N | |
| 425 | " | OCH₃ | " | H | OCH₃ | OCH₃ | CH | |
| 426 | " | " | " | H | OCH₃ | CH₃ | N | |
| 427 | " | OH | COCO₂C₂H₅ | H | OCH₃ | OCH₃ | CH | |
| 428 | " | " | " | H | OCH₃ | CH₃ | N | |
| 429 | " | OCH₃ | " | H | OCH₃ | OCH₃ | CH | |
| 430 | " | " | " | H | OCH₃ | CH₃ | N | |
| 431 | " | OH | COOCH₃ | H | OCH₃ | OCH₃ | CH | |
| 432 | " | " | " | H | OCH₃ | CH₃ | N | |
| 433 | " | OCH₃ | " | H | OCH₃ | OCH₃ | CH | |
| 434 | " | " | " | H | OCH₃ | CH₃ | N | |
| 435 | " | OH | Cyclopropyl | H | OCH₃ | OCH₃ | CH | |
| 436 | " | " | " | H | OCH₃ | CH₃ | N | |
| 437 | " | OCH₃ | " | H | OCH₃ | OCH₃ | CH | |
| 438 | " | " | " | H | OCH₃ | CH₃ | N | |
| 439 | " | OH | COC₆H₅ | H | OCH₃ | OCH₃ | CH | |
| 440 | " | " | " | H | OCH₃ | CH₃ | N | |
| 441 | " | OCH₃ | " | H | OCH₃ | OCH₃ | CH | |
| 442 | " | " | " | H | OCH₃ | CH₃ | N | |
| 443 | " | OH | COCH(CH₃)₂ | H | OCH₃ | OCH₃ | CH | |
| 444 | " | " | " | H | OCH₃ | CH₃ | N | |
| 445 | " | OCH₃ | " | H | OCH₃ | OCH₃ | CH | |
| 446 | " | " | " | H | OCH₃ | CH₃ | N | |
| 447 | " | OH | COCH=CH₂ | H | OCH₃ | OCH₃ | CH | |
| 448 | " | " | " | H | OCH₃ | CH₃ | N | |
| 449 | " | OCH₃ | " | H | OCH₃ | OCH₃ | CH | |
| 450 | " | " | " | H | OCH₃ | CH₃ | N | |
| 451 | " | OH | COC≡CH | H | OCH₃ | OCH₃ | CH | |
| 452 | " | " | " | H | OCH₃ | CH₃ | N | |
| 453 | " | OCH₃ | " | H | OCH₃ | OCH₃ | CH | |
| 454 | " | " | " | H | OCH₃ | CH₃ | N | |
| 455 | " | OH | SO₂CH₃ | H | OCH₃ | OCH₃ | CH | |
| 456 | " | " | " | H | OCH₃ | CH₃ | N | |
| 457 | " | OCH₃ | " | H | OCH₃ | OCH₃ | CH | |
| 458 | " | " | " | H | OCH₃ | CH₃ | N | |
| 459 | " | OH | SO₂NHCH₃ | H | OCH₃ | OCH₃ | CH | |
| 460 | " | " | " | H | OCH₃ | CH₃ | N | |
| 461 | " | OCH₃ | " | H | OCH₃ | OCH₃ | CH | |
| 462 | " | " | " | H | OCH₃ | CH₃ | N | |
| 463 | " | OH | SO₂N(CH₃)₂ | H | OCH₃ | OCH₃ | CH | |
| 464 | " | " | " | H | OCH₃ | CH₃ | N | |
| 465 | " | OCH₃ | " | H | OCH₃ | OCH₃ | CH | |
| 466 | " | " | " | H | OCH₃ | CH₃ | N | |
| 467 | " | C₂H₅ | CHO | H | OCH₃ | OCH₃ | CH | |
| 468 | " | " | " | H | OCH₃ | CH₃ | N | |
| 469 | " | " | COCH₃ | H | OCH₃ | OCH₃ | CH | |
| 470 | " | " | " | H | OCH₃ | CH₃ | N | |
| 471 | " | " | Cyclopropyl | H | OCH₃ | OCH₃ | CH | |
| 472 | " | " | " | H | OCH₃ | CH₃ | N | |
| 473 | " | " | COCH₂Cl | H | OCH₃ | OCH₃ | CH | |
| 474 | " | " | " | H | OCH₃ | CH₃ | N | |
| 475 | " | " | COCF₃ | H | OCH₃ | OCH₃ | CH | |
| 476 | " | " | " | H | OCH₃ | CH₃ | N | |
| 477 | " | " | COOCH₃ | H | OCH₃ | OCH₃ | CH | |
| 478 | " | " | " | H | OCH₃ | CH₃ | N | |
| 479 | " | " | COC₆H₅ | H | OCH₃ | OCH₃ | CH | |

TABLE 2-continued

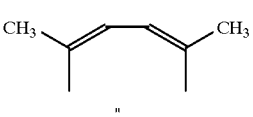

(1b)

| CN | R¹ | R⁴ | R⁵ | R⁷ | X | Y | Z | Mp. °C. |
|---|---|---|---|---|---|---|---|---|
| 480 | " | " | " | H | OCH₃ | CH₃ | N | |
| 481 | " | " | CONHC₂H₅ | H | OCH₃ | OCH₃ | CH | |
| 482 | " | " | " | H | OCH₃ | CH₃ | N | |
| 483 | " | " | CSNHC₂H₅ | H | OCH₃ | OCH₃ | CH | |
| 484 | " | " | " | H | OCH₃ | CH₃ | N | |
| 485 | " | " | SO₂CH₃ | H | OCH₃ | OCH₃ | CH | |
| 486 | " | " | " | H | OCH₃ | CH₃ | N | |
| 487 | " | " | SO₂NHCH₃ | H | OCH₃ | OCH₃ | CH | |
| 488 | " | " | " | H | OCH₃ | CH₃ | N | |
| 489 | " | " | SO₂N(CH₃)₂ | H | OCH₃ | OCH₃ | CH | |
| 490 | " | " | " | H | OCH₃ | CH₃ | N | |
| 491 | " | " | SO₂C₆H₅ | H | OCH₃ | OCH₃ | CH | |
| 492 | " | " | " | H | OCH₃ | CH₃ | N | |
| 493 | CO₂C₂H₅ | H | CHO | H | OCH₃ | OCH₃ | CH | |
| 494 | " | " | " | H | OCH₃ | CH₃ | N | |
| 495 | " | " | COCH₃ | H | OCH₃ | OCH₃ | CH | |
| 496 | " | " | " | H | OCH₃ | CH₃ | N | |
| 497 | " | " | SO₂CH₃ | H | OCH₃ | OCH₃ | CH | |
| 498 | " | " | " | H | OCH₃ | CH₃ | N | |
| 499 | " | CH₃ | CHO | H | OCH₃ | OCH₃ | CH | |
| 500 | " | " | " | H | OCH₃ | CH₃ | N | |
| 501 | " | " | COCH₃ | H | OCH₃ | OCH₃ | CH | |
| 502 | " | " | " | H | OCH₃ | CH₃ | N | |
| 503 | " | " | SO₂CH₃ | H | OCH₃ | OCH₃ | CH | |
| 504 | " | " | " | H | OCH₃ | CH₃ | N | |
| 505 | " | C₂H₅ | CHO | H | OCH₃ | OCH₃ | CH | |
| 506 | " | " | " | H | OCH₃ | CH₃ | N | |
| 507 | " | " | COCH₃ | H | OCH₃ | OCH₃ | CH | |
| 508 | " | " | " | H | OCH₃ | CH₃ | N | |
| 509 | " | " | SO₂CH₃ | H | OCH₃ | OCH₃ | CH | |
| 510 | " | " | " | H | OCH₃ | CH₃ | N | |
| 511 | " | OH | CHO | H | OCH₃ | OCH₃ | CH | |
| 512 | " | " | " | H | OCH₃ | CH₃ | N | |
| 513 | " | " | COCH₃ | H | OCH₃ | OCH₃ | CH | |
| 514 | " | " | " | H | OCH₃ | CH₃ | N | |
| 515 | " | " | SO₂CH₃ | H | OCH₃ | OCH₃ | CH | |
| 516 | " | " | " | H | OCH₃ | CH₃ | N | |
| 517 | " | OCH₃ | CHO | H | OCH₃ | OCH₃ | CH | |
| 518 | " | " | " | H | OCH₃ | CH₃ | N | |
| 519 | " | " | COCH₃ | H | OCH₃ | OCH₃ | CH | |
| 520 | " | " | " | H | OCH₃ | CH₃ | N | |
| 521 | CO₂-n-Bu | H | CHO | H | " | OMe | CH | |
| 522 | CONMe₂ | Me | " | H | " | Me | N | |
| 523 | CONHMe | H | " | H | " | OMe | CH | |
| 524 | COSMe | Me | CO—Me | H | " | Me | N | |
| 525 | CO₂Me | n-Bu | CHO | H | " | OMe | CH | |
| 526 | " | n-Bu | " | H | " | Me | N | |
| 527 | " | H | " | H | OCH₂CF₃ | NMe₂ | " | |
| 528 | " | Me | " | H | " | " | " | |
| 529 | " | H | CO—Me | H | " | " | " | |
| 530 | " | Me | " | H | " | " | " | |
| 531 | " | " | SO₂CH₃ | H | OCH₃ | OCH₃ | CH | |
| 532 | " | " | " | H | OCH₃ | CH₃ | N | |
| 533 | " | CH₃\_/\_CH₃ " | | H | OCH₃ | OCH₃ | CH | |

TABLE 2-continued (1b)

Structure: R⁴R⁵N-CH₂- attached to benzene ring with R¹, -SO₂NH-C(=O)-N(R⁷)- connected to triazine with X, Y, Z

| CN | R¹ | R⁴ | R⁵ | R⁷ | X | Y | Z | Mp. °C. |
|---|---|---|---|---|---|---|---|---|
| 534 | " | CH₃-C=CH-CH=C-CH₃ (with CH₃ groups) | " | H | OCH₃ | CH₃ | N | |

TABLE 3

(Ic)

| CN | R¹ | R⁴ | R⁵ | R⁷ | X | Y | Z | Mp. °C. |
|---|---|---|---|---|---|---|---|---|
| 1 | CO₂CH₃ | H | CHO | H | OCH₃ | OCH₃ | CH | |
| 2 | " | " | " | H | OCH₃ | CH₃ | CH | |
| 3 | " | " | " | H | CH₃ | CH₃ | CH | |
| 4 | " | " | " | H | CH₃ | OC₂H₆ | CH | |
| 5 | " | " | " | H | OCH₃ | OCH₃ | N | |
| 6 | " | " | " | H | OCH₃ | CH₃ | N | |
| 7 | " | " | " | H | OCH₃ | Cl | CH | |
| 8 | " | " | " | H | OCF₂H | CH₃ | CH | |
| 9 | " | " | " | H | OCF₂H | OCF₂H | CH | |
| 10 | " | " | " | H | OCH₃ | Br | CH | |
| 11 | " | " | " | H | OCH₃ | OC₂H₅ | CH | |
| 12 | " | " | " | H | OCH₃ | SCH₃ | CH | |
| 13 | " | " | " | H | OCH₃ | OC₂H₆ | N | |
| 14 | " | " | " | H | OCH₃ | OC₃H₇ | CH | |
| 15 | " | " | " | H | CH₃ | Cl | CH | |
| 16 | " | " | " | H | Cl | OC₂H₅ | CH | |
| 17 | " | " | " | H | OC₂H₅ | OC₂H₅ | CH | |
| 18 | " | " | " | H | C₂H₅ | OCH₃ | CH | |
| 19 | " | " | " | H | CF₃ | OCH₃ | CH | |
| 20 | " | " | " | H | OCH₂CF₃ | CH₃ | CH | |
| 21 | " | " | " | H | OCH₂CF₃ | OCH₃ | CH | |
| 22 | " | " | " | H | OCH₂CF₃ | OCH₂CF₃ | CH | |
| 23 | " | " | " | H | OCH₂CF₃ | OCH₃ | N | |
| 24 | " | " | " | H | OCH₃ | CH(OCH₃)₂ | CH | |
| 25 | " | " | " | CH₃ | OCH₃ | OCH₃ | CH | |
| 26 | " | " | " | CH₃ | OCH₃ | CH₃ | N | |
| 27 | " | H | COCH₃ | H | OCH₃ | OCH₃ | CH | 198–200 |
| 28 | " | " | " | H | OCH₃ | CH₃ | CH | |
| 29 | " | " | " | H | CH₃ | CH₃ | CH | |
| 30 | " | " | " | H | CH₃ | OC₂H₅ | CH | |
| 31 | " | " | " | H | OCH₃ | OCH₃ | N | |
| 32 | " | " | " | H | OCH₃ | CH₃ | N | |
| 33 | " | " | " | H | OCH₃ | Cl | CH | |
| 34 | " | " | " | H | OCF₂H | CH₃ | CH | |
| 35 | " | " | " | H | OCF₂H | OCF₂H | CH | |
| 36 | " | " | " | H | OCH₃ | Br | CH | |
| 37 | " | " | " | H | OCH₃ | OC₂H₅ | CH | |
| 38 | " | " | " | H | OCH₃ | SCH₃ | CH | |

TABLE 3-continued (Ic)

| CN | R¹ | R⁴ | R⁵ | R⁷ | X | Y | Z | Mp. °C. |
|---|---|---|---|---|---|---|---|---|
| 39 | " | " | " | H | OCH₃ | OC₂H₅ | N | |
| 40 | " | " | " | H | OCH₃ | OC₃H₇ | CH | |
| 41 | " | " | " | H | CH₃ | Cl | CH | |
| 42 | " | " | " | H | Cl | OC₂H₅ | CH | |
| 43 | " | " | " | H | OC₂H₅ | OC₂H₅ | CH | |
| 44 | " | " | " | H | C₂H₅ | OCH₃ | CH | |
| 45 | " | " | " | H | CF₃ | OCH₃ | CH | |
| 46 | " | " | " | H | OCH₂CF₃ | CH₃ | CH | |
| 47 | " | " | " | H | OCH₂CF₃ | OCH₃ | CH | |
| 48 | " | " | " | H | OCH₂CF₃ | OCH₂CF₃ | CH | |
| 49 | " | " | " | H | OCH₂CF₃ | OCH₃ | N | |
| 50 | " | " | " | H | OCH₃ | CH(OCH₃)₂ | CH | |
| 51 | " | " | " | CH₃ | OCH₃ | OCH₃ | CH | |
| 52 | " | " | " | CH₃ | OCH₃ | CH₃ | N | |
| 53 | " | CH₃ | CHO | H | OCH₃ | OCH₃ | CH | |
| 54 | " | " | " | H | OCH₃ | CH₃ | CH | |
| 55 | " | " | " | H | CH₃ | CH₃ | CH | |
| 56 | " | " | " | H | CH₃ | OC₂H₅ | CH | |
| 57 | " | " | " | H | OCH₃ | OCH₃ | N | |
| 58 | " | " | " | H | OCH₃ | CH₃ | N | |
| 59 | " | " | " | H | OCH₃ | Cl | CH | |
| 60 | " | " | " | H | OCF₂H | CH₃ | CH | |
| 61 | " | " | " | H | OCF₂H | OCF₂H | CH | |
| 62 | " | " | " | H | OCH₃ | Br | CH | |
| 63 | " | " | " | H | OCH₃ | OC₂H₅ | CH | |
| 64 | " | " | " | H | OCH₃ | SCH₃ | CH | |
| 65 | " | " | " | H | OCH₃ | OC₂H₅ | N | |
| 66 | " | " | " | H | OCH₃ | OC₃H₇ | CH | |
| 67 | " | " | " | H | CH₃ | Cl | CH | |
| 68 | " | " | " | H | Cl | OC₂H₅ | CH | |
| 69 | " | " | " | H | OC₂H₅ | OC₂H₅ | CH | |
| 70 | " | " | " | H | C₂H₅ | OCH₃ | CH | |
| 71 | " | " | " | H | CF₃ | OCH₃ | CH | |
| 72 | " | " | " | H | OCH₂CF₃ | CH₃ | CH | |
| 73 | " | " | " | H | OCH₂CF₃ | OCH₃ | CH | |
| 74 | " | " | " | H | OCH₂CF₃ | OCH₂CF₃ | CH | |
| 75 | " | " | " | H | OCH₂CF₃ | OCH₃ | N | |
| 76 | " | " | " | H | OCH₃ | CH(OCH₃)₂ | CH | |
| 77 | " | " | " | CH₃ | OCH₃ | OCH₃ | CH | |
| 78 | " | " | " | CH₃ | OCH₃ | CH₃ | N | |
| 79 | " | CH₃ | COCH₃ | H | OCH₃ | OCH₃ | CH | |
| 80 | " | " | " | H | OCH₃ | CH₃ | CH | |
| 81 | " | " | " | H | CH₃ | CH₃ | CH | |
| 82 | " | " | " | H | CH₃ | OC₂H₅ | CH | |
| 83 | " | " | " | H | OCH₃ | OCH₃ | N | |
| 84 | " | " | " | H | OCH₃ | CH₃ | N | |
| 85 | " | " | " | H | OCH₃ | Cl | CH | |
| 86 | " | " | " | H | OCF₂H | CH₃ | CH | |
| 87 | " | " | " | H | OCF₂H | OCF₂H | CH | |
| 88 | " | " | " | H | OCH₃ | Br | CH | |
| 89 | " | " | " | H | OCH₃ | OC₂H₅ | CH | |
| 90 | " | " | " | H | OCH₃ | SCH₃ | CH | |
| 91 | " | " | " | H | OCH₃ | OC₂H₅ | N | |
| 92 | " | " | " | H | OCH₃ | OC₃H₇ | CH | |
| 93 | " | " | " | H | CH₃ | Cl | CH | |
| 94 | " | " | " | H | Cl | OC₂H₅ | CH | |
| 95 | " | " | " | H | OC₂H₅ | OC₂H₅ | CH | |
| 96 | " | " | " | H | C₂H₅ | OCH₃ | CH | |
| 97 | " | " | " | H | CF₃ | OCH₃ | CH | |
| 98 | " | " | " | H | OCH₂CF₃ | CH₃ | CH | |
| 99 | " | " | " | H | OCH₂CF₃ | OCH₃ | CH | |
| 100 | " | " | " | H | OCH₂CF₃ | OCH₂CF₃ | CH | |

TABLE 3-continued (Ic)

| CN | R¹ | R⁴ | R⁵ | R⁷ | X | Y | Z | Mp. °C. |
|---|---|---|---|---|---|---|---|---|
| 101 | " | " | " | H | OCH₂CF₃ | OCH₃ | N | |
| 102 | " | " | " | H | OCH₃ | CH(OCH₃)₂ | CH | |
| 103 | " | " | " | CH₃ | OCH₃ | OCH₃ | CH | |
| 104 | " | " | " | CH₃ | OCH₃ | CH₃ | N | |
| 105 | " | H | SO₂CH₃ | H | OCH₃ | OCH₃ | CH | |
| 106 | " | " | " | H | OCH₃ | CH₃ | CH | |
| 107 | " | " | " | H | CH₃ | CH₃ | CH | |
| 108 | " | " | " | H | OCH₃ | OCH₃ | N | |
| 109 | " | " | " | H | OCH₃ | CH₃ | N | |
| 110 | " | " | " | H | OC₂H₅ | NHCH₃ | N | |
| 111 | " | " | " | CH₃ | OCH₃ | OCH₃ | CH | |
| 112 | " | " | " | CH₃ | OCH₃ | CH₃ | N | |
| 113 | " | CH₃ | SO₂CH₃ | H | OCH₃ | OCH₃ | CH | |
| 114 | " | " | " | H | OCH₃ | CH₃ | CH | |
| 115 | " | " | " | H | CH₃ | CH₃ | CH | |
| 116 | " | " | " | H | OCH₃ | OCH₃ | N | |
| 117 | " | " | " | H | OCH₃ | CH₃ | N | |
| 118 | " | " | " | H | OC₂H₅ | NHCH₃ | N | |
| 119 | " | " | " | CH₃ | OCH₃ | OCH₃ | CH | |
| 120 | " | " | " | CH₃ | OCH₃ | CH₃ | N | |
| 121 | " | OH | CHO | H | OCH₃ | OCH₃ | CH | |
| 122 | " | " | " | H | OCH₃ | CH₃ | CH | |
| 123 | " | " | " | H | CH₃ | CH₃ | CH | |
| 124 | " | " | " | H | OCH₃ | OCH₃ | N | |
| 125 | " | " | " | H | OCH₃ | CH₃ | N | |
| 126 | " | " | " | H | OC₂H₅ | NHCH₃ | N | |
| 127 | " | " | " | CH₃ | OCH₃ | OCH₃ | CH | |
| 128 | " | " | " | CH₃ | OCH₃ | CH₃ | N | |
| 129 | " | OCH₃ | CHO | H | OCH₃ | OCH₃ | CH | |
| 130 | " | " | " | H | OCH₃ | CH₃ | CH | |
| 131 | " | " | " | H | CH₃ | CH₃ | CH | |
| 132 | " | " | " | H | OCH₃ | OCH₃ | N | |
| 133 | " | " | " | H | OCH₃ | CH₃ | N | |
| 134 | " | " | " | H | OC₂H₅ | NHCH₃ | N | |
| 135 | " | " | " | CH₃ | OCH₃ | OCH₃ | CH | |
| 136 | " | " | " | CH₃ | OCH₃ | CH₃ | N | |
| 137 | " | OH | COCH₃ | H | OCH₃ | OCH₃ | CH | |
| 138 | " | " | " | H | OCH₃ | CH₃ | CH | |
| 139 | " | " | " | H | CH₃ | CH₃ | CH | |
| 140 | " | " | " | H | OCH₃ | OCH₃ | N | |
| 141 | " | " | " | H | OCH₃ | CH₃ | N | |
| 142 | " | " | " | H | OC₂H₅ | NHCH₃ | N | |
| 143 | " | " | " | CH₃ | OCH₃ | OCH₃ | CH | |
| 144 | " | " | " | CH₃ | OCH₃ | CH₃ | N | |
| 145 | " | OCH₃ | COCH₃ | H | OCH₃ | OCH₃ | CH | |
| 146 | " | " | " | H | OCH₃ | CH₃ | CH | |
| 147 | " | " | " | H | CH₃ | CH₃ | CH | |
| 148 | " | " | " | H | OCH₃ | OCH₃ | N | |
| 149 | " | " | " | H | OCH₃ | CH₃ | N | |
| 150 | " | " | " | H | OC₂H₅ | NHCH₃ | N | |
| 151 | " | " | " | CH₃ | OCH₃ | OCH₃ | CH | |
| 152 | " | " | " | CH₃ | OCH₃ | CH₃ | N | |
| 153 | " | H | COC₂H₅ | H | OCH₃ | OCH₃ | CH | |
| 154 | " | " | " | H | OCH₃ | CH₃ | CH | |
| 155 | " | " | " | H | OCH₃ | OCH₃ | N | |
| 156 | " | " | " | H | OCH₃ | CH₃ | N | |
| 157 | " | CH₃ | " | H | OCH₃ | OCH₃ | CH | |
| 158 | " | " | " | H | OCH₃ | CH₃ | CH | |
| 159 | " | " | " | H | OCH₃ | OCH₃ | N | |
| 160 | " | " | " | H | OCH₃ | CH₃ | N | |
| 161 | " | H | COCH₂OCH₃ | H | OCH₃ | OCH₃ | CH | |
| 162 | " | " | " | H | OCH₃ | CH₃ | CH | |

TABLE 3-continued (Ic)

| CN | R¹ | R⁴ | R⁵ | R⁷ | X | Y | Z | Mp. °C. |
|---|---|---|---|---|---|---|---|---|
| 163 | " | " | " | H | OCH₃ | OCH₃ | N | |
| 164 | " | " | " | H | OCH₃ | CH₃ | N | |
| 165 | " | CH₃ | " | H | OCH₃ | OCH₃ | CH | |
| 166 | " | " | " | H | OCH₃ | CH₃ | CH | |
| 167 | " | " | " | H | OCH₃ | OCH₃ | N | |
| 168 | " | " | " | H | OCH₃ | CH₃ | N | |
| 169 | " | H | COCO₂C₂H₅ | H | OCH₃ | OCH₃ | CH | |
| 170 | " | " | " | H | OCH₃ | CH₃ | CH | |
| 171 | " | " | " | H | OCH₃ | OCH₃ | N | |
| 172 | " | " | " | H | OCH₃ | CH₃ | N | |
| 173 | " | CH₃ | " | H | OCH₃ | OCH₃ | CH | |
| 174 | " | " | " | H | OCH₃ | CH₃ | CH | |
| 175 | " | " | " | H | OCH₃ | OCH₃ | N | |
| 176 | " | " | " | H | OCH₃ | CH₃ | N | |
| 177 | " | H | COCF₃ | H | OCH₃ | OCH₃ | CH | |
| 178 | " | " | " | H | OCH₃ | CH₃ | CH | |
| 179 | " | " | " | H | OCH₃ | OCH₃ | N | |
| 180 | " | " | " | H | OCH₃ | CH₃ | N | |
| 181 | " | CH₃ | " | H | OCH₃ | OCH₃ | CH | |
| 182 | " | " | " | H | OCH₃ | CH₃ | CH | |
| 183 | " | " | " | H | OCH₃ | OCH₃ | N | |
| 184 | " | " | " | H | OCH₃ | CH₃ | N | |
| 185 | " | H | COOCH₃ | H | OCH₃ | OCH₃ | CH | |
| 186 | " | " | " | H | OCH₃ | CH₃ | CH | |
| 187 | " | " | " | H | OCH₃ | OCH₃ | N | |
| 188 | " | " | " | H | OCH₃ | CH₃ | N | |
| 189 | " | CH₃ | " | H | OCH₃ | OCH₃ | CH | |
| 190 | " | " | " | H | OCH₃ | CH₃ | CH | |
| 191 | " | " | " | H | OCH₃ | OCH₃ | N | |
| 192 | " | " | " | H | OCH₃ | CH₃ | N | |
| 193 | " | H | CONHC₂H₅ | H | OCH₃ | OCH₃ | CH | |
| 194 | " | " | " | H | OCH₃ | CH₃ | CH | |
| 195 | " | " | " | H | OCH₃ | OCH₃ | N | |
| 196 | " | " | " | H | OCH₃ | CH₃ | N | |
| 197 | " | CH₃ | " | H | OCH₃ | OCH₃ | CH | |
| 198 | " | " | " | H | OCH₃ | CH₃ | CH | |
| 199 | " | " | " | H | OCH₃ | OCH₃ | N | |
| 200 | " | " | " | H | OCH₃ | CH₃ | N | |
| 201 | " | H | CSNHC₂H₅ | H | OCH₃ | OCH₃ | CH | |
| 202 | " | " | " | H | OCH₃ | CH₃ | CH | |
| 203 | " | " | " | H | OCH₃ | OCH₃ | N | |
| 204 | " | " | " | H | OCH₃ | CH₃ | N | |
| 205 | " | CH₃ | " | H | OCH₃ | OCH₃ | CH | |
| 206 | " | " | " | H | OCH₃ | CH₃ | CH | |
| 207 | " | " | " | H | OCH₃ | OCH₃ | N | |
| 208 | " | " | " | H | OCH₃ | CH₃ | N | |
| 209 | " | H | SO₂NHCH₃ | H | OCH₃ | OCH₃ | CH | |
| 210 | " | " | " | H | OCH₃ | CH₃ | CH | |
| 211 | " | " | " | H | OCH₃ | OCH₃ | N | |
| 212 | " | " | " | H | OCH₃ | CH₃ | N | |
| 213 | " | CH₃ | " | H | OCH₃ | OCH₃ | CH | |
| 214 | " | " | " | H | OCH₃ | CH₃ | CH | |
| 215 | " | " | " | H | OCH₃ | OCH₃ | N | |
| 216 | " | " | " | H | OCH₃ | CH₃ | N | |
| 217 | " | H | SO₂N(CH₃)₂ | H | OCH₃ | OCH₃ | CH | |
| 218 | " | " | " | H | OCH₃ | CH₃ | CH | |
| 219 | " | " | " | H | OCH₃ | OCH₃ | N | |
| 220 | " | " | " | H | OCH₃ | CH₃ | N | |
| 221 | " | CH₃ | " | H | OCH₃ | OCH₃ | CH | |
| 222 | " | " | " | H | OCH₃ | CH₃ | CH | |
| 223 | " | " | " | H | OCH₃ | OCH₃ | N | |
| 224 | " | " | " | H | OCH₃ | CH₃ | N | |

TABLE 3-continued (Ic)

| CN | R¹ | R⁴ | R⁵ | R⁷ | X | Y | Z | Mp. °C. |
|---|---|---|---|---|---|---|---|---|
| 225 | " | | —CH₂CH₂CH₂CO— | H | OCH₃ | OCH₃ | CH | |
| 226 | " | | " | H | OCH₃ | CH₃ | CH | |
| 227 | " | | " | H | OCH₃ | OCH₃ | N | |
| 228 | " | | " | H | OCH₃ | CH₃ | N | |
| 229 | " | | —CH₂CH₂SO₂— | H | OCH₃ | OCH₃ | CH | |
| 230 | " | | " | H | OCH₃ | CH₃ | CH | |
| 231 | " | | " | H | OCH₃ | OCH₃ | N | |
| 232 | " | | " | H | OCH₃ | CH₃ | N | |
| 233 | " | | —CH₂CH₂CH₂CH₂CO— | H | OCH₃ | OCH₃ | CH | |
| 234 | " | | " | H | OCH₃ | CH₃ | CH | |
| 235 | " | | " | H | OCH₃ | OCH₃ | N | |
| 236 | " | | " | H | OCH₃ | CH₃ | N | |
| 237 | " | | —CH₂CH₂CH₂CH₂SO₂— | H | OCH₃ | OCH₃ | CH | |
| 238 | " | | " | H | OCH₃ | CH₃ | CH | |
| 239 | " | | " | H | OCH₃ | OCH₃ | N | |
| 240 | " | | " | H | OCH₃ | CH₃ | N | |
| 241 | " | | —CH₂CH₂OCH₂CH₂— | H | OCH₃ | OCH₃ | CH | |
| 242 | " | | " | H | OCH₃ | CH₃ | CH | |
| 243 | " | | " | H | OCH₃ | OCH₃ | N | |
| 244 | " | | " | H | OCH₃ | CH₃ | N | |
| 245 | " | H | COC₃H₇ | H | OCH₃ | OCH₃ | CH | |
| 246 | " | " | " | H | OCH₃ | CH₃ | CH | |
| 247 | " | " | " | H | OCH₃ | OCH₃ | N | |
| 248 | " | " | " | H | OCH₃ | CH₃ | N | |
| 249 | " | CH₃ | " | H | OCH₃ | OCH₃ | CH | |
| 250 | " | " | " | H | OCH₃ | CH₃ | CH | |
| 251 | " | " | " | H | OCH₃ | OCH₃ | N | |
| 252 | " | " | " | H | OCH₃ | CH₃ | N | |
| 253 | " | H | COCH₂Cl | H | OCH₃ | OCH₃ | CH | |
| 254 | " | " | " | H | OCH₃ | CH₃ | CH | |
| 255 | " | " | " | H | OCH₃ | OCH₃ | N | |
| 256 | " | " | " | H | OCH₃ | CH₃ | N | |
| 257 | " | CH₃ | " | H | OCH₃ | OCH₃ | CH | |
| 258 | " | " | " | H | OCH₃ | CH₃ | CH | |
| 259 | " | " | " | H | OCH₃ | OCH₃ | N | |
| 260 | " | " | " | H | OCH₃ | CH₃ | N | |
| 261 | " | H | COCHCl₂ | H | OCH₃ | OCH₃ | CH | |
| 262 | " | " | " | H | OCH₃ | CH₃ | CH | |
| 263 | " | " | " | H | OCH₃ | OCH₃ | N | |
| 264 | " | " | " | H | OCH₃ | CH₃ | N | |
| 265 | " | CH₃ | " | H | OCH₃ | OCH₃ | CH | |
| 266 | " | " | " | H | OCH₃ | CH₃ | CH | |
| 267 | " | " | " | H | OCH₃ | OCH₃ | N | |
| 268 | " | " | " | H | OCH₃ | CH₃ | N | |
| 269 | " | H | COCCl₃ | H | OCH₃ | OCH₃ | CH | |
| 270 | " | " | " | H | OCH₃ | CH₃ | CH | |
| 271 | " | " | " | H | OCH₃ | OCH₃ | N | |
| 272 | " | " | " | H | OCH₃ | CH₃ | N | |
| 273 | " | CH₃ | " | H | OCH₃ | OCH₃ | CH | |
| 274 | " | " | " | H | OCH₃ | CH₃ | CH | |
| 275 | " | " | " | H | OCH₃ | OCH₃ | N | |
| 276 | " | " | " | H | OCH₃ | CH₃ | N | |
| 277 | " | H | COCH=CH₂ | H | OCH₃ | OCH₃ | CH | |
| 278 | " | " | " | H | OCH₃ | CH₃ | CH | |
| 279 | " | " | " | H | OCH₃ | OCH₃ | N | |
| 280 | " | " | " | H | OCH₃ | CH₃ | N | |
| 281 | " | CH₃ | " | H | OCH₃ | OCH₃ | CH | |
| 282 | " | " | " | H | OCH₃ | CH₃ | CH | |
| 283 | " | " | " | H | OCH₃ | OCH₃ | N | |
| 284 | " | " | " | H | OCH₃ | CH₃ | N | |
| 285 | " | H | COC≡CH | H | OCH₃ | OCH₃ | CH | |
| 286 | " | " | " | H | OCH₃ | CH₃ | CH | |

TABLE 3-continued (Ic)

| CN | R¹ | R⁴ | R⁵ | R⁷ | X | Y | Z | Mp. °C. |
|---|---|---|---|---|---|---|---|---|
| 287 | " | " | " | H | OCH₃ | OCH₃ | N | |
| 288 | " | " | " | H | OCH₃ | CH₃ | N | |
| 289 | " | CH₃ | " | H | OCH₃ | OCH₃ | CH | |
| 290 | " | " | " | H | OCH₃ | CH₃ | CH | |
| 291 | " | " | " | H | OCH₃ | OCH₃ | N | |
| 292 | " | " | " | H | OCH₃ | CH₃ | N | |
| 293 | " | H | COC₆H₅ | H | OCH₃ | OCH₃ | CH | |
| 294 | " | " | " | H | OCH₃ | CH₃ | CH | |
| 295 | " | " | " | H | OCH₃ | OCH₃ | N | |
| 296 | " | " | " | H | OCH₃ | CH₃ | N | |
| 297 | " | CH₃ | " | H | OCH₃ | OCH₃ | CH | |
| 298 | " | " | " | H | OCH₃ | CH₃ | CH | |
| 299 | " | " | " | H | OCH₃ | OCH₃ | N | |
| 300 | " | " | " | H | OCH₃ | CH₃ | N | |
| 301 | " | SO₂C₆H₅ | SO₂C₆H₅ | H | OCH₃ | OCH₃ | CH | |
| 302 | " | " | " | H | OCH₃ | CH₃ | CH | |
| 303 | " | " | " | H | OCH₃ | OCH₃ | N | |
| 304 | " | " | " | H | OCH₃ | CH₃ | N | |
| 305 | " | SO₂CH₃ | SO₂CH₃ | H | OCH₃ | OCH₃ | CH | |
| 306 | " | " | " | H | OCH₃ | CH₃ | CH | |
| 307 | " | " | " | H | OCH₃ | OCH₃ | N | |
| 308 | " | " | " | H | OCH₃ | CH₃ | N | |
| 309 | " | H | COCH₂Br | H | OCH₃ | OCH₃ | CH | |
| 310 | " | " | " | H | OCH₃ | CH₃ | N | |
| 311 | " | CH₃ | " | H | OCH₃ | OCH₃ | CH | |
| 312 | " | " | " | H | OCH₃ | CH₃ | N | |
| 313 | " | H | COCH₂F | H | OCH₃ | OCH₃ | CH | |
| 314 | " | " | " | H | OCH₃ | CH₃ | N | |
| 315 | " | CH₃ | " | H | OCH₃ | OCH₃ | CH | |
| 316 | " | " | " | H | OCH₃ | CH₃ | N | |
| 317 | " | H | COCH₂C≡CH | H | OCH₃ | OCH₃ | CH | |
| 318 | " | " | " | H | OCH₃ | CH₃ | N | |
| 319 | " | CH₃ | " | H | OCH₃ | OCH₃ | CH | |
| 320 | " | " | " | H | OCH₃ | CH₃ | N | |
| 321 | " | H | COCO₂CH₃ | H | OCH₃ | OCH₃ | CH | |
| 322 | " | " | " | H | OCH₃ | CH₃ | N | |
| 323 | " | CH₃ | " | H | OCH₃ | OCH₃ | CH | |
| 324 | " | " | " | H | OCH₃ | CH₃ | N | |
| 325 | " | H | CO₂C₂H₅ | H | OCH₃ | OCH₃ | CH | |
| 326 | " | " | " | H | OCH₃ | CH₃ | N | |
| 327 | " | CH₃ | " | H | OCH₃ | OCH₃ | CH | |
| 328 | " | " | " | H | OCH₃ | CH₃ | N | |
| 329 | " | H | COSCH₃ | H | OCH₃ | OCH₃ | CH | |
| 330 | " | " | " | H | OCH₃ | CH₃ | N | |
| 331 | " | CH₃ | " | H | OCH₃ | OCH₃ | CH | |
| 332 | " | " | " | H | OCH₃ | CH₃ | N | |
| 333 | " | H | CSOCH₃ | H | OCH₃ | OCH₃ | CH | |
| 334 | " | " | " | H | OCH₃ | CH₃ | N | |
| 335 | " | CH₃ | " | H | OCH₃ | OCH₃ | CH | |
| 336 | " | " | " | H | OCH₃ | CH₃ | N | |
| 337 | " | H | CSSCH₃ | H | OCH₃ | OCH₃ | CH | |
| 338 | " | " | " | H | OCH₃ | CH₃ | N | |
| 339 | " | CH₃ | " | H | OCH₃ | OCH₃ | CH | |
| 340 | " | " | " | H | OCH₃ | CH₃ | N | |
| 341 | " | H | COCH(CH₃)₂ | H | OCH₃ | OCH₃ | CH | |
| 342 | " | " | " | H | OCH₃ | CH₃ | N | |
| 343 | " | CH₃ | " | H | OCH₃ | OCH₃ | CH | |
| 344 | " | " | " | H | OCH₃ | CH₃ | N | |
| 345 | " | H | COC(CH₃)₃ | H | OCH₃ | OCH₃ | CH | |
| 346 | " | " | " | H | OCH₃ | CH₃ | N | |
| 347 | " | CH₃ | " | H | OCH₃ | OCH₃ | CH | |
| 348 | " | " | " | H | OCH₃ | CH₃ | N | |

TABLE 3-continued (Ic)

| CN | R¹ | R⁴ | R⁵ | R⁷ | X | Y | Z | Mp. ° C. |
|---|---|---|---|---|---|---|---|---|
| 349 | " | H | CO-Cyclopropyl | H | OCH₃ | OCH₃ | CH | |
| 350 | " | " | " | H | OCH₃ | CH₃ | N | |
| 351 | " | CH₃ | " | H | OCH₃ | OCH₃ | CH | |
| 352 | " | " | " | H | OCH₃ | CH₃ | N | |
| 353 | " | H | CO-Cyclobutyl | H | OCH₃ | OCH₃ | CH | |
| 354 | " | " | " | H | OCH₃ | CH₃ | N | |
| 355 | " | CH₃ | " | H | OCH₃ | OCH₃ | CH | |
| 356 | " | " | " | H | OCH₃ | CH₃ | N | |
| 357 | " | H | CO-Cyclopentyl | H | OCH₃ | OCH₃ | CH | |
| 358 | " | " | " | H | OCH₃ | CH₃ | N | |
| 359 | " | CH₃ | " | H | OCH₃ | OCH₃ | CH | |
| 360 | " | " | " | H | OCH₃ | CH₃ | N | |
| 361 | " | H | CO-Cyclohexyl | H | OCH₃ | OCH₃ | CH | |
| 362 | " | " | " | H | OCH₃ | CH₃ | N | |
| 363 | " | CH₃ | " | H | OCH₃ | OCH₃ | CH | |
| 364 | " | " | " | H | OCH₃ | CH₃ | N | |
| 365 | " | H | CONHCH₂CH₂Cl | H | OCH₃ | OCH₃ | CH | |
| 366 | " | " | " | H | OCH₃ | CH₃ | N | |
| 367 | " | CH₃ | " | H | OCH₃ | OCH₃ | CH | |
| 368 | " | " | " | H | OCH₃ | CH₃ | N | |
| 369 | " | H | CSNHCH₂CH₂Cl | H | OCH₃ | OCH₃ | CH | |
| 370 | " | " | " | H | OCH₃ | CH₃ | N | |
| 371 | " | CH₃ | " | H | OCH₃ | OCH₃ | CH | |
| 372 | " | " | " | H | OCH₃ | CH₃ | N | |
| 373 | " | H | CONH-n-C₄H₉ | H | OCH₃ | OCH₃ | CH | |
| 374 | " | " | " | H | OCH₃ | CH₃ | N | |
| 375 | " | CH₃ | " | H | OCH₃ | OCH₃ | CH | |
| 376 | " | " | " | H | OCH₃ | CH₃ | N | |
| 377 | " | H | CSNHCH₃ | H | OCH₃ | OCH₃ | CH | |
| 378 | " | " | " | H | OCH₃ | CH₃ | N | |
| 379 | " | CH₃ | " | H | OCH₃ | OCH₃ | CH | |
| 380 | " | " | " | H | OCH₃ | CH₃ | N | |
| 381 | " | H | CSNHCH₂CH=CH₂ | H | OCH₃ | OCH₃ | CH | |
| 382 | " | " | " | H | OCH₃ | CH₃ | N | |
| 383 | " | CH₃ | " | H | OCH₃ | OCH₃ | CH | |
| 384 | " | " | " | H | OCH₃ | CH₃ | N | |
| 385 | " | CH₃ | CSNHCH₂COCH₃ | H | OCH₃ | OCH₃ | CH | |
| 386 | " | " | " | H | OCH₃ | CH₃ | N | |
| 387 | " | CH₃ | CSNHCH₂COC₂H₅ | H | OCH₃ | OCH₃ | CH | |
| 388 | " | " | " | H | OCH₃ | CH₃ | N | |
| 389 | " | CH₃ | CONHCH₂COCH₃ | H | OCH₃ | OCH₃ | CH | |
| 390 | " | " | " | H | OCH₃ | CH₃ | N | |
| 391 | " | CH₃ | CONHCH₂COC₂H₅ | H | OCH₃ | OCH₃ | CH | |
| 392 | " | " | " | H | OCH₃ | CH₃ | N | |
| 393 | " | | —CONHCH₂CO— | H | OCH₃ | OCH₃ | CH | |
| 394 | " | | " | H | OCH₃ | CH₃ | N | |
| 395 | " | H | SO₂CH₂F | H | OCH₃ | OCH₃ | CH | |
| 396 | " | " | " | H | OCH₃ | CH₃ | N | |
| 397 | " | CH₃ | " | H | OCH₃ | OCH₃ | CH | |
| 398 | " | " | " | H | OCH₃ | CH₃ | N | |
| 399 | " | H | SO₂CF₃ | H | OCH₃ | OCH₃ | CH | |
| 400 | " | " | " | H | OCH₃ | CH₃ | N | |
| 401 | " | CH₃ | " | H | OCH₃ | OCH₃ | CH | |
| 402 | " | " | " | H | OCH₃ | CH₃ | N | |
| 403 | " | H | SO₂C₂H₅ | H | OCH₃ | OCH₃ | CH | |
| 404 | " | " | " | H | OCH₃ | CH₃ | N | |
| 405 | " | CH₃ | " | H | OCH₃ | OCH₃ | CH | |
| 406 | " | " | " | H | OCH₃ | CH₃ | N | |
| 407 | " | H | SO₂-n-C₃H₇ | H | OCH₃ | OCH₃ | CH | |
| 408 | " | " | " | H | OCH₃ | CH₃ | N | |
| 409 | " | CH₃ | " | H | OCH₃ | OCH₃ | CH | |
| 410 | " | " | " | H | OCH₃ | CH₃ | N | |

TABLE 3-continued (Ic)

| CN | R¹ | R⁴ | R⁵ | R⁷ | X | Y | Z | Mp. °C. |
|---|---|---|---|---|---|---|---|---|
| 411 | " | OH | COC₂H₅ | H | OCH₃ | OCH₃ | CH | |
| 412 | " | " | " | H | OCH₃ | CH₃ | N | |
| 413 | " | OCH₃ | " | H | OCH₃ | OCH₃ | CH | |
| 414 | " | " | " | H | OCH₃ | CH₃ | N | |
| 415 | " | OH | COCH₂Cl | H | OCH₃ | OCH₃ | CH | |
| 416 | " | " | " | H | OCH₃ | CH₃ | N | |
| 417 | " | OCH₃ | " | H | OCH₃ | OCH₃ | CH | |
| 418 | " | " | " | H | OCH₃ | CH₃ | N | |
| 419 | " | OH | COCF₃ | H | OCH₃ | OCH₃ | CH | |
| 420 | " | " | " | H | OCH₃ | CH₃ | N | |
| 421 | " | OCH₃ | " | H | OCH₃ | OCH₃ | CH | |
| 422 | " | " | " | H | OCH₃ | CH₃ | N | |
| 423 | " | OH | COCH₂OCH₃ | H | OCH₃ | OCH₃ | CH | |
| 424 | " | " | " | H | OCH₃ | CH₃ | N | |
| 425 | " | OCH₃ | " | H | OCH₃ | OCH₃ | CH | |
| 426 | " | " | " | H | OCH₃ | CH₃ | N | |
| 427 | " | OH | COCO₂C₂H₅ | H | OCH₃ | OCH₃ | CH | |
| 428 | " | " | " | H | OCH₃ | CH₃ | N | |
| 429 | " | OCH₃ | " | H | OCH₃ | OCH₃ | CH | |
| 430 | " | " | " | H | OCH₃ | CH₃ | N | |
| 431 | " | OH | COOCH₃ | H | OCH₃ | OCH₃ | CH | |
| 432 | " | " | " | H | OCH₃ | CH₃ | N | |
| 433 | " | OCH₃ | " | H | OCH₃ | OCH₃ | CH | |
| 434 | " | " | " | H | OCH₃ | CH₃ | N | |
| 435 | " | OH | Cyclopropyl | H | OCH₃ | OCH₃ | CH | |
| 436 | " | " | " | H | OCH₃ | CH₃ | N | |
| 437 | " | OCH₃ | " | H | OCH₃ | OCH₃ | CH | |
| 438 | " | " | " | H | OCH₃ | CH₃ | N | |
| 439 | " | OH | COC₆H₅ | H | OCH₃ | OCH₃ | CH | |
| 440 | " | " | " | H | OCH₃ | CH₃ | N | |
| 441 | " | OCH₃ | " | H | OCH₃ | OCH₃ | CH | |
| 442 | " | " | " | H | OCH₃ | CH₃ | N | |
| 443 | " | OH | COCH(CH₃)₂ | H | OCH₃ | OCH₃ | CH | |
| 444 | " | " | " | H | OCH₃ | CH₃ | N | |
| 445 | " | OCH₃ | " | H | OCH₃ | OCH₃ | CH | |
| 446 | " | " | " | H | OCH₃ | CH₃ | N | |
| 447 | " | OH | COCH=CH₂ | H | OCH₃ | OCH₃ | CH | |
| 448 | " | " | " | H | OCH₃ | CH₃ | N | |
| 449 | " | OCH₃ | " | H | OCH₃ | OCH₃ | CH | |
| 450 | " | " | " | H | OCH₃ | CH₃ | N | |
| 451 | " | OH | COC≡CH | H | OCH₃ | OCH₃ | CH | |
| 452 | " | " | " | H | OCH₃ | CH₃ | N | |
| 453 | " | OCH₃ | " | H | OCH₃ | OCH₃ | CH | |
| 454 | " | " | " | H | OCH₃ | CH₃ | N | |
| 455 | " | OH | SO₂CH₃ | H | OCH₃ | OCH₃ | CH | |
| 456 | " | " | " | H | OCH₃ | CH₃ | N | |
| 457 | " | OCH₃ | " | H | OCH₃ | OCH₃ | CH | |
| 458 | " | " | " | H | OCH₃ | CH₃ | N | |
| 459 | " | OH | SO₂NHCH₃ | H | OCH₃ | OCH₃ | CH | |
| 460 | " | " | " | H | OCH₃ | CH₃ | N | |
| 461 | " | OCH₃ | " | H | OCH₃ | OCH₃ | CH | |
| 462 | " | " | " | H | OCH₃ | CH₃ | N | |
| 463 | " | OH | SO₂N(CH₃)₂ | H | OCH₃ | OCH₃ | CH | |
| 464 | " | " | " | H | OCH₃ | CH₃ | N | |
| 465 | " | OCH₃ | " | H | OCH₃ | OCH₃ | CH | |
| 466 | " | " | " | H | OCH₃ | CH₃ | N | |
| 467 | " | C₂H₅ | CHO | H | OCH₃ | OCH₃ | CH | |
| 468 | " | " | " | H | OCH₃ | CH₃ | N | |
| 469 | " | " | COCH₃ | H | OCH₃ | OCH₃ | CH | |
| 470 | " | " | " | H | OCH₃ | CH₃ | N | |
| 471 | " | " | Cyclopropyl | H | OCH₃ | OCH₃ | CH | |
| 472 | " | " | " | H | OCH₃ | CH₃ | N | |

TABLE 3-continued (Ic)

| CN | R¹ | R⁴ | R⁵ | R⁷ | X | Y | Z | Mp. °C. |
|---|---|---|---|---|---|---|---|---|
| 473 | " | " | COCH₂Cl | H | OCH₃ | OCH₃ | CH | |
| 474 | " | " | " | H | OCH₃ | CH₃ | N | |
| 475 | " | " | COCF₃ | H | OCH₃ | OCH₃ | CH | |
| 476 | " | " | " | H | OCH₃ | CH₃ | N | |
| 477 | " | " | COOCH₃ | H | OCH₃ | OCH₃ | CH | |
| 478 | " | " | " | H | OCH₃ | CH₃ | N | |
| 479 | " | " | COC₆H₅ | H | OCH₃ | OCH₃ | CH | |
| 480 | " | " | " | H | OCH₃ | CH₃ | N | |
| 481 | " | " | CONHC₂H₅ | H | OCH₃ | OCH₃ | CH | |
| 482 | " | " | " | H | OCH₃ | CH₃ | N | |
| 483 | " | " | CSNHC₂H₅ | H | OCH₃ | OCH₃ | CH | |
| 484 | " | " | " | H | OCH₃ | CH₃ | N | |
| 485 | " | " | SO₂CH₃ | H | OCH₃ | OCH₃ | CH | |
| 486 | " | " | " | H | OCH₃ | CH₃ | N | |
| 487 | " | " | SO₂NHCH₃ | H | OCH₃ | OCH₃ | CH | |
| 488 | " | " | " | H | OCH₃ | CH₃ | N | |
| 489 | " | " | SO₂N(CH₃)₂ | H | OCH₃ | OCH₃ | CH | |
| 490 | " | " | " | H | OCH₃ | CH₃ | N | |
| 491 | " | " | SO₂C₆H₅ | H | OCH₃ | OCH₃ | CH | |
| 492 | " | " | " | H | OCH₃ | CH₃ | N | |
| 493 | CO₂C₂H₅ | H | CHO | H | OCH₃ | OCH₃ | CH | |
| 494 | " | " | " | H | OCH₃ | CH₃ | N | |
| 495 | " | " | COCH₃ | H | OCH₃ | OCH₃ | CH | |
| 496 | " | " | " | H | OCH₃ | CH₃ | N | |
| 497 | " | " | SO₂CH₃ | H | OCH₃ | OCH₃ | CH | |
| 498 | " | " | " | H | OCH₃ | CH₃ | N | |
| 499 | " | CH₃ | CHO | H | OCH₃ | OCH₃ | CH | |
| 500 | " | " | " | H | OCH₃ | CH₃ | N | |
| 501 | " | " | COCH₃ | H | OCH₃ | OCH₃ | CH | |
| 502 | " | " | " | H | OCH₃ | CH₃ | N | |
| 503 | " | " | SO₂CH₃ | H | OCH₃ | OCH₃ | CH | |
| 504 | " | " | " | H | OCH₃ | CH₃ | N | |
| 505 | " | C₂H₅ | CHO | H | OCH₃ | OCH₃ | CH | |
| 506 | " | " | " | H | OCH₃ | CH₃ | N | |
| 507 | " | " | COCH₃ | H | OCH₃ | OCH₃ | CH | |
| 508 | " | " | " | H | OCH₃ | CH₃ | N | |
| 509 | " | " | SO₂CH₃ | H | OCH₃ | OCH₃ | CH | |
| 510 | " | " | " | H | OCH₃ | CH₃ | N | |
| 511 | " | OH | CHO | H | OCH₃ | OCH₃ | CH | |
| 512 | " | " | " | H | OCH₃ | CH₃ | N | |
| 513 | " | " | COCH₃ | H | OCH₃ | OCH₃ | CH | |
| 514 | " | " | " | H | OCH₃ | CH₃ | N | |
| 515 | " | " | SO₂CH₃ | H | OCH₃ | OCH₃ | CH | |
| 516 | " | " | " | H | OCH₃ | CH₃ | N | |
| 517 | " | OCH₃ | CHO | H | OCH₃ | OCH₃ | CH | |
| 518 | " | " | " | H | OCH₃ | CH₃ | N | |
| 519 | " | " | COCH₃ | H | OCH₃ | OCH₃ | CH | |
| 520 | " | " | " | H | OCH₃ | CH₃ | N | |
| 521 | CO₂-n-Bu | H | CHO | H | OCH₃ | OMe | CH | |
| 522 | CONMe₂ | Me | " | H | OCH₃ | Me | N | |
| 523 | CONHMe | H | " | H | OCH₃ | OMe | CH | |
| 524 | COSMe | Me | CO—Me | H | Me | CH₃ | N | |
| 525 | COOMe | n-Bu | CHO | H | OCH₃ | OMe | CH | |
| 526 | " | " | " | H | OCH₃ | Me | N | |
| 527 | " | H | " | H | OCH₂CF₃ | NMe₂ | N | |
| 528 | " | Me | " | H | " | " | " | |
| 529 | " | H | CO—Me | H | " | " | " | |
| 530 | " | Me | " | H | " | " | " | |
| 531 | " | " | SO₂CH₃ | H | OCH₃ | OCH₃ | CH | |
| 532 | " | " | " | H | OCH₃ | CH₃ | N | |

TABLE 3-continued (Ic)

| CN | $R^1$ | $R^4$ | $R^5$ | $R^7$ | X | Y | Z | Mp. °C. |
|---|---|---|---|---|---|---|---|---|
| 533 | " | | CH₃-C=CH-CH=C-CH₃ (CH₃)(CH₃) | H | OCH₃ | OCH₃ | CH | |
| 534 | " | | CH₃-C=CH-CH=C-CH₃ (CH₃)(CH₃) | H | OCH₃ | CH₃ | N | |
| 535 | CO₂CH₃ | H | COCH₃ | H | OCH₃ | OCH₃ | CH | Na-Salt: 270 |

TABLE 4

(Id)

| CN | $R^1$ | $R^4$ | $R^5$ | $R^7$ | X | Y | Z | Mp. °C. |
|---|---|---|---|---|---|---|---|---|
| 1 | CO₂CH₃ | H | CHO | H | OCH₃ | OCH₃ | CH | |
| 2 | " | " | " | H | OCH₃ | CH₃ | CH | |
| 3 | " | " | " | H | CH₃ | CH₃ | CH | |
| 4 | " | " | " | H | CH₃ | OC₂H₅ | CH | |
| 5 | " | " | " | H | OCH₃ | OCH₃ | N | |
| 6 | " | " | " | H | OCH₃ | CH₃ | N | |
| 7 | " | " | " | H | OCH₃ | Cl | CH | |
| 8 | " | " | " | H | OCF₂H | CH₃ | CH | |
| 9 | " | " | " | H | OCF₂H | OCF₂H | CH | |
| 10 | " | " | " | H | OCH₃ | Br | CH | |
| 11 | " | " | " | H | OCH₃ | OC₂H₅ | CH | |
| 12 | " | " | " | H | OCH₃ | SCH₃ | CH | |
| 13 | " | " | " | H | OCH₃ | OC₂H₅ | N | |
| 14 | " | " | " | H | OCH₃ | OC₃H₇ | CH | |
| 15 | " | " | " | H | CH₃ | Cl | CH | |
| 16 | " | " | " | H | Cl | OC₂H₅ | CH | |
| 17 | " | " | " | H | OC₂H₅ | OC₂H₅ | CH | |
| 18 | " | " | " | H | C₂H₅ | OCH₃ | CH | |
| 19 | " | " | " | H | CF₃ | OCH₃ | CH | |
| 20 | " | " | " | H | OCH₂CF₃ | CH₃ | CH | |
| 21 | " | " | " | H | OCH₂CF₃ | OCH₃ | CH | |
| 22 | " | " | " | H | OCH₂CF₃ | OCH₂CF₃ | CH | |
| 23 | " | " | " | H | OCH₂CF₃ | OCH₃ | N | |
| 24 | " | " | " | H | OCH₃ | CH(OCH₃)₂ | CH | |
| 25 | " | " | " | CH₃ | OCH₃ | OCH₃ | CH | |
| 26 | " | " | " | CH₃ | OCH₃ | CH₃ | N | |
| 27 | " | H | COCH₃ | H | OCH₃ | OCH₃ | CH | |

TABLE 4-continued (Id)

| CN | R¹ | R⁴ | R⁵ | R⁷ | X | Y | Z | Mp. °C. |
|---|---|---|---|---|---|---|---|---|
| 28 | " | " | " | H | OCH₃ | CH₃ | CH | |
| 29 | " | " | " | H | CH₃ | CH₃ | CH | |
| 30 | " | " | " | H | CH₃ | OC₂H₅ | CH | |
| 31 | " | " | " | H | OCH₃ | OCH₃ | N | |
| 32 | " | " | " | H | OCH₃ | CH₃ | N | |
| 33 | " | " | " | H | OCH₃ | Cl | CH | |
| 34 | " | " | " | H | OCF₂H | CH₃ | CH | |
| 35 | " | " | " | H | OCF₂H | OCF₂H | CH | |
| 36 | " | " | " | H | OCH₃ | Br | CH | |
| 37 | " | " | " | H | OCH₃ | OC₂H₅ | CH | |
| 38 | " | " | " | H | OCH₃ | SCH₃ | CH | |
| 39 | " | " | " | H | OCH₃ | OC₂H₅ | N | |
| 40 | " | " | " | H | OCH₃ | OC₃H₇ | CH | |
| 41 | " | " | " | H | CH₃ | Cl | CH | |
| 42 | " | " | " | H | Cl | OC₂H₅ | CH | |
| 43 | " | " | " | H | OC₂H₅ | OC₂H₅ | CH | |
| 44 | " | " | " | H | C₂H₅ | OCH₃ | CH | |
| 45 | " | " | " | H | CF₃ | OCH₃ | CH | |
| 46 | " | " | " | H | OCH₂CF₃ | CH₃ | CH | |
| 47 | " | " | " | H | OCH₂CF₃ | OCH₃ | CH | |
| 48 | " | " | " | H | OCH₂CF₃ | OCH₂CF₃ | CH | |
| 49 | " | " | " | H | OCH₂CF₃ | OCH₃ | N | |
| 50 | " | " | " | H | OCH₃ | CH(OCH₃)₂ | CH | |
| 51 | " | " | " | CH₃ | OCH₃ | OCH₃ | CH | |
| 52 | " | " | " | CH₃ | OCH₃ | CH₃ | N | |
| 53 | " | CH₃ | CHO | H | OCH₃ | OCH₃ | CH | 150–151 |
| 54 | " | " | " | H | OCH₃ | CH₃ | CH | |
| 55 | " | " | " | H | CH₃ | CH₃ | CH | |
| 56 | " | " | " | H | CH₃ | OC₂H₅ | CH | |
| 57 | " | " | " | H | OCH₃ | OCH₃ | N | |
| 58 | " | " | " | H | OCH₃ | CH₃ | N | |
| 59 | " | " | " | H | OCH₃ | Cl | CH | |
| 60 | " | " | " | H | OCF₂H | CH₃ | CN | |
| 61 | " | " | " | H | OCF₂H | OCF₂H | CH | |
| 62 | " | " | " | H | OCH₃ | Br | CH | |
| 63 | " | " | " | H | OCH₃ | OC₂H₅ | CH | |
| 64 | " | " | " | H | OCH₃ | SCH₃ | CH | |
| 65 | " | " | " | H | OCH₃ | OC₂H₅ | N | |
| 66 | " | " | " | H | OCH₃ | OC₃H₇ | CH | |
| 67 | " | " | " | H | CH₃ | Cl | CH | |
| 68 | " | " | " | H | Cl | OC₂H₅ | CH | |
| 69 | " | " | " | H | OC₂H₅ | OC₂H₅ | CH | |
| 70 | " | " | " | H | C₂H₅ | OCH₃ | CH | |
| 71 | " | " | " | H | CF₃ | OCH₃ | CH | |
| 72 | " | " | " | H | OCH₂CF₃ | CH₃ | CH | |
| 73 | " | " | " | H | OCH₂CF₃ | OCH₃ | CH | |
| 74 | " | " | " | H | OCH₂CF₃ | OCH₂CF₃ | CH | |
| 75 | " | " | " | H | OCH₂CF₃ | OCH₃ | N | |
| 76 | " | " | " | H | OCH₃ | CH(OCH₃)₂ | CH | |
| 77 | " | " | " | CH₃ | OCH₃ | OCH₃ | CH | |
| 78 | " | " | " | CH₃ | OCH₃ | CH₃ | N | |
| 79 | " | CH₃ | COCH₃ | H | OCH₃ | OCH₃ | CH | |
| 80 | " | " | " | H | OCH₃ | CH₃ | CH | |
| 81 | " | " | " | H | CH₃ | CH₃ | CH | |
| 82 | " | " | " | H | CH₃ | OC₂H₅ | CH | |
| 83 | " | " | " | H | OCH₃ | OCH₃ | N | |
| 84 | " | " | " | H | OCH₃ | CH₃ | N | |
| 85 | " | " | " | H | OCH₃ | Cl | CH | |
| 86 | " | " | " | H | OCF₂H | CH₃ | CH | |
| 87 | " | " | " | H | OCF₂H | OCF₂H | CH | |
| 88 | " | " | " | H | OCH₃ | Br | CH | |
| 89 | " | " | " | H | OCH₃ | OC₂H₅ | CH | |
| 90 | " | " | " | H | OCH₃ | SCH₃ | CH | |

TABLE 4-continued (Id)

| CN | R¹ | R⁴ | R⁵ | R⁷ | X | Y | Z | Mp. °C. |
|---|---|---|---|---|---|---|---|---|
| 91 | " | " | " | H | OCH₃ | OC₂H₅ | N | |
| 92 | " | " | " | H | OCH₃ | OC₃H₇ | CH | |
| 93 | " | " | " | H | CH₃ | Cl | CH | |
| 94 | " | " | " | H | Cl | OC₂H₅ | CH | |
| 95 | " | " | " | H | OC₂H₅ | OC₂H₅ | CH | |
| 96 | " | " | " | H | C₂H₅ | OCH₃ | CH | |
| 97 | " | " | " | H | CF₃ | OCH₃ | CH | |
| 98 | " | " | " | H | OCH₂CF₃ | CH₃ | CH | |
| 99 | " | " | " | H | OCH₂CF₃ | OCH₃ | CH | |
| 100 | " | " | " | H | OCH₂CF₃ | OCH₂CF₃ | CH | |
| 101 | " | " | " | H | OCH₂CF₃ | OCH₃ | N | |
| 102 | " | " | " | H | OCH₃ | CH(OCH₃)₂ | CH | |
| 103 | " | " | " | CH₃ | OCH₃ | OCH₃ | CH | |
| 104 | " | " | " | CH₃ | OCH₃ | CH₃ | N | |
| 105 | " | H | SO₂CH₃ | H | OCH₃ | OCH₃ | CH | |
| 106 | " | " | " | H | OCH₃ | CH₃ | CH | |
| 107 | " | " | " | H | CH₃ | CH₃ | CH | |
| 108 | " | " | " | H | OCH₃ | OCH₃ | N | |
| 109 | " | " | " | H | OCH₃ | CH₃ | N | |
| 110 | " | " | " | H | OC₂H₅ | NHCH₃ | N | |
| 111 | " | " | " | CH₃ | OCH₃ | OCH₃ | CH | |
| 112 | " | " | " | CH₃ | OCH₃ | CH₃ | N | |
| 113 | " | CH₃ | SO₂CH₃ | H | OCH₃ | OCH₃ | CH | |
| 114 | " | " | " | H | OCH₃ | CH₃ | CH | |
| 115 | " | " | " | H | CH₃ | CH₃ | CH | |
| 116 | " | " | " | H | OCH₃ | OCH₃ | N | |
| 117 | " | " | " | H | OCH₃ | CH₃ | N | |
| 118 | " | " | " | H | OC₂H₅ | NHCH₃ | N | |
| 119 | " | " | " | CH₃ | OCH₃ | OCH₃ | CH | |
| 120 | " | " | " | CH₃ | OCH₃ | CH₃ | N | |
| 121 | " | OH | CHO | H | OCH₃ | OCH₃ | CH | |
| 122 | " | " | " | H | OCH₃ | CH₃ | CH | |
| 123 | " | " | " | H | CH₃ | CH₃ | CH | |
| 124 | " | " | " | H | OCH₃ | OCH₃ | N | |
| 125 | " | " | " | H | OCH₃ | CH₃ | N | |
| 126 | " | " | " | H | OC₂H₅ | NHCH₃ | N | |
| 127 | " | " | " | CH₃ | OCH₃ | OCH₃ | CH | |
| 128 | " | " | " | CH₃ | OCH₃ | CH₃ | N | |
| 129 | " | OCH₃ | CHO | H | OCH₃ | OCH₃ | CH | |
| 130 | " | " | " | H | OCH₃ | CH₃ | CH | |
| 131 | " | " | " | H | CH₃ | CH₃ | CH | |
| 132 | " | " | " | H | OCH₃ | OCH₃ | N | |
| 133 | " | " | " | H | OCH₃ | CH₃ | N | |
| 134 | " | " | " | H | OC₂H₅ | NHCH₃ | N | |
| 135 | " | " | " | CH₃ | OCH₃ | OCH₃ | CH | |
| 136 | " | " | " | CH₃ | OCH₃ | CH₃ | N | |
| 137 | " | OH | COCH₃ | H | OCH₃ | OCH₃ | CH | |
| 138 | " | " | " | H | OCH₃ | CH₃ | CH | |
| 139 | " | " | " | H | CH₃ | CH₃ | CH | |
| 140 | " | " | " | H | OCH₃ | OCH₃ | N | |
| 141 | " | " | " | H | OCH₃ | CH₃ | N | |
| 142 | " | " | " | H | OC₂H₅ | NHCH₃ | N | |
| 143 | " | " | " | CH₃ | OCH₃ | OCH₃ | CH | |
| 144 | " | " | " | CH₃ | OCH₃ | CH₃ | N | |
| 145 | " | OCH₃ | COCH₃ | H | OCH₃ | OCH₃ | CH | |
| 146 | " | " | " | H | OCH₃ | CH₃ | CH | |
| 147 | " | " | " | H | CH₃ | CH₃ | CH | |
| 148 | " | " | " | H | OCH₃ | OCH₃ | N | |
| 149 | " | " | " | H | OCH₃ | CH₃ | N | |
| 150 | " | " | " | H | OC₂H₅ | NHCH₃ | N | |
| 151 | " | " | " | CH₃ | OCH₃ | OCH₃ | CH | |
| 152 | " | " | " | CH₃ | OCH₃ | CH₃ | N | |
| 153 | " | H | COC₂H₅ | H | OCH₃ | OCH₃ | CH | |

TABLE 4-continued (Id)

| CN | R¹ | R⁴ | R⁵ | R⁷ | X | Y | Z | Mp. °C. |
|---|---|---|---|---|---|---|---|---|
| 154 | " | " | " | H | OCH₃ | CH₃ | CH | |
| 155 | " | " | " | H | OCH₃ | OCH₃ | N | |
| 156 | " | " | " | H | OCH₃ | CH₃ | N | |
| 157 | " | CH₃ | " | H | OCH₃ | OCH₃ | CH | |
| 158 | " | " | " | H | OCH₃ | CH₃ | CH | |
| 159 | " | " | " | H | OCH₃ | OCH₃ | N | |
| 160 | " | " | " | H | OCH₃ | CH₃ | N | |
| 161 | " | H | COCH₂OCH₃ | H | OCH₃ | OCH₃ | CH | |
| 162 | " | " | " | H | OCH₃ | CH₃ | CH | |
| 163 | " | " | " | H | OCH₃ | OCH₃ | N | |
| 164 | " | " | " | H | OCH₃ | CH₃ | N | |
| 165 | " | CH₃ | " | H | OCH₃ | OCH₃ | CH | |
| 166 | " | " | " | H | OCH₃ | CH₃ | CH | |
| 167 | " | " | " | H | OCH₃ | OCH₃ | N | |
| 168 | " | " | " | H | OCH₃ | CH₃ | N | |
| 169 | " | H | COCO₂C₂H₅ | H | OCH₃ | OCH₃ | CH | |
| 170 | " | " | " | H | OCH₃ | CH₃ | CH | |
| 171 | " | " | " | H | OCH₃ | OCH₃ | N | |
| 172 | " | " | " | H | OCH₃ | CH₃ | N | |
| 173 | " | CH₃ | " | H | OCH₃ | OCH₃ | CH | |
| 174 | " | " | " | H | OCH₃ | CH₃ | CH | |
| 175 | " | " | " | H | OCH₃ | OCH₃ | N | |
| 176 | " | " | " | H | OCH₃ | CH₃ | N | |
| 177 | " | H | COCF₃ | H | OCH₃ | OCH₃ | CH | |
| 178 | " | " | " | H | OCH₃ | CH₃ | CH | |
| 179 | " | " | " | H | OCH₃ | OCH₃ | N | |
| 180 | " | " | " | H | OCH₃ | CH₃ | N | |
| 181 | " | CH₃ | " | H | OCH₃ | OCH₃ | CH | |
| 182 | " | " | " | H | OCH₃ | CH₃ | CH | |
| 183 | " | " | " | H | OCH₃ | OCH₃ | N | |
| 184 | " | " | " | H | OCH₃ | CH₃ | N | |
| 185 | " | H | COOCH₃ | H | OCH₃ | OCH₃ | CH | |
| 186 | " | " | " | H | OCH₃ | CH₃ | CH | |
| 187 | " | " | " | H | OCH₃ | OCH₃ | N | |
| 188 | " | " | " | H | OCH₃ | CH₃ | N | |
| 189 | " | CH₃ | " | H | OCH₃ | OCH₃ | CH | |
| 190 | " | " | " | H | OCH₃ | CH₃ | CH | |
| 191 | " | " | " | H | OCH₃ | OCH₃ | N | |
| 192 | " | " | " | H | OCH₃ | CH₃ | N | |
| 193 | " | H | CONHC₂H₅ | H | OCH₃ | OCH₃ | CH | |
| 194 | " | " | " | H | OCH₃ | CH₃ | CH | |
| 195 | " | " | " | H | OCH₃ | OCH₃ | N | |
| 196 | " | " | " | H | OCH₃ | CH₃ | N | |
| 197 | " | CH₃ | " | H | OCH₃ | OCH₃ | CH | |
| 198 | " | " | " | H | OCH₃ | CH₃ | CH | |
| 199 | " | " | " | H | OCH₃ | OCH₃ | N | |
| 200 | " | " | " | H | OCH₃ | CH₃ | N | |
| 201 | " | H | CSNHC₂H₅ | H | OCH₃ | OCH₃ | CH | |
| 202 | " | " | " | H | OCH₃ | CH₃ | CH | |
| 203 | " | " | " | H | OCH₃ | OCH₃ | N | |
| 204 | " | " | " | H | OCH₃ | CH₃ | N | |
| 205 | " | CH₃ | " | H | OCH₃ | OCH₃ | CH | |
| 206 | " | " | " | H | OCH₃ | CH₃ | CH | |
| 207 | " | " | " | H | OCH₃ | OCH₃ | N | |
| 208 | " | " | " | H | OCH₃ | CH₃ | N | |
| 209 | " | H | SO₂NHCH₃ | H | OCH₃ | OCH₃ | CH | |
| 210 | " | " | " | H | OCH₃ | CH₃ | CH | |
| 211 | " | " | " | H | OCH₃ | OCH₃ | N | |
| 212 | " | " | " | H | OCH₃ | CH₃ | N | |
| 213 | " | CH₃ | " | H | OCH₃ | OCH₃ | CH | |
| 214 | " | " | " | H | OCH₃ | CH₃ | CH | |
| 215 | " | " | " | H | OCH₃ | OCH₃ | N | |
| 216 | " | " | " | H | OCH₃ | CH₃ | N | |

TABLE 4-continued (Id)

| CN | R¹ | R⁴ | R⁵ | R⁷ | X | Y | Z | Mp. °C. |
|---|---|---|---|---|---|---|---|---|
| 217 | " | H | SO₂N(CH₃)₂ | H | OCH₃ | OCH₃ | CH | |
| 218 | " | " | " | H | OCH₃ | CH₃ | CH | |
| 219 | " | " | " | H | OCH₃ | OCH₃ | N | |
| 220 | " | " | " | H | OCH₃ | CH₃ | N | |
| 221 | " | CH₃ | " | H | OCH₃ | OCH₃ | CH | |
| 222 | " | " | " | H | OCH₃ | CH₃ | CH | |
| 223 | " | " | " | H | OCH₃ | OCH₃ | N | |
| 224 | " | " | " | H | OCH₃ | CH₃ | N | |
| 225 | " | | —CH₂CH₂CH₂CO— | H | OCH₃ | OCH₃ | CH | |
| 226 | " | | " | H | OCH₃ | CH₃ | CH | |
| 227 | " | | " | H | OCH₃ | OCH₃ | N | |
| 228 | " | | " | H | OCH₃ | CH₃ | N | |
| 229 | " | | —CH₂CH₂CH₂SO₂— | H | OCH₃ | OCH₃ | CH | |
| 230 | " | | " | H | OCH₃ | CH₃ | CH | |
| 231 | " | | " | H | OCH₃ | OCH₃ | N | |
| 232 | " | | " | H | OCH₃ | CH₃ | N | |
| 233 | " | | —CH₂CH₂CH₂CH₂CO— | H | OCH₃ | OCH₃ | CH | |
| 234 | " | | " | H | OCH₃ | CH₃ | CH | |
| 235 | " | | " | H | OCH₃ | OCH₃ | N | |
| 236 | " | | " | H | OCH₃ | CH₃ | N | |
| 237 | " | | —CH₂CH₂CH₂CH₂SO₂— | H | OCH₃ | OCH₃ | CH | |
| 238 | " | | " | H | OCH₃ | CH₃ | CH | |
| 239 | " | | " | H | OCH₃ | OCH₃ | N | |
| 240 | " | | " | H | OCH₃ | CH₃ | N | |
| 241 | " | | —CH₂CH₂OCH₂CH₂— | H | OCH₃ | OCH₃ | CH | |
| 242 | " | | " | H | OCH₃ | CH₃ | CH | |
| 243 | " | | " | H | OCH₃ | OCH₃ | N | |
| 244 | " | | " | H | OCH₃ | CH₃ | N | |
| 245 | " | H | COC₃H₇ | H | OCH₃ | OCH₃ | CH | |
| 246 | " | " | " | H | OCH₃ | CH₃ | CH | |
| 247 | " | " | " | H | OCH₃ | OCH₃ | N | |
| 248 | " | " | " | H | OCH₃ | CH₃ | N | |
| 249 | " | CH₃ | " | H | OCH₃ | OCH₃ | CH | |
| 250 | " | " | " | H | OCH₃ | CH₃ | CH | |
| 251 | " | " | " | H | OCH₃ | OCH₃ | N | |
| 252 | " | " | " | H | OCH₃ | CH₃ | N | |
| 253 | " | H | COCH₂Cl | H | OCH₃ | OCH₃ | CH | |
| 254 | " | " | " | H | OCH₃ | CH₃ | CH | |
| 255 | " | " | " | H | OCH₃ | OCH₃ | N | |
| 256 | " | " | " | H | OCH₃ | CH₃ | N | |
| 257 | " | CH₃ | " | H | OCH₃ | OCH₃ | CH | |
| 258 | " | " | " | H | OCH₃ | CH₃ | CH | |
| 259 | " | " | " | H | OCH₃ | OCH₃ | N | |
| 260 | " | " | " | H | OCH₃ | CH₃ | N | |
| 261 | " | H | COCHCl₂ | H | OCH₃ | OCH₃ | CH | |
| 262 | " | " | " | H | OCH₃ | CH₃ | CH | |
| 263 | " | " | " | H | OCH₃ | OCH₃ | N | |
| 264 | " | " | " | H | OCH₃ | CH₃ | N | |
| 265 | " | CH₃ | " | H | OCH₃ | OCH₃ | CH | |
| 266 | " | " | " | H | OCH₃ | CH₃ | CH | |
| 267 | " | " | " | H | OCH₃ | OCH₃ | N | |
| 268 | " | " | " | H | OCH₃ | CH₃ | N | |
| 269 | " | H | COCCl₃ | H | OCH₃ | OCH₃ | CH | |
| 270 | " | " | " | H | OCH₃ | CH₃ | CH | |
| 271 | " | " | " | H | OCH₃ | OCH₃ | N | |
| 272 | " | " | " | H | OCH₃ | CH₃ | N | |
| 273 | " | CH₃ | " | H | OCH₃ | OCH₃ | CH | |
| 274 | " | " | " | H | OCH₃ | CH₃ | CH | |
| 275 | " | " | " | H | OCH₃ | OCH₃ | N | |
| 276 | " | " | " | H | OCH₃ | CH₃ | N | |
| 277 | " | H | COCH=CH₂ | H | OCH₃ | OCH₃ | CH | |
| 278 | " | " | " | H | OCH₃ | CH₃ | CH | |
| 279 | " | " | " | H | OCH₃ | OCH₃ | N | |

TABLE 4-continued (Id) structure: benzene ring with R¹, SO₂NH-C(O)-N(R⁷)- connected to triazine with X, Y, Z substituents; CH₂-N(R⁴)(R⁵) group on benzene.

| CN | R¹ | R⁴ | R⁵ | R⁷ | X | Y | Z | Mp. °C. |
|---|---|---|---|---|---|---|---|---|
| 280 | " | " | " | H | OCH₃ | CH₃ | N | |
| 281 | " | CH₃ | " | H | OCH₃ | OCH₃ | CH | |
| 282 | " | " | " | H | OCH₃ | CH₃ | CH | |
| 283 | " | " | " | H | OCH₃ | OCH₃ | N | |
| 284 | " | " | " | H | OCH₃ | CH₃ | N | |
| 285 | " | H | COC≡CH | H | OCH₃ | OCH₃ | CH | |
| 286 | " | " | " | H | OCH₃ | CH₃ | CH | |
| 287 | " | " | " | H | OCH₃ | OCH₃ | N | |
| 288 | " | " | " | H | OCH₃ | CH₃ | N | |
| 289 | " | CH₃ | " | H | OCH₃ | OCH₃ | CH | |
| 290 | " | " | " | H | OCH₃ | CH₃ | CH | |
| 291 | " | " | " | H | OCH₃ | OCH₃ | N | |
| 292 | " | " | " | H | OCH₃ | CH₃ | N | |
| 293 | " | H | COC₆H₅ | H | OCH₃ | OCH₃ | CH | |
| 294 | " | " | " | H | OCH₃ | CH₃ | CH | |
| 295 | " | " | " | H | OCH₃ | OCH₃ | N | |
| 296 | " | " | " | H | OCH₃ | CH₃ | N | |
| 297 | " | CH₃ | " | H | OCH₃ | OCH₃ | CH | |
| 298 | " | " | " | H | OCH₃ | CH₃ | CH | |
| 299 | " | " | " | H | OCH₃ | OCH₃ | N | |
| 300 | " | " | " | H | OCH₃ | CH₃ | N | |
| 301 | " | SO₂C₆H₅ | SO₂C₆H₅ | H | OCH₃ | OCH₃ | CH | |
| 302 | " | " | " | H | OCH₃ | CH₃ | CH | |
| 303 | " | " | " | H | OCH₃ | OCH₃ | N | |
| 304 | " | " | " | H | OCH₃ | CH₃ | N | |
| 305 | " | SO₂CH₃ | SO₂CH₃ | H | OCH₃ | OCH₃ | CH | |
| 306 | " | " | " | H | OCH₃ | CH₃ | CH | |
| 307 | " | " | " | H | OCH₃ | OCH₃ | N | |
| 308 | " | " | " | H | OCH₃ | CH₃ | N | |
| 309 | " | H | COCH₂Br | H | OCH₃ | OCH₃ | CH | |
| 310 | " | " | " | H | OCH₃ | CH₃ | N | |
| 311 | " | CH₃ | " | H | OCH₃ | OCH₃ | CH | |
| 312 | " | " | " | H | OCH₃ | CH₃ | N | |
| 313 | " | H | COCH₂F | H | OCH₃ | OCH₃ | CH | |
| 314 | " | " | " | H | OCH₃ | CH₃ | N | |
| 315 | " | CH₃ | " | H | OCH₃ | OCH₃ | CH | |
| 316 | " | " | " | H | OCH₃ | CH₃ | N | |
| 317 | " | H | COCH₂C≡CH | H | OCH₃ | OCH₃ | CH | |
| 318 | " | " | " | H | OCH₃ | CH₃ | N | |
| 319 | " | CH₃ | " | H | OCH₃ | OCH₃ | CH | |
| 320 | " | " | " | H | OCH₃ | CH₃ | N | |
| 321 | " | H | COCO₂CH₃ | H | OCH₃ | OCH₃ | CH | |
| 322 | " | " | " | H | OCH₃ | CH₃ | N | |
| 323 | " | CH₃ | " | H | OCH₃ | OCH₃ | CH | |
| 324 | " | " | " | H | OCH₃ | CH₃ | N | |
| 325 | " | H | CO₂C₂H₅ | H | OCH₃ | OCH₃ | CH | |
| 326 | " | " | " | H | OCH₃ | CH₃ | N | |
| 327 | " | CH₃ | " | H | OCH₃ | OCH₃ | CH | |
| 328 | " | " | " | H | OCH₃ | CH₃ | N | |
| 329 | " | H | COSCH₃ | H | OCH₃ | OCH₃ | CH | |
| 330 | " | " | " | H | OCH₃ | CH₃ | N | |
| 331 | " | CH₃ | " | H | OCH₃ | OCH₃ | CH | |
| 332 | " | " | " | H | OCH₃ | CH₃ | N | |
| 333 | " | H | CSOCH₃ | H | OCH₃ | OCH₃ | CH | |
| 334 | " | " | " | H | OCH₃ | CH₃ | N | |
| 335 | " | CH₃ | " | H | OCH₃ | OCH₃ | CH | |
| 336 | " | " | " | H | OCH₃ | CH₃ | N | |
| 337 | " | H | CSSCH₃ | H | OCH₃ | OCH₃ | CH | |
| 338 | " | " | " | H | OCH₃ | CH₃ | N | |
| 339 | " | CH₃ | " | H | OCH₃ | OCH₃ | CH | |
| 340 | " | " | " | H | OCH₃ | CH₃ | N | |
| 341 | " | H | COCH(CH₃)₂ | H | OCH₃ | OCH₃ | CH | |
| 342 | " | " | " | H | OCH₃ | CH₃ | N | |

TABLE 4-continued

Structure (Id): benzene ring with R¹ substituent, SO₂NH-C(O)-N(R⁷)- linked to triazine ring with X, Y, Z substituents; benzene also has CH₂-N(R⁴)(R⁵) group.

| CN | R¹ | R⁴ | R⁵ | R⁷ | X | Y | Z | Mp. °C. |
|---|---|---|---|---|---|---|---|---|
| 343 | " | CH₃ | " | H | OCH₃ | OCH₃ | CH | |
| 344 | " | " | " | H | OCH₃ | CH₃ | N | |
| 345 | " | H | COC(CH₃)₃ | H | OCH₃ | OCH₃ | CH | |
| 346 | " | " | " | H | OCH₃ | CH₃ | N | |
| 347 | " | CH₃ | " | H | OCH₃ | OCH₃ | CH | |
| 348 | " | " | " | H | OCH₃ | CH₃ | N | |
| 349 | " | H | CO-Cyclopropyl | H | OCH₃ | OCH₃ | CH | |
| 350 | " | " | " | H | OCH₃ | CH₃ | N | |
| 351 | " | CH₃ | " | H | OCH₃ | OCH₃ | CH | |
| 352 | " | " | " | H | OCH₃ | CH₃ | N | |
| 353 | " | H | CO-Cyclobutyl | H | OCH₃ | OCH₃ | CH | |
| 354 | " | " | " | H | OCH₃ | CH₃ | N | |
| 355 | " | CH₃ | " | H | OCH₃ | OCH₃ | CH | |
| 356 | " | " | " | H | OCH₃ | CH₃ | N | |
| 357 | " | H | CO-Cyclopentyl | H | OCH₃ | OCH₃ | CH | |
| 358 | " | " | " | H | OCH₃ | CH₃ | N | |
| 359 | " | CH₃ | " | H | OCH₃ | OCH₃ | CH | |
| 360 | " | " | " | H | OCH₃ | CH₃ | N | |
| 361 | " | H | CO-Cyclohexyl | H | OCH₃ | OCH₃ | CH | |
| 362 | " | " | " | H | OCH₃ | CH₃ | N | |
| 363 | " | CH₃ | " | H | OCH₃ | OCH₃ | CH | |
| 364 | " | " | " | H | OCH₃ | CH₃ | N | |
| 365 | " | H | CONHCH₂CH₂Cl | H | OCH₃ | OCH₃ | CH | |
| 366 | " | " | " | H | OCH₃ | CH₃ | N | |
| 367 | " | CH₃ | " | H | OCH₃ | OCH₃ | CH | |
| 368 | " | " | " | H | OCH₃ | CH₃ | N | |
| 369 | " | H | CSNHCH₂CH₂Cl | H | OCH₃ | OCH₃ | CH | |
| 370 | " | " | " | H | OCH₃ | CH₃ | N | |
| 371 | " | CH₃ | " | H | OCH₃ | OCH₃ | CH | |
| 372 | " | " | " | H | OCH₃ | CH₃ | N | |
| 373 | " | H | CONH-n-C₄H₉ | H | OCH₃ | OCH₃ | CH | |
| 374 | " | " | " | H | OCH₃ | CH₃ | N | |
| 375 | " | CH₃ | " | H | OCH₃ | OCH₃ | CH | |
| 376 | " | " | " | H | OCH₃ | CH₃ | N | |
| 377 | " | H | CSNHCH₃ | H | OCH₃ | OCH₃ | CH | |
| 378 | " | " | " | H | OCH₃ | CH₃ | N | |
| 379 | " | CH₃ | " | H | OCH₃ | OCH₃ | CH | |
| 380 | " | " | " | H | OCH₃ | CH₃ | N | |
| 381 | " | H | CSNHCH₂CH=CH₂ | H | OCH₃ | OCH₃ | CH | |
| 382 | " | " | " | H | OCH₃ | CH₃ | N | |
| 383 | " | CH₃ | " | H | OCH₃ | OCH₃ | CH | |
| 384 | " | " | " | H | OCH₃ | CH₃ | N | |
| 385 | " | CH₃ | CSNHCH₂COCH₃ | H | OCH₃ | OCH₃ | CH | |
| 386 | " | " | " | H | OCH₃ | CH₃ | N | |
| 387 | " | CH₃ | CSNHCH₂COC₂H₅ | H | OCH₃ | OCH₃ | CH | |
| 388 | " | " | " | H | OCH₃ | CH₃ | N | |
| 389 | " | CH₃ | CONHCH₂COCH₃ | H | OCH₃ | OCH₃ | CH | |
| 390 | " | " | " | H | OCH₃ | CH₃ | N | |
| 391 | " | CH₃ | CONHCH₂COC₂H₅ | H | OCH₃ | OCH₃ | CH | |
| 392 | " | " | " | H | OCH₃ | CH₃ | N | |
| 393 | " | —CONHCH₂CO— | | H | OCH₃ | OCH₃ | CH | |
| 394 | " | " | " | H | OCH₃ | CH₃ | N | |
| 395 | " | H | SO₂CH₂F | H | OCH₃ | OCH₃ | CH | |
| 396 | " | " | " | H | OCH₃ | CH₃ | N | |
| 397 | " | CH₃ | " | H | OCH₃ | OCH₃ | CH | |
| 398 | " | " | " | H | OCH₃ | CH₃ | N | |
| 399 | " | H | SO₂CF₃ | H | OCH₃ | OCH₃ | CH | |
| 400 | " | " | " | H | OCH₃ | CH₃ | N | |
| 401 | " | CH₃ | " | H | OCH₃ | OCH₃ | CH | |
| 402 | " | " | " | H | OCH₃ | CH₃ | N | |
| 403 | " | H | SO₂C₂H₅ | H | OCH₃ | OCH₃ | CH | |
| 404 | " | " | " | H | OCH₃ | CH₃ | N | |
| 405 | " | CH₃ | " | H | OCH₃ | OCH₃ | CH | |

TABLE 4-continued (Id) structure: benzene ring with R¹ substituent, SO₂NH-C(O)-N(R⁷)- linked to triazine with X, Y, Z substituents; benzyl CH₂-N(R⁴)(R⁵) group.

| CN | R¹ | R⁴ | R⁵ | R⁷ | X | Y | Z | Mp. °C. |
|---|---|---|---|---|---|---|---|---|
| 406 | " | " | " | H | OCH₃ | CH₃ | N | |
| 407 | " | H | SO₂-n-C₃H₇ | H | OCH₃ | OCH₃ | CH | |
| 408 | " | " | " | H | OCH₃ | CH₃ | N | |
| 409 | " | CH₃ | " | H | OCH₃ | OCH₃ | CH | |
| 410 | " | " | " | H | OCH₃ | CH₃ | N | |
| 411 | " | OH | COC₂H₅ | H | OCH₃ | OCH₃ | CH | |
| 412 | " | " | " | H | OCH₃ | CH₃ | N | |
| 413 | " | OCH₃ | " | H | OCH₃ | OCH₃ | CH | |
| 414 | " | " | " | H | OCH₃ | CH₃ | N | |
| 415 | " | OH | COCH₂Cl | H | OCH₃ | OCH₃ | CH | |
| 416 | " | " | " | H | OCH₃ | CH₃ | N | |
| 417 | " | OCH₃ | " | H | OCH₃ | OCH₃ | CH | |
| 418 | " | " | " | H | OCH₃ | CH₃ | N | |
| 419 | " | OH | COCF₃ | H | OCH₃ | OCH₃ | CH | |
| 420 | " | " | " | H | OCH₃ | CH₃ | N | |
| 421 | " | OCH₃ | " | H | OCH₃ | OCH₃ | CH | |
| 422 | " | " | " | H | OCH₃ | CH₃ | N | |
| 423 | " | OH | COCH₂OCH₃ | H | OCH₃ | OCH₃ | CH | |
| 424 | " | " | " | H | OCH₃ | CH₃ | N | |
| 425 | " | OCH₃ | " | H | OCH₃ | OCH₃ | CH | |
| 426 | " | " | " | H | OCH₃ | CH₃ | N | |
| 427 | " | OH | COCO₂C₂H₅ | H | OCH₃ | OCH₃ | CH | |
| 428 | " | " | " | H | OCH₃ | CH₃ | N | |
| 429 | " | OCH₃ | " | H | OCH₃ | OCH₃ | CH | |
| 430 | " | " | " | H | OCH₃ | CH₃ | N | |
| 431 | " | OH | COOCH₃ | H | OCH₃ | OCH₃ | CH | |
| 432 | " | " | " | H | OCH₃ | CH₃ | N | |
| 433 | " | OCH₃ | " | H | OCH₃ | OCH₃ | CH | |
| 434 | " | " | " | H | OCH₃ | CH₃ | N | |
| 435 | " | OH | Cyclopropyl | H | OCH₃ | OCH₃ | CH | |
| 436 | " | " | " | H | OCH₃ | CH₃ | N | |
| 437 | " | OCH₃ | " | H | OCH₃ | OCH₃ | CH | |
| 438 | " | " | " | H | OCH₃ | CH₃ | N | |
| 439 | " | OH | COC₆H₅ | H | OCH₃ | OCH₃ | CH | |
| 440 | " | " | " | H | OCH₃ | CH₃ | N | |
| 441 | " | OCH₃ | " | H | OCH₃ | OCH₃ | CH | |
| 442 | " | " | " | H | OCH₃ | CH₃ | N | |
| 443 | " | OH | COCH(CH₃)₂ | H | OCH₃ | OCH₃ | CH | |
| 444 | " | " | " | H | OCH₃ | CH₃ | N | |
| 445 | " | OCH₃ | " | H | OCH₃ | OCH₃ | CH | |
| 446 | " | " | " | H | OCH₃ | CH₃ | N | |
| 447 | " | OH | COCH=CH₂ | H | OCH₃ | OCH₃ | CH | |
| 448 | " | " | " | H | OCH₃ | CH₃ | N | |
| 449 | " | OCH₃ | " | H | OCH₃ | OCH₃ | CH | |
| 450 | " | " | " | H | OCH₃ | CH₃ | N | |
| 451 | " | OH | COC≡CH | H | OCH₃ | OCH₃ | CH | |
| 452 | " | " | " | H | OCH₃ | CH₃ | N | |
| 453 | " | OCH₃ | " | H | OCH₃ | OCH₃ | CH | |
| 454 | " | " | " | H | OCH₃ | CH₃ | N | |
| 455 | " | OH | SO₂CH₃ | H | OCH₃ | OCH₃ | CH | |
| 456 | " | " | " | H | OCH₃ | CH₃ | N | |
| 457 | " | OCH₃ | " | H | OCH₃ | OCH₃ | CH | |
| 458 | " | " | " | H | OCH₃ | CH₃ | N | |
| 459 | " | OH | SO₂NHCH₃ | H | OCH₃ | OCH₃ | CH | |
| 460 | " | " | " | H | OCH₃ | CH₃ | N | |
| 461 | " | OCH₃ | " | H | OCH₃ | OCH₃ | CH | |
| 462 | " | " | " | H | OCH₃ | CH₃ | N | |
| 463 | " | OH | SO₂N(CH₃)₂ | H | OCH₃ | OCH₃ | CH | |
| 464 | " | " | " | H | OCH₃ | CH₃ | N | |
| 465 | " | OCH₃ | " | H | OCH₃ | OCH₃ | CH | |
| 466 | " | " | " | H | OCH₃ | CH₃ | N | |
| 467 | " | C₂H₅ | CHO | H | OCH₃ | OCH₃ | CH | |
| 468 | " | " | " | H | OCH₃ | CH₃ | N | |

TABLE 4-continued (Id)

| CN | R¹ | R⁴ | R⁵ | R⁷ | X | Y | Z | Mp. °C. |
|---|---|---|---|---|---|---|---|---|
| 469 | " | " | COCH₃ | H | OCH₃ | OCH₃ | CH | |
| 470 | " | " | " | H | OCH₃ | CH₃ | N | |
| 471 | " | " | Cyclopropyl | H | OCH₃ | OCH₃ | CH | |
| 472 | " | " | " | H | OCH₃ | CH₃ | N | |
| 473 | " | " | COCH₂Cl | H | OCH₃ | OCH₃ | CH | |
| 474 | " | " | " | H | OCH₃ | CH₃ | N | |
| 475 | " | " | COCF₃ | H | OCH₃ | OCH₃ | CH | |
| 476 | " | " | " | H | OCH₃ | CH₃ | N | |
| 477 | " | " | COOCH₃ | H | OCH₃ | OCH₃ | CH | |
| 478 | " | " | " | H | OCH₃ | CH₃ | N | |
| 479 | " | " | COC₆H₅ | H | OCH₃ | OCH₃ | CH | |
| 480 | " | " | " | H | OCH₃ | CH₃ | N | |
| 481 | " | " | CONHC₂H₅ | H | OCH₃ | OCH₃ | CH | |
| 482 | " | " | " | H | OCH₃ | CH₃ | N | |
| 483 | " | " | CSNHC₂H₅ | H | OCH₃ | OCH₃ | CH | |
| 484 | " | " | " | H | OCH₃ | CH₃ | N | |
| 485 | " | " | SO₂CH₃ | H | OCH₃ | OCH₃ | CH | |
| 486 | " | " | " | H | OCH₃ | CH₃ | N | |
| 487 | " | " | SO₂NHCH₃ | H | OCH₃ | OCH₃ | CH | |
| 488 | " | " | " | H | OCH₃ | CH₃ | N | |
| 489 | " | " | SO₂N(CH₃)₂ | H | OCH₃ | OCH₃ | CH | |
| 490 | " | " | " | H | OCH₃ | CH₃ | N | |
| 491 | " | " | SO₂C₆H₅ | H | OCH₃ | OCH₃ | CH | |
| 492 | " | " | " | H | OCH₃ | CH₃ | N | |
| 493 | CO₂C₂H₅ | H | CHO | H | OCH₃ | OCH₃ | CH | |
| 494 | " | " | " | H | OCH₃ | CH₃ | N | |
| 495 | " | " | COCH₃ | H | OCH₃ | OCH₃ | CH | |
| 496 | " | " | " | H | OCH₃ | CH₃ | N | |
| 497 | " | " | SO₂CH₃ | H | OCH₃ | OCH₃ | CH | |
| 498 | " | " | " | H | OCH₃ | CH₃ | N | |
| 499 | " | CH₃ | CHO | H | OCH₃ | OCH₃ | CH | |
| 500 | " | " | " | H | OCH₃ | CH₃ | N | |
| 501 | " | " | COCH₃ | H | OCH₃ | OCH₃ | CH | |
| 502 | " | " | " | H | OCH₃ | CH₃ | N | |
| 503 | " | " | SO₂CH₃ | H | OCH₃ | OCH₃ | CH | |
| 504 | " | " | " | H | OCH₃ | CH₃ | N | |
| 505 | " | C₂H₅ | CHO | H | OCH₃ | OCH₃ | CH | |
| 506 | " | " | " | H | OCH₃ | CH₃ | N | |
| 507 | " | " | COCH₃ | H | OCH₃ | OCH₃ | CH | |
| 508 | " | " | " | H | OCH₃ | CH₃ | N | |
| 509 | " | " | SO₂CH₃ | H | OCH₃ | OCH₃ | CH | |
| 510 | " | " | " | H | OCH₃ | CH₃ | N | |
| 511 | " | OH | CHO | H | OCH₃ | OCH₃ | CH | |
| 512 | " | " | " | H | OCH₃ | CH₃ | N | |
| 513 | " | " | COCH₃ | H | OCH₃ | OCH₃ | CH | |
| 514 | " | " | " | H | OCH₃ | CH₃ | N | |
| 515 | " | " | SO₂CH₃ | H | OCH₃ | OCH₃ | CH | |
| 516 | " | " | " | H | OCH₃ | CH₃ | N | |
| 517 | " | OCH₃ | CHO | H | OCH₃ | OCH₃ | CH | |
| 518 | " | " | " | H | OCH₃ | CH₃ | N | |
| 519 | " | " | COCH₃ | H | OCH₃ | OCH₃ | CH | |
| 520 | " | " | " | H | OCH₃ | CH₃ | N | |
| 521 | COO-n-Bu | H | CHO | H | " | OMe | CH | |
| 522 | CONMe₂ | Me | " | H | " | Me | N | |
| 523 | CONHMe | H | " | H | " | OMe | CH | |
| 524 | CO—SMe | Me | CO—Me | H | " | Me | N | |
| 525 | CO—OMe | n-Bu | CHO | H | " | OMe | CH | |
| 526 | " | n-Bu | " | H | " | Me | N | |
| 527 | " | H | " | H | OCH₂CF₃ | NMe₂ | N | |
| 528 | " | Me | " | H | " | " | N | |
| 529 | " | H | CO—Me | H | " | " | N | |
| 530 | " | Me | " | H | " | " | N | |
| 531 | " | " | SO₂CH₃ | H | OCH₃ | OCH₃ | CH | |

TABLE 4-continued (Id)

structure: benzene ring with R¹ substituent, O=C-SO₂NH bridge to N(R⁷) connected to triazine ring with X, Y, Z substituents; benzyl-N(R⁴)(R⁵) group

| CN | R¹ | R⁴ | R⁵ | R⁷ | X | Y | Z | Mp. °C. |
|---|---|---|---|---|---|---|---|---|
| 532 | " | " | " | H | OCH₃ | CH₃ | N | |
| 533 | CO₂CH₃ | CH₃–C(=CH–C(CH₃)=)– (dienyl) | | H | OCH₃ | OCH₃ | CH | |
| 534 | " | | " | H | OCH₃ | CH₃ | N | |

B. FORMULATION EXAMPLES a) A dusting agent is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurinate as the wetting and dispersing agent, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (Triton® X 207), 3 parts by weight of isotridecanol polyglycol ether (8 EO) and 71 parts by weight of paraffinic mineral oil (boiling range, for example, about 255 to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of ethoxylated nonylphenol as emulsifier.

e) Water-dispersible granules are obtained by mixing
 75 parts by weight of a compound of the formula (I),
 10 parts by weight of calcium ligninsulfonate,
 5 parts by weight of sodium lauryl sulfate,
 3 parts by weight of polyvinyl alcohol and
 7 parts by weight of kaolin,
grinding the mixture in a pinned-disk mill and granulating the powder in a fluidized bed by spraying on water as granulation liquid.

f) Water-dispersible granules are also obtained by homogenizing and precomminuting, in a colloid mill,
 25 parts by weight of a compound of the formula (I),
 5 parts by weight of sodium 2,2'-dinaphthylmethane-6,6'-disulphonate,
 2 parts by weight of sodium oleoylmethyltaurinate,
 1 part by weight of polyvinyl alcohol,
 17 parts by weight of calcium carbonate and
 50 parts by weight of water,
then grinding the mixture in a bead mill, atomizing the resulting suspension in a spray tower using a single-substance nozzle, and drying the product.

C. BIOLOGICAL EXAMPLES

1. Pre-emergence effect on weeds

Seeds or rhizome pieces of monocotyledon and dicotyledon weed plants are placed in sandy loam soil in plastic pots and covered with soil. The compounds of the formula (I) according to the invention or their salts, which were formulated in the form of wettable powders or emulsion concentrates, are then applied to the surface of the soil cover in the form of an aqueous suspension or emulsion at an application rate of 600 to 800 l of water/ha (converted), in various dosages.

After the treatment, the pots are placed in a greenhouse and kept under good growth conditions for the weeds. After the test plants have emerged the damage to the plants or the negative effect on emergence is scored visually after a test period of 3 to 4 weeks by comparison with untreated controls. As shown by the test results, the compounds according to the invention have a good herbicidal pre-emergence activity against a broad range of grass weeds and dicotyledon weeds. For example, the compounds of Examples 1, 27, 53 to 55, 58, 59, 79, 105, 113, 129, 145, 153, 177, 181, 185, 189, 213, 217, 221, 253, 257, 421, 425, 429, 433, 437, 445, 457, 461, 465, 467, 485, 487, 535 to 543, 547, 551 to 559, 562, 563 and 565 to 578 from Table 1 and Examples 1, 27, 53, 79, 153, 161, 169, 177, 181, 185, 253, 261, 269, 341, 349, 365 and 373 from Table 2 and Examples 27 and 535 from Table 3 and Example 53 from Table 4 have a good herbicidal pre-emergence action against nuisance plants such as *Sinapis alba, Stellaria media, Chrysanthemum segetum* and *Lolium multiflorum* when applied at a rate of from 0.3 kg to 0.005 kg of active substance per hectare.

2. Post-emergence effect on weeds

Seeds or rhizome pieces of monocotyledon and dicotyledon weeds are placed in sandy loam soil in plastic pots, covered with soil and grown in a greenhouse under good growth conditions. Three weeks after sowing, the test plants are treated at the three-leaf stage. The compounds of the formula (I) according to the invention or their salts, which were formulated as wettable powders or as emulsion concentrates, are sprayed in various dosages at an application rate of from 600 to 800 1 of water/ha (converted) onto the green parts of the plants and, after the test plants have remained in the greenhouse for about 3 to 4 weeks under ideal growth conditions, the action of the preparations is scored visually by comparison with untreated controls. The agents according to the invention also have a good herbicidal post-emergence action against a broad range of economically important grass weeds and dicotyledon weeds. For example, the compounds of Examples 1, 27, 53 to 55, 58, 59, 79, 105, 113, 129, 145, 153, 177, 181, 185, 189, 213, 217, 221, 253, 257, 421, 425, 429, 433, 437, 445, 457, 461, 465, 467, 485, 487, 535 to 543, 547, 551 to 559, 562, 563 and 565 to 578 from Table 1 and Examples 1, 27, 53, 79, 153, 161, 169, 177, 181, 185, 253, 261, 269, 341, 349, 365 and 373 from Table 2 and Examples 27 and 535 from Table 3 and Example 53 from Table 4 have a very good herbicidal post-emergence action against nuisance plants such as *Sinapis alba, Stellaria media, Chrysanthemum segetum* and *Lolium multiflorum* when applied at a rate of from 0.3 kg to 0.005 kg of active substance per hectare.

3. Tolerance by crop plants

In further greenhouse experiments, seeds of a substantial number of crop plants and weeds were placed in sandy loam soil and covered with soil.

Some of the pots were treated immediately as described under 1., and the remaining pots were placed in a greenhouse until the plants had developed two to three true leaves and were then sprayed with various dosages of the substances of the formula (I) according to the invention or their salts, as described under 2.

Visual scoring four to five weeks after the application and after the plants had been in the greenhouse revealed that the compounds according to the invention did not inflict any damage on dicotyledon crops such as, for example, soya, cotton, oilseed rape, sugar beet and potatoes when used pre- and post-emergence, even at high dosages of active substance. Moreover, some substances even left Gramineae crops such as barley, wheat, rye, sorghum millets, maize or rice unharmed. The compounds of the formula (I) or salts thereof therefore have a high selectivity when used for controlling unwanted plant growth in agricultural crops.

We claim:

1. A compound of the formula (I) or salts thereof,

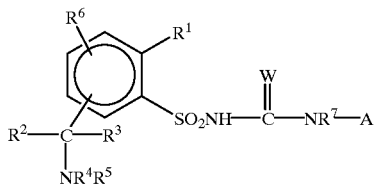

(I)

in which $R^1$ is CO—Q—$R^8$, $R^2$ and $R^3$ independently of one another are H or ($C_1$–$C_4$) alkyl, $R^4$ is H, ($C_1$–$C_8$)alkyl which is unsubstituted or is substituted by one or more radicals from the group consisting of halogen, ($C_1$–$C_4$)alkoxy, ($C_1$–$C_4$)alkylthio, ($C_1$–$C_4$)alkylsulfinyl, ($C_1$–$C_4$)alkylsufonyl, [($C_1$–$C_4$)alkoxy]carbonyl and CN, or is ($C_3$–$C_6$)alkenyl which is unsubstituted or is substituted by one or more halogen atoms, or is ($C_3$–$C_6$)alkynyl which is unsubstituted or is substituted by one or more halogen atoms, or is hydroxyl, ($C_1$–$C_4$)alkoxy, [($C_1$–$C_4$)alkyl]carbonyl or ($C_1$–$C_4$)alkylsulfonyl, each of the three latter radicals being unsubstituted or substituted in the alkyl moiety by one or more halogen atoms or by ($C_1$–$C_4$)alkoxy or ($C_1$–$C_4$)alkylthio, or is phenylsulfonyl in which the phenyl radical is unsubstituted or substituted, and $R^5$ is ($C_1$–$C_4$)alkylsulfonyl or ($C_3$–$C_6$)alkenylsulfonyl, each of the two latter radicals being unsubstituted or substituted by one or more halogen atoms or by ($C_1$–$C_4$)alkoxy or ($C_1$–$C_4$)alkylthio, or is phenylsulfonyl or phenylcarbonyl, the phenyl radical in each of the two latter radicals being unsubstituted or substituted, or is mono- or di-[($C_1$–$C_4$)alkyl]aminosulfonyl or [($C_1$–$C_4$)alkyl]carbonyl, each of the three latter radicals being unsubstituted or substituted by one or more radicals from the group consisting of halogen, ($C_1$–$C_4$) alkoxy, ($C_1$–$C_4$)alkylthio, ($C_1$–$C_4$)alkylsulfinyl, ($C_1$–$C_4$)alkylsulfonyl, [($C_1$–$C_4$)alkyl]carbonyl, [($C_1$–$C_4$)alkoxy]carbonyl and CN, or is formyl, a group of the formula —CO—CO—R' in which R'=H, OH, ($C_1$–$C_4$)alkoxy or ($C_1$–$C_4$)alkyl, or is [($C_3$–$C_6$) cycloalkyl]carbonyl, [($C_2$–$C_6$)alkenyl]carbonyl or [($C_2$–$C_6$)alkynyl]carbonyl, each of the three latter radicals being unsubstituted or substituted by one or more halogen atoms, or is a group of the formula

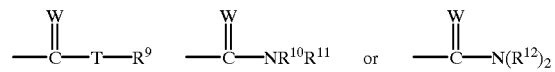

with the exception of the definition $R^5$=unsubstituted [($C_1$–$C_6$)alkyl]-carbonyl, if the radical of the formula —$CR^2R^3$—$NR^4R^5$ is in para-position of the $SO_2$ group at the phenyl ring, or $R^4$ and $R^5$ together are a chain of the formula (—$CH_2$) $_m B^2$— or —$B^1$—($CH_2$)$_{m1}B^2$—, the chain being unsubstituted or substituted by one or more ($C_1$–$C_3$)alkyl radicals and m being 3 or 4 or $m^1$ being 2 or 3, and W is an oxygen or sulfur atom, $B^1$ and $B^2$ independently of one another are $SO_2$ or CO, Q is O, S or —$NR^{13}$—, T is O or S, $R^6$ is H, ($C_1$–$C_4$)alkyl, ($C_1$–$C_4$)alkoxy, [($C_1$–$C_4$)-alkyl] carbonyl or [($C_1$–$C_4$)alkoxy]carbonyl, each of the 4 latter radicals being unsubstituted or substituted in the alkyl moiety by one or more halogen atoms, or is halogen, $NO_2$ or CN, $R^7$ is H or $CH_3$, $R^8$ is H, ($C_1$–$C_4$)alkyl, ($C_3$–$C_4$)alkenyl or ($C_3$–$C_4$)-alkynyl, each of the three latter radicals being unsubstituted or substituted by one or more radicals from the group consisting of halogen, ($C_1$–$C_4$)alkoxy, ($C_1$–$C_4$) alkylthio, [($C_1$–$C_4$)alkyl]carbonyl and [($C_1$–$C_4$) alkoxy]-carbonyl, $R^9$ is ($C_1$–$C_4$)alkyl, ($C_3$–$C_4$)alkenyl or ($C_3$–$C_4$)alkynyl, each of the three latter radicals being unsubstituted or substituted by one or more radicals from the group consisting of halogen, ($C_1$–$C_4$)alkoxy, ($C_1$–$C_4$) alkylthio, [($C_1$–$C_4$)alkyl]carbonyl and [($C_1$–$C_4$) alkoxyl]-carbonyl, $R^{10}$ and $R^{11}$ independently of one another are H, ($C_1$–$C_4$) alkyl, ($C_3$–$C_4$)alkenyl or ($C_3$–$C_4$)alkynyl, each of the three latter radicals being unsubstituted or substituted by one or more radicals being unsubstituted or substituted by one or more radicals from the group consisting of halogen, $(C_1-C_4)$alkoxy, $(C_1-C_4)$alkylthio, $[(C_1-C_4)$alkyl]carbonyl and $[(C_1-C_4)$alkoxy]carbonyl, the radicals $R^{12}$ together with the nitrogen atom are a heterocyclic ring having 5 or 6 ring members selected from the group consisting of 1-pyrrolidinyl 1-piperidinyl and 4-morpholinyl, which is unsubstituted or is substituted by $(C_1-C_4)$alkyl, $R^{13}$ is H, $(C_1-C_4)$alkyl, $(C_3-C_4)$alkenyl or $(C_3-C_4)$alkynyl, each of the three latter radicals being unsubstituted or substituted by one or more radicals from the group consisting of halogen, $(C_1-C_4)$alkoxy and $(C_1-C_4)$alkylthio, A is a radical of the formula,

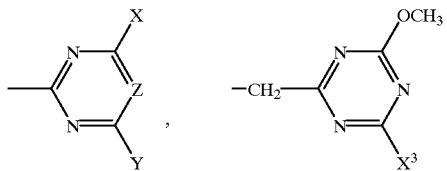

one of the radicals X and Y is hydrogen, halogen, $(C_1-C_3)$alkyl or $(C_1-C_3)$alkoxy, the two latter radicals being unsubstituted or being mono- or polysubstituted by halogen or monosubstituted by $(C_1-C_3)$alkoxy, and the other of the radicals X and Y is hydrogen, $(C_1-C_3)$alkyl, $(C_1-C_3)$alkoxy or $(C_1-C_3)$alkylthio, the three latter alkyl-containing radicals being unsubstituted or mono- or polysubstituted by halogen or mono- or disubstituted by $(C_1-C_3)$alkoxy or $(C_1-C_3)$alkylthio, or is a radical of the formula $NR^{14}R^{15}$, $(C_3-C_6)$cycloalkyl, $(C_2-C_4)$alkenyl, $(C_2-C_4)$alkynyl, $(C_3-C_4)$alkenyloxy or $(C_3-C_4)$alkynyloxy, Z is N, $R^{14}$ and $R^{15}$ independently of one another are H, $(C_1-C_3)$alkyl or $(C_3-C_4)$alkenyl, $X^3$ is $CH_3$ or $OCH_3$, $Y^5$ is $CH_3$, $C_2H_5$, $OCH_3$ or Cl.

2. A compound of formula (I) or salts thereof as claimed in claim 1, wherein $R^2$ is H, $R^3$ is H, $R^4$ is H or $(C^1-C^4)$alkyl, $R^5$ is $(C_1-C_4)$alkylsulfonyl, $[(C_1-C_4)$alkyl]-carbonyl, a group of the formula —C(=W)—T—$R^9$ in which W is O or S; T is O or S, and $R^9$ is $(C^1-C^4)$alkyl, $(C_3-C_4)$alkenyl or $(C_3-C_4)$alkynyl, $R^6$ is H, $R^7$ is H, A is a group of the formula,

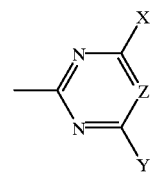

Z is N,

X is methyl, methoxy or chloro, and

Y is methyl, or methoxy.

3. A compound of formula (I) or salts thereof as claimed in claim 2, wherein $R^5$ is $(C_1-C_4)$alkylsulfonyl.

4. A compound of formula (I) or salts thereof as claimed in claim 2, wherein $R^5$ is $(C_1-C_4)$alkyl]-carbonyl.

5. A compound of formula (I) or salts thereof as claimed in claim 2, wherein $R^5$ a group of the formula —CO—O—$R^9$ and $R^9$ is $(C_1-C_4)$alkyl.

6. A compound or salt thereof as claimed in claim 1 wherein $R^4$ is H, $(C_1-C_4)$alkyl, which is unsubstituted or is substituted by one or more radicals from the group consisting of halogen, $(C_1-C_4)$alkoxy, $(C_1-C_4)$alkylthio, $(C_1-C_4)$alkylsulfonyl, $[(C_1-C_4)$alkoxy]carbonyl and CN, or is $(C_3-C_4)$alkenyl, $(C_3-C_4)$alkynyl, hydroxyl, $(C_1-C_4)$alkoxy, $[(C_1-C_4)$alkyl]carbonyl or $(C_1-C_4)$alkylsulfonyl, each of the five latter radicals being unsubstituted or substituted in the alkyl moiety by one or more halogen atoms, or is phenylsulfonyl in which the phenyl radical is unsubstituted or is substituted by one or more radicals from the group consisting of halogen, $(C_1-C_4)$alkyl and $(C_1-C_4)$alkoxy, and $R^5$ is $(C_1-C_4)$alkylsulfonyl, $(C_1-C_4)$haloalkylsulfonyl, phenylsulfonyl or phenylcarbonyl, the phenyl radical in the two latter radicals being unsubstituted or substituted by one or more radicals from the group consisting of halogen, $(C_1-C_4)$alkyl and $(C_1-C_4)$alkoxy, or is mono- or di-$[(C_1-C_4)$alkyl]aminosulfonyl, $[(C_1-C_6)$alkyl]carbonyl which is unsubstituted or is substituted by one or more halogen atoms or by $(C_1-C_4)$alkoxy or $(C_1-C_4)$alkylthio, or is formyl, OHC—CO—, 2-oxo-$(C_3-C_5)$alkanoyl, $[(C_1-C_4)$alkoxy]oxalyl, $[(C_3-C_6)$cycloalkyl]carbonyl, $[(C_2-C_4)$alkenyl]carbonyl or $[(C_2-C_4)$alkynyl]carbonyl or is a group of the formula

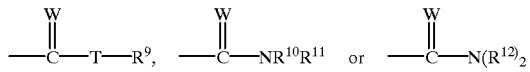

W is O or S, $R^6$ is H, $(C_1-C_4)$alkyl, $(C_1-C_4)$haloalkyl, $(C_1-C_4)$alkoxy, $(C_1-C_4)$haloalkoxy or halogen, $R^8$ is at each occurrence $(C_1-C_4)$alkyl which is unsubstituted or is substituted by one or more halogen atoms, or is $(C_3-C_4)$alkenyl or $(C_3-C_4)$alkynyl, $R^9$ is H, $(C_1-C_4)$alkyl which is unsubstituted or is substituted by one or more halogen atoms or by $(C_1-C_4)$ alkoxy, $(C_1-C_4)$alkylthio, $[(C_1-C_4)$alkoxy]carbonyl and $[(C_1-C_4)$alkyl]carbonyl, $R^{10}$ and $R^{11}$ independently of one another are H, $(C_1-C_4)$alkyl which is unsubstituted or is substituted by one or more halogen atoms, or are $(C_3-C_4)$alkenyl or $(C_3-C_4)$alkynyl, at least one of the radicals $R^{10}$ and $R^{11}$ being different from hydrogen, the radicals $R^{12}$ together with the nitrogen atom are a heterocyclic ring having 5 or 6 ring members, selected from the group consisting of 1-pyrrolidinyl, 1-piperidinyl and 4-morpholinyl which is unsubstituted or is substituted by $(C_1-C_4)$alkyl or by the oxo group, and $R^{13}$ is at each occurrence H, $(C_1-C_4)$alkyl which is unsubstituted or is substituted by one or more halogen atoms, or is $(C_3-C_4)$alkenyl or $(C_3-C_4)$alkynyl.

7. A compound or salt thereof as claimed in claim 1, wherein $R^4$ is H, $(C_1-C_4)$alkyl, hydroxyl or $(C_1-C_4)$alkoxy, $R^5$ is $(C_1-C_4)$alkylsulfonyl, CHO, $[(C_1-C_4)$alkyl]carbonyl which is unsubstituted or is substituted by one or more halogen atoms, or is $[(C_1-C_4)$alkoxy]oxalyl, $[(C_3-C_6)$cycloalkyl]carbonyl or a group of the formula

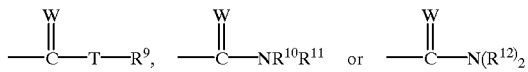

in which

W, T and $R^9$ to $R^{12}$ are as defined above for formula (I), $R^6$ is H, $(C_1-C_3)$alkyl, $(C_1-C_3)$alkoxy or halogen, A is a radical of the formula

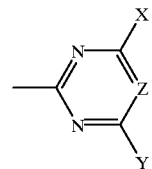

Z is N, and one of the radicals X and Y is halogen, $(C_1-C_2)$alkyl, $(C_1-C_2)$alkoxy, $OCF_2H$, $CF_3$ or $OCH_2CF_3$ and the other of the radicals X and Y is $(C_1-C_2)$alkyl, $(C_1-C_2)$alkoxy or $(C_1-C_2)$haloalkoxy.

8. A herbicidal or plant growth-regulating composition, which comprises one or more compounds of the formula (I) or salt thereof as claimed in claim 1 and formulation auxiliaries which are conventional in crop protection.

9. A method for controlling nuisance plants or for regulating the growth of plants, which comprises applying an effective quantity of one or more compounds of the formula (I) or of a salt thereof as claimed in claim 1 to the nuisance plants or plants, the plant seeds or the area on which they are growing.

* * * * *